(12) United States Patent
Weis et al.

(10) Patent No.: US 6,174,898 B1
(45) Date of Patent: Jan. 16, 2001

(54) METHOD OF TREATING FILARIAE

(75) Inventors: Jan Ulrik Weis, Virum; Knud Erik Andersen, Smørum, both of (DK)

(73) Assignee: Novo Nordisk A/S, Bagsvaerd (DK)

( * ) Notice: Under 35 U.S.C. 154(b), the term of this patent shall be extended for 0 days.

(21) Appl. No.: 09/066,318

(22) PCT Filed: Oct. 31, 1996

(86) PCT No.: PCT/DK96/00453

§ 371 Date: Apr. 28, 1998

§ 102(e) Date: Apr. 28, 1998

(87) PCT Pub. No.: WO97/17073

PCT Pub. Date: May 15, 1997

(30) Foreign Application Priority Data

Nov. 3, 1995 (DK) .................................................. 1230/95

(51) Int. Cl.$^7$ ......................... A01N 43/40; A61K 31/445
(52) U.S. Cl. ........................... 514/315; 514/326; 514/422; 514/428
(58) Field of Search ..................................... 514/315, 326, 514/422, 428

(56) References Cited

FOREIGN PATENT DOCUMENTS 42 07 400 A1    9/1993   (DE) .

*Primary Examiner*—Dwayne C. Jones
(74) *Attorney, Agent, or Firm*—Steve T. Zelson, Esq.; Elias J. Lambiris, Esq.

(57) ABSTRACT

The present invention relates to a novel method for treating a mammal suffering from filariae.

19 Claims, No Drawings

METHOD OF TREATING FILARIAE

CROSS-REFERENCE TO RELATED APPLICATIONS

This application is a 35 U.S.C. 371 national application of PCT/DK96/00453 filed Oct. 31, 1996 and claims priority under 35 U.S.C. 119 of Danish application 1230/95 filed Nov. 3, 1995, the contents of which are fully incorporated herein by reference.

FIELD OF THE INVENTION

The present invention relates to the use of N-substituted azaheterocyclic carboxylic acids and esters thereof in which a substituted alkyl chain forms part of the N-substituent and salts thereof in the clinical treatment of filariae in the lymphatic system.

BACKGROUND OF THE INVENTION

Of the six major tropical diseases (filariasis, schistosomiasis, malaria, leishmaniasis, trypanosomiasis and leprosy) recognized by WHO as the main cause of morbidity, mortality and poor socio-economic growth in the tropics, filariasis is one of the most widespread and debilitating diseases of humans.

Filariasis is a helminthic infection caused by a number of slender and thread-like nematodes which invade blood circulation, lymphatics, lymph nodes, connective and subcutaneous tissues, peritoneal cavities and other parts of the human body.

The disease is transmitted to man by a large variety of hematophagous arthropods, often mosquitoes and flies, which introduce a large number of infective larvae in blood circulation while feeding on the human blood. The female worms produce microfilariae which make their way to blood circulation and subcutaneous tissues from where they are taken up by a suitable insect vector. On reaching the insect's body, the microfilariae (first stage larvae, Li larvae) undergo several moultings to form infective larvae (L3 larvae) which reach the blood circulation of the definite host through the bites of the insect. Soon the infective larvae enter into lymphatic system and connective tissues where they slowly mature into adult male and female worms. The male and female adult mate to produce microfilariae which find their way to peripheral blood circulation.

It is estimated that nearly 300 to 400 million people around the world are infected with different forms of filariasis and many more are living at the risk of acquiring such infections.

The clinical manifestations of lymphatic filariasis are characterized by three phases:
(1) Inflammatory, leading to high fever, chills, vomiting, malaise, enlargement of lymph nodes, pain and swelling in the testes and thickening of spermatic cord.
(2) Obstructive, causing blockade of the lymphatic circulation which slowly leads to hydrocele and chyluria.
(3) Elephantiasis, marked by massive enlargement of legs, arms, scrotum and breasts.

The early stage of onchocerciasis (river blindness) is marked by skin rash and persistent pruritis (onchodermatitis) followed by pachydermia over thighs and buttocks. Later the patient may develop pain in the eyes, photophobia, lacrimation and edema of eyelids which slowly leads to chronic conjuctivitis; finally the patient loses vision. River blindness thus poses a serious problem in many parts of the African continent causing loss of vision and blindness due to damage of cornea, iris and pupil by entrance of microfilariae into the eyeball of a large number of patients every year.

In recent years much pharmacological research concerning y-aminobutyric acid (hereinafter designated GABA), an inhibitory neurotransmitter in the mammalian central nervous system, has been carried out. As a result, much interest has been focused on the various potential pharmacological approaches to the enhancement of GABA'ergic function in humans, for example, by the direct agonism on GABA receptors, the inhibition of enzymatic breakdown of GABA, or by the inhibition of the uptake of GABA into neuronal and glial cell bodies. Recently, the discovery of high levels of GABA in microfilariae suggested the existence of GABA receptors in such organisms, thereby creating a new field of interest in filariae therapeutics by GABA'ergic compounds (J. Pharm. Pharmacol. 1989, 41, 191). It has been shown that filariae are sensitive (paralysis or death) to high concentrations of GABA inside the parasite. However, the passage of GABA through the parasite cuticle is poor due to its relatively polar nature excluding this compound as a therapeutic. The obvious modification by preparation of the more lipophilic prodrug esters of GABA has been investigated (J. Pharm. Pharmacol. 1989, 41, 191). A different approach to enhancement of GABA'ergic function inside the parasite is the embodiment of this invention where compounds known as lipophilic GABA uptake inhibitors now has been shown to exhibit paralysis and death of such parasites. Furthermore, the compounds of the invention has been found to be orally active.

DESCRIPTION OF THE INVENTION

The method of this invention comprises administering to a patient suffering from filariae in the lymphatic system an effective amount of a compound of formula I

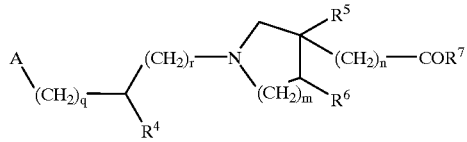

wherein A is

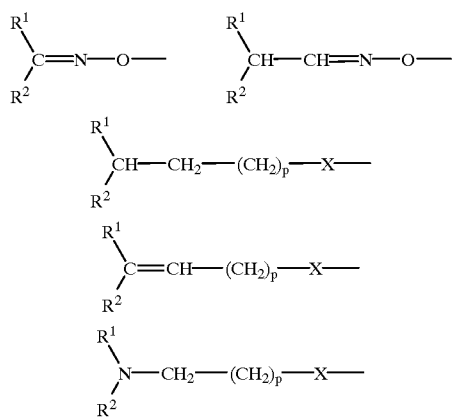

wherein $R^1$ and $R^2$ independently are furanyl, imidazolyl, oxazolyl, phenyl, pyrazolyl, pyrazinyl, pyridazinyl, pyridinyl, pyrimidinyl, pyrrolyl, thiazolyl, thienyl or triazolyl wherein each aromatic ring is optionally substituted with one, two or three substituents selected from —$NR^8R^9$, $C_{1-8}$-alkylthio, $C_{1-6}$-alkoxy, azido, cyano, halogen, hydroxy, $C_{1-6}$-alkyl, nitro, mercapto or trifluoromethyl; and X is —CH$_2$—, —O— or —N(R$^3$)— wherein R$^3$ is hydrogen or C$_{1-6}$-alkyl; and R$^4$ is hydrogen or C$_{1-6}$-alkyl; and m is 1 or 2; and n is 1 when m is 1 and n is 0 when m is 2; and R$^5$ and R$^6$ each represents hydrogen or may when m is 2 together represent a bond; and R$^7$ is hydroxy or C$_{1-6}$-alkoxy; and R$^8$ and R$^9$ independently are hydrogen or C$_{1-6}$-alkyl; and p is 0, 1, 2 or 3; and q is 0, 1 or 2; and r is 0, 1 or 2; or a pharmaceutically acceptable salt thereof.

The compounds according to the invention may optionally exist as pharmaceutically acceptable acid addition salts or—when the carboxylic acid group is not esterified—as pharmaceutically acceptable metal salts or—optionally alkylated—ammonium salts.

Examples of such salts include inorganic and organic acid addition salts such as hydrochloride, hydrobromide, sulphate, phosphate, acetate, fumarate, maleate, citrate, lactate, tartrate, oxalate, or similar pharmaceutically acceptable inorganic or organic acid addition salts, and include the pharmaceutically acceptable salts listed in Journal of Pharmaceutical Science, 66, 2 (1977) which are hereby incorporated by reference.

The compounds of formula I may exist as geometric and optical isomers and all isomers and mixtures thereof are included herein. Isomers may be separated by means of standard methods such as chromatographic techniques or fractional crystallization of suitable salts.

As used herein, the term patient includes any mammal which could benefit from treatment of filariae in the lymphatic system. The term particularly refers to a human patient, but is not intended to be so limited.

The compounds used in the presently claimed invention and methods of preparing them have been disclosed and claimed in EP Appl. no. 89108850.2, EP appl. no. 89123400.7 and EP appl. no. 90917178.7 herein incorporated by reference in their entirety. In these references there is no disclosure of using the compounds to treat filariae.

It has been demonstrated that compounds of formula I possess useful pharmacological properties, in that they cause paralysis and death of filariae. Compounds of formula I may be used to treat, for example, lymphatic filariasis, onchocerciasis and loasis in man.

Pharmacological Methods

Values for the filaricidal activity of the invention compounds were assessed essentially by the method of Deverre et al (J. Pharm. Pharmacol. 1989, 41, 191).

Microfilariae (*Brugia Pahangi* or *Acanthocheilonema vitae*) were obtained from the peritoneal cavity of infected gerbils by lavage with the incubation medium (HEPES-buffered RPMI 1640 supplemented with 50 µg of gentamycin/ml).

The assays were performed in flat-bottomed 96 well trays. Each well contained approximately 100 microfilariae in 150 µl medium to which 50 µl of test solution was added. The temperature was 37° C. The viability of the microfilariae (spontaneous movements) was assessed by means of an inverted microscope after 0.5, 1, 2 and 4 hours of incubation. The results were rated into 4 groups:

+++=Rapid coiling and uncoiling (normal movement)

++=Significant slowing down of movement

+=Microfilariae mostly elongated, but with occasional twitching

0=No movement (microfilariae dead)

The effect of some representative compounds after 4 hours of incubation are recorded in Table I.

TABLE I

| Ex. No. | Brugia Pahangi (0.1 mM) | Acanthocheilonema (0.1 mM) |
| --- | --- | --- |
| Control | +++ | +++ |
| 42 | + | 0 |
| 45 | 0 | − |
| 46 | ++ | − |
| 49 | ++ | 0 |
| 61 | ++ | + |
| 62 | +++ | ++ |
| 89 | +++ | +++ |
| 90 | +++ | +++ |
| 95 | +++ | + |
| 96 | +++ | +++ |
| 150 | ++ | + |

Compounds of formula I are useful because they may possess significant pharmacological activity in man. In particular the compounds of formula I are useful as a consequence of their inhibition of GABA uptake.

For the above indications the dosage will vary depending on the compound of formula I employed, on the mode of administration and on the therapy desired. However, in general, satisfactory results are obtained with a dosage of from about 0.5 mg to about 1000 mg, preferably from about 1 mg to about 500 mg of compounds of formula I, conveniently given from 1 to 5 times daily, optionally in sustained release form. Usually, dosage forms suitable for oral administration comprise from about 0.5 mg to about 1000 mg, preferably from about 1 mg to about 500 mg of the compounds of formula I admixed with a pharmaceutical carrier or diluent. No toxic effects have been observed.

The compounds of formula I may be administered in pharmaceutically acceptable acid addition salt form or where possible as a metal or a lower alkylammonium salt. Such salt forms exhibit approximately the same order of activity as the free base forms.

Typical pharmaceutical compositions include a compound of formula I or a pharmaceutically acceptable salt thereof and, usually, such compositions also contains a pharmaceutical carrier or diluent. The compositions containing the compounds of this invention may be prepared by conventional techniques and appear in conventional forms, for example capsules, tablets, solutions or suspensions.

The pharmaceutical carrier employed may be a conventional solid or liquid carrier. Examples of solid carriers are lactose, terra alba, sucrose, talc, gelatin, agar, pectin, acacia, magnesium stearate and stearic acid.

Examples of liquid carriers are syrup, peanut oil, olive oil and water.

Similarly, the carrier or diluent may include any time delay material known to the art, such as glyceryl monostearate or glyceryl distearate, alone or mixed with a wax.

If a solid carrier for oral administration is used, the preparation can be tabletted, placed in a hard gelatin capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

Generally, the compounds of this invention are dispended in unit dosage form comprising 50–200 mg of active ingredient in or together with a pharmaceutically acceptable carrier per unit dosage.

The dosage of the compounds according to this invention is 1–500 mg/day, e.g. about 100 mg per dose, when administered to patients, e.g. humans, as a drug.

A typical tablet which may be prepared by conventional tabletting techniques contains:

| Core: | |
|---|---|
| Active compound (as free compound or salt thereof) | 100 mg |
| Colloidal silicon dioxide (Aerosil ®) | 1.5 mg |
| Cellulose, microcryst. (Avicel ®) | 70 mg |
| Modified cellulose gum (Ac-Di-Sol ®) | 7.5 mg |
| Magnesium stearate | |
| Coating: | |
| HPMC | approx. 9 mg |
| *Mywacett ® 9-40 T | approx. 0.9 mg |

*Acylated monoglyceride used as plasticizer for film coating.

The route of administration may be any route which effectively transports the active compound to the appropriate or desired site of action, such as oral or parenteral e.g. rectal, transdermal, subcutaneous, intravenous, intraurethral, intramuscular, intranasal, topical, ophthalmic solution or an ointment, the oral route being preferred.

EXAMPLES

The process for preparing compounds of formula I and preparations containing them is further illustrated in the following examples, which, however, are not to be construed as limiting.

Herinafter, TLC is thin layer chromatography, THF is tetrahydrofuran, $CDCl_3$ is deuterio chloroform and DMSO-$d_6$ is hexadeuterio dimethylsulfoxide. The structures of the compounds are confirmed by elemental analysis and NMR. NMR spectra were run on a Bruker WM 400 MHz or 200 MHz apparatus using tetramethylsilane as reference. M.P. is melting point and is given in ° C. HPLC analysis was performed using four reverse phase systems, A: a 5 $\mu$m C18 4×200 mm column eluting with a 35–80% gradient of 0.1% TFA/acetonitrile and 0.1% TFA/water over 30 minutes and T=25° C.; B: a 5 $\mu$m C18 4×250 mm column eluting with a 30–50% gradient of acetonitrile and 0.1 M ammonium sulphate buffer solution (pH 3.3) over 25 minutes and T=35° C.; C: a 5 $\mu$m C18 4×250 mm reverse phase column eluting with 50% acetonitrile and 0.1 M ammonium sulphate buffer solution (pH 3.3) over 30 minutes and T=35° C.; D: a 5 1m C18 4×250 mm column eluting with a 20–80% gradient of 0.1% TFA/acetonitrile and 0.1% TFA/water over 30 minutes and T=35° C. TFA is trifluoroacetic acid. Column chromatography was carried out using the technique described by W. C. Still et al, J. Org. Chem. 43, (1978) 2923–2925 on Merck silica gel 60 (Art. 9385). Compounds used as starting materials are either known compounds or compounds which can readily be prepared by methods known per se.

Example 1

(R)-N-(2-(2-(Diphenylamino)ethoxy)ethyl)-3-piperidinecarboxylic acid ethyl ester A mixture of sodium hydride (0.70 g, 0.023 mol, 80% oil dispersion) and diphenylamine (3.4 g, 0.020 mol) in dry dibutylether (30 ml) was heated at reflux temperature for 1 h under an atmosphere of nitrogen. The reaction mixture was cooled to 50° C. and 2,2'-dichlorodiethylether (10 ml) was added and the mixture was heated at reflux temperature for 16 h. The reaction mixture was cooled, filtered and the volatile components were removed in vacuo leaving 4.6 g of crude 2-chloro-1-(2-(diphenylamino)ethoxy)ethane as an oil. This oil was dissolved in dry dibutylether (10 ml) and ethyl (R)-3-piperidinecarboxylate (3.7 g, 0.024 mol) and potassium carbonate (3.3 g, 0.024 mol) were added. The mixture was heated at reflux temperature for 2 h under an atmosphere of nitrogen and then stirred overnight at room temperature. Ethyl acetate (50 ml) was added, the mixture was filtered and the solvent was evaporated in vacuo. The residue was submitted to flash chromatography on silica gel (150 g) using a mixture of n-heptane and THF (4:1) as eluent. This provided 3.8 g (48% calculated from diphenylamine) of the title compound as an oil.

TLC: rf=0.22 ($SiO_2$; n-heptane/THF=7:3).

Example 2

(R)-N-(2-(2-(Diphenylamino)ethoxy)ethyl)-3-piperidinecarboxylic acid hydrochloride The ester prepared in Example 1 (3.5 g, 8.8 mmol) was dissolved in ethanol (10 ml) and a 12 N sodium hydroxide solution (1.5 ml) was added. The reaction mixture was stirred at room temperature for 5 h. A concentrated hydrochloric acid solution (2.2 ml) was added with cooling of the reaction vessel in an ice-bath and dichloromethane (300 ml) was added. The resulting emulsion was dried ($Na_2SO_4$) and the solvent evaporated in vacuo to give a residue which was crystallised from acetone. This afforded 1.5 g (43%) of the title compound.

M.P. 145–148° C.

Calculated for $C_{22}H_{28}ClN_2O_3 \cdot 1H_2O$: C, 64.9%; H, 7.2%; Cl, 8.8%; N, 6.9%; Found: C, 64.6%; H, 7.4%; Cl, 9.0%; N, 6.7%.

Example 3

(R)-N-(6-(Diphenylamino)-1-hexyl)-3-piperidinecarboxylic acid ethyl ester

A mixture of sodium hydride (0.7 g, 0.023 mol, 80% oil dispersion) and diphenylamine (3.4 g, 0.020 mol) in dry dibutylether (30 ml) was heated at reflux temperature for 1 h under an atmosphere of nitrogen. The reaction mixture was cooled and 1,6-dibromohexane (3.1 ml) was added. The mixture was heated at reflux temperature for 3 h and then cooled to 40° C. Ethyl (R)-3-piperidinecarboxylate (3.5 g, 0.022 mol) and potassium carbonate (3.1 g, 0.022 mol) were added and the mixture was heated at reflux temperature for 16 h under an atmosphere of nitrogen. Ethyl acetate (50 ml) was added, the mixture was filtered and the solvent was evaporated in vacuo. The residue was submitted to flash chromatography on silica gel (200 g) using a mixture of n-heptane and THF (4:1) as eluent. This provided 3.4 g (42% calculated from diphenylamine) of the title compound as an oil.

TLC: rf=0.26 ($SiO_2$; n-heptane/THF=7:3).

Example 4

(R)-N-(6-(Diphenylamino)-1-hexyl)-3-piperidinecarboxylic acid hydrochloride

The ester prepared in Example 3 (3.4 g, 8.3 mmol) was dissolved into ethanol (10 ml) and a 12 N sodium hydroxide solution (1.5 ml) was added. The reaction mixture was stirred at room temperature for 6 h. A concentrated hydrochloric acid solution (2.3 ml) was added with cooling of the reaction vessel in an ice-bath and dichloromethane (300 ml) was added. The resulting emulsion was dried ($Na_2SO_4$) and the solvent evaporated in vacuo to give a residue which was crystallised from ethyl acetate. This afforded 2.8 g (81%) of the title compound.

M.P. 143–146° C.

Calculated for $C_{24}H_{33}ClN_2O_2$: C, 69.1%; H, 8.0%; Cl, 8.5%; N, 6.7%; Found: C, 69.2%; H, 8.2%; Cl, 8.6%; N, 6.5%.

The compounds in Examples 5–9 were prepared by methods similar to those described in Examples 3 and 4.

Example 5
(R)-N-(3-(Diphenylamino)-1-propyl)-3-piperidinecarboxylic acid hydrochloride

M.P. 146–151° C.

Calculated for $C_{21}H_{27}ClN_2O_2$: C, 67.3%; H, 7.3%; Cl, 9.5%; N, 7.5%; Found: C, 67.1%; H, 7.4%; Cl, 9.4%; N, 7.5%.

Example 6
(R)-N-(4-(Diphenylamino)-1-butyl)-3-piperidinecarboxylic acid hydrochloride

M.P. 196–198° C.

Calculated for $C_{22}H_{29}ClN_2O_2$: C, 67.9%; H, 7.5%; Cl, 9.1%; N, 7.2%; Found: C, 67.7%; H, 7.7%; Cl, 8.9%; N, 7.0%.

Example 7
(R)-N-(5-(Diphenylamino)-1-pentyl)-3-piperidinecarboxylic acid hydrochloride

M.P. 175–178° C.

Calculated for $C_{23}H_{31}ClN_2O_2$: C, 68.2%; H, 7.8%; Cl, 8.8%; N, 6.9%; Found: C, 67.8%; H, 7.8%; Cl, 8.7%; N, 6.6%.

Example 8
(R)-N-(7-(Diphenylamino)-1-heptyl)-3-piperidinecarboxylic acid hydrochloride

M.P. 115–120° C.

Calculated for $C_{25}H_{35}ClN_2O_2$: C, 69.7%; H, 8.2%; Cl, 8.2%; N, 6.5%; Found: C, 69.5%; H, 8.3%; Cl, 8.2%; N, 6.4%.

Example 9
(R)-N-(8-(Diphenylamino)-1-octyl)-3-piperidinecarboxylic acid hydrochloride

M.P. 80–86° C.

Calculated for $C_{26}H_{37}ClN_2O_2$: C, 70.2%; H, 8.4%; Cl, 8.0%; N, 6.3%; Found: C, 69.8%; H, 8.5%; Cl, 7.8%; N, 6.2%.

Example 10
(R)-N-(4-(2-(Diphenylamino)ethoxy)-1-butyl)-3-piperidinecarboxylic acid hydrochloride 3,4-Dihydro-2H-pyran (92.5 g, 1.1 mol) was added dropwise to 2-bromoethanol (125 g, 1.0 mol) on an ice-bath. The temperature was kept between 25–30° C. during addition. When addition was complete a concentrated hydrochloric acid solution (1 ml) was added and the reaction mixture was stirred overnight at room temperature. The mixture was fractionated in vacuo to give 147 g (70%) of 2-bromoethyl-tetrahydropyran-2-yl ether.

A mixture of sodium hydride (2.0 g, 0.050 mol, 60% oil dispersion), diphenylamine (7.6 g, 0.045 mol) and dry diethylene glycol dimethyl ether (30 ml) was stirred for 3 h at 135° C. under a nitrogen atmosphere.

The reaction mixture was cooled using an ice-bath and 2-bromoethyl-tetrahydro-pyran-2-yl ether (10.5 g, 0.050 mol) and dry dibutylether (15 ml) were introduced and then the mixture was stirred for 3 h at 120° C.

The mixture was cooled, poured into water (300 ml) and extracted with ethyl acetate (2×200 ml). The combined organic extracts was dried ($Na_2SO_4$) and the solvent was evaporated in vacuo. The residue was dissolved in isopropanol (150 ml) and a 4 N sulfuric acid solution (30 ml) was added. The mixture was stirred at 60° C. for 30 minutes and the pH was adjusted to 7 with a 4 N sodium hydroxide solution. The neutralised mixture was poured into water (1 l) and extracted with ethyl acetate (2×250 ml). The combined organic extracts was dried ($Na_2SO_4$) and the solvent was evaporated in vacuo. The residue was submitted to flash chromatography on silica gel (200 g) using a mixture of n-heptane and THF (4:1) as eluent. This afforded 5.4 g (56%) of 2-(diphenylamino)ethanol.

Sodium hydride (0.4 g, 10.0 mmol, 60% oil dispersion) was suspended in dry dibutylether (25 ml) and under an atmosphere of nitrogen 2-(diphenylamino)ethanol (2.1 g, 10.0 mmol) was added. The mixture was stirred for 1 h at room temperature and then heated at 130° C. for 1 h. Lithium hydride (0.1 g) was added and the mixture was heated at reflux temperature for 1 h. The mixture was cooled to 80° C. and 1-bromo-4-chlorobutane (2.0 g, 11.7 mmol) was added. The reaction mixture was heated at reflux temperature for 12 h and then another portion of 1-bromo-4-chlorobutane (4.0 g, 23.4 mmol) was added. Heating was continued for further 24 h. Dibutylether (25 ml) was added to the cooled reaction mixture and then water (25 ml) was added carefully. The organic phase was separated, dried over potassium carbonate and the solvent was evaporated in vacuo. The residue was submitted to flash chromatography on silica gel (100 g) using a mixture of n-heptane and THF (4:1) as eluent. This afforded 2.0 g of 1-chloro-4-(2-(diphenylamino)ethoxy)butane.

A mixture of 1-chloro-4-(2-(diphenylamino)ethoxy)butane (2.0 g, 6.6 mmol), ethyl (R)-3-piperidinecarboxylate (1.1 g, 7.0 mmol), potassium carbonate (1.0 g, 7.2 mmol) and dry dibutylether was heated at 150° C. for 4 h. The mixture was cooled, filtered and the solvent evaporated in vacuo. The residue was submitted to flash chromatography on silica gel (150 g) using a mixture of n-heptane and THF (4:1) as eluent. This afforded 1.5 g (34% calculated from 2-(diphenylamino)ethanol) of (R)-N-(4-(2-(diphenylamino)ethoxy)-1-butyl)-3-piperidinecarboxylic acid ethyl ester as an oil.

TLC: rf=0.23 ($SiO_2$; n-heptane/THF=7:3).

(R)-N-(4-(2-(Diphenylamino)ethoxy)-1-butyl)-3-piperidinecarboxylic acid ethyl ester (1.5 g, 3.5 mmol) was dissolved into ethanol (10 ml) and a 12 N sodium hydroxide solution (0.85 ml) was added. The reaction mixture was stirred at room temperature for 3 h. A concentrated hydrochloric acid solution (1.7 ml) was added with cooling of the reaction vessel in an ice-bath and dichloromethane (300 ml) was added. The resulting emulsion was dried ($Na_2SO_4$) and the solvent evaporated in vacuo to give a residue which was crystallised from acetone. This afforded 1.1 g (73 %) of the title compound.

HPLC retention time=26.9 minutes (system A).

Calculated for $C_{24}H_{33}ClN_2O_3$: C, 66.6%; H. 7.7%; Cl, 8.2%; N, 6.5%; Found: C, 66.6%; H, 7.7%; Cl, 8.4%; N, 6.3%.

The compounds in Examples 11–14 were prepared by a method similar to that described in Example 10.

Example 11
(R)-N-(3-(3-Diphenylamino-1-propyloxy)-1-propyl)-3-piperidinecarboxylic acid hydrochloride

M.P. 138–140° C.

Calculated for $C_{24}H_{33}ClN_2O_3$: C, 66.6%; H, 7.7%; Cl, 8.2%; N, 6.5%; Found: C, 66.9%; H, 7.8%; Cl, 8.2%; N, 6.4%.

Example 12
(R)-N-(2-(4-Diphenylamino-1-butyloxy)ethyl)-3-piperidinecarboxylic acid hydrochloride HPLC retention time=27.0 minutes (system A).

Example 13
(R)-1-(2-((2-((3-Methylphenyl)(phenyl)amino)ethoxy)ethyl)-3-piperidinecarboxylic acid hydrochloride HPLC retention time=18.0 minutes (system D).

Example 14
R)-1-(2-(2-((3-Chlorophenyl)(phenyl)amino)ethoxy)ethyl)-3-piperidinecarboxylic acid hydrochloride HPLC retention time=19.2 minutes (system D).

Example 15
(R)-N-(2-(3,3-Diphenyl-1-propyloxy)ethyl)-3-piperidinecarboxylic acid ethyl ester A mixture of sodium hydride (0.80 g, 0.020 mol, 60% oil dispersion) and 3,3-diphenyl-1-propanol (4.25 g, 0.020 mol) in dry dibutylether (30 ml) was stirred at room temperature for 30 minutes and then heated at reflux temperature for 2.5 h under an atmosphere of nitrogen. The reaction mixture was cooled to 60° C. and 2-bromoethyltetrahydro-2-pyranyl ether (4.2 g, 0.020 mol) was added. The mixture was heated at reflux temperature for 16 h under an atmosphere of nitrogen. The reaction mixture was cooled, washed with water and the organic solvent was evaporated in vacuo. Column chromatography of the residue on silica gel (150 g) using a mixture of n-heptane and THF (4:1) as eluent provided 2.6 g of an oil, which was dissolved in isopropanol (25 ml). A 4 N sulfuric acid solution (10 ml) was added and the mixture was stirred at 60 C for 1 h. Dichloromethane (250 ml) was introduced and the separated organic phase was washed with water (2×100 ml) and a 5% sodium bicarbonate solution (100 ml). The organic phase was dried ($Na_2SO_4$) and the solvent was evaporated in vacuo to give 2.5 g (49%) of 2-(3,3-diphenyl-1-propyloxy)ethanol as an oil.

A solution of 2-(3,3-diphenyl-1-propyloxy)ethanol (2.5 g, 0.010 mol) in dry THF (20 ml) was placed on an ice-bath and a solution of n-butyllithium in hexanes (4.0 ml, 2.5 M) was added dropwise under an atmosphere of nitrogen. When addition was complete the reaction mixture was stirred at room temperature for 0.5 h and then heated at reflux temperature for 1 h. The mixture was cooled to room temperature and p-toluenesulphonyl chloride (2.1 g, 0.011 mol) was added. The mixture was stirred at room temperature for 0.5 h and then heated at reflux temperature for 1 h. To the cooled reaction mixture was added dry potassium carbonate (2.0 g, 0.015 mol) and ethyl (R)-3-piperidinecarboxylate (2.0 g, 0.0125 mol) and the mixture was heated at reflux temperature for 3 h. The cooled reaction mixture was poured into water (200 ml) and extracted with ethyl acetate (2×200 ml). The combined organic extracts was dried ($Na_2SO_4$) and the solvent evaporated in vacuo. The residue was submitted to flash chromatography on silica gel (150 g) using a mixture of n-heptane and THF (4:1) as eluent. This provided 0.9 g (11% calculated from 3,3-diphenyl-1-propanol) of the title compound as an oil.

TLC: rf=0.24 ($SiO_2$; n-heptane/THF=7:3).

$^1$H NMR ($CDCl_3$) δ 4.10 (t, 1H).

Example 16
(R)-N-(2-(3,3-Diphenyl-1-propyloxy)ethyl)-3-piperidinecarboxylic acid hydrochloride The ester prepared in Example 15 (0.9 g, 2.3 mmol) was dissolved in ethanol (10 ml) and a 12 N sodium hydroxide solution (0.6 ml) was added. The reaction mixture was stirred at room temperature for 4 h. Concentrated hydrochloric acid solution (0.7 ml) was added with cooling of the reaction vessel in an ice-bath and dichloromethane (300 ml) was added. The resulting emulsion was dried ($Na_2SO_4$) and the solvent evaporated in vacuo to give an oily residue which was crystallised from acetone. This afforded 0.5 g (54%) of the title compound.

M.P. 178–179° C.

Calculated for $C_{23}H_{30}ClNO_3$: C, 68.4%; H, 7.5%; Cl, 8.8%; N, 3.5%; Found: C, 67.9%; H, 7.5%; Cl, 8.8%; N, 3.3%;

$^1$H NMR (DMSO-$d_6$) δ 4.12 (t, 1H).

Example 17
N-(2-(3,3-Diphenyl-1-propyloxy)ethyl)-1,2,5,6-tetrahydro-3-pyridinecarboxylic acid ethyl ester A solution of n-butyllithium in hexanes (20 ml, 2.5 M) was added drop-wise under a nitrogen atmosphere to dry ethylene glycol (40 ml) at 10° C. When addition was complete the mixture was stirred for 0.5 h at room temperature. 3-Bromo-1,1-diphenyl-1-propene (13.7 g, 50 mmol, prepared similarly to the method described in Example 26) was added and the reaction mixture was stirred at room temperature for 48 h. The mixture was poured into water (100 ml) and extracted with ethyl acetate (2×100 ml). The combined organic extracts was dried ($Na_2SO_4$) and the solvent evaporated in vacuo. Flash chromatography of the residue on silica gel (150 g) using a mixture of cyclohexane and ethyl acetate (7:3) as eluent provided 6.2 g (48%) of 2-(3,3-diphenyl-3-propen-1-yloxy)ethanol.

2-(3,3-Diphenyl-3-propen-1-yloxy)ethanol (4.0 g, 15.7 mmol) was dissolved in dry dioxan (80 ml) and stirred under an atmosphere of hydrogen for 3 h at room temperature in the presence of 10% palladium on carbon catalyst (50% aqueous paste) and then filtered. The solvent was evaporated in vacuo to give 4.0 g (100%) of 2-(3,3-diphenyl-1-propyloxy)ethanol. A solution of 2-(3,3-diphenyl-1-propyloxy)ethanol (3.9 g, 15 mmol) in dry THF (30 ml) kept under a nitrogen atmosphere was cooled to 10° C. and a solution of n-butyl-lithium in hexanes (6.0 ml, 2.5 M) was added dropwise. The reaction mixture was stirred for 1 h at room temperature and heated at reflux temperature for 1.5 h and then cooled to room temperature. p-Toluenesulphonyl chloride (2.9 g, 15 mmol) was added and the mixture was stirred at room temperature for 1.5 h. Ethyl 1,2,5,6-tetrahydro-3-pyridinecarboxylate hydrochloride (3.8 g, 20 mmol) and potassium carbonate (5.0 g, 38 mmol) were added and the mixture was stirred at room temperature for 0.5 h and then heated at reflux temperature for 4 h. The reaction mixture was allowed to stand overnight and was diluted with ice water (25 ml) and ethyl acetate (100 ml). The separated organic phase was extracted with a 10% citric acid solution (4×50 ml) and the combined aqueous extracts was washed with ethyl acetate (25 ml). The acidic aqueous phase was adjusted to pH 5 with a sodium bicarbonate solution and extracted with ethyl acetate. The organic extract was washed with a diluted sodium bicarbonate solution, dried ($Na_2SO_4$) and the solvent evaporated in vacuo to give 1.9 9 (32%) of the title compound as an oil.

TLC: rf=0.21 ($SiO_2$; n-heptane/THF=7:3).

$^1$H NMR ($CDCl_3$) δ 4.12 (t, 1H); 7.00 (m, 1H).

Example 18
N-(2-(3,3-Diphenyl-1-propyloxy)ethyl)-1,2,5,6-tetrahydro-3-pyridinecarboxylic acid hydrochloride The ester prepared in Example 17 (1.9 g, 4.8 mmol) was dissolved in ethanol (10 ml) and a 12 N sodium hydroxide solution (1.0 ml) was added. The reaction mixture was stirred at room temperature for 5 h. A concentrated hydrochloric acid solution (1.5 ml) was added with cooling of the reaction vessel in an ice-bath and dichloromethane (500 ml) was added. The resulting emulsion was dried ($Na_2SO_4$) and the solvent evaporated in vacuo to give an oily residue which was stripped twice with acetone and crystallised from ethyl acetate. This afforded 1.5 g (78%) of the title compound as a crystalline solid.

M.P. 155–156° C.

Calculated for $C_{23}H_{28}ClNO_3$: C, 68.7%; H, 7.0%; Cl, 8.8%; N, 3.5% Found: C, 68.2%; H, 7.2%; Cl, 8.8%; N, 3.4%.

¹H NMR (DMSO-d₆) δ 4.13 (t, 1H); 7.02 (m, 1H).

The compound in Example 19 was prepared by a method similar to that described in Examples 17 and 18.

Example 19
(R)-1-(2-(3,3-Bis(4-fluorophenyl)-1-propyloxy)ethyl)-3-piperidinecarboxylic acid hydrochloride

M.P. 154–156° C.

Calculated for $C_{23}H_{28}ClF_2NO_3$: C, 62.8%; H, 6.4%; N, 3.2%; Found: C, 62.8%; H, 6.6%; N, 2.9%.

Example 20
(R)-N-(2-(3-Phenyl-3-(3-(trifluoromethyl)phenyl)-1-propyloxy)ethyl)-3-piperidinecarboxylic acid ethyl ester A solution of n-butyllithium in hexanes (16 ml, 2.5 M) was added drop-wise under a nitrogen atmosphere to dry ethylene glycol (40 ml) at 10° C. When addition was complete the mixture was stirred for 0.5 h at room temperature. 3-Bromo-1-phenyl-1-(3-(trifluoromethyl)phenyl)-1-propene (12.0 g, 35 mmol, prepared similarly to the method described in Example 26) was added and the reaction mixture was stirred at room temperature for 72 h. The mixture was poured into water (300 ml) and extracted with ethyl acetate (2×100 ml). The combined organic extracts was dried ($Na_2SO_4$) and the solvent evaporated in vacuo. Flash chromatography of the residue on silica gel (150 g) using a mixture of cyclohexane and ethyl acetate (7:3) as eluent provided 5.9 g (52%) of 2-(3-phenyl-3-(3-(trifluoromethyl)phenyl)-2-propen-1-yloxy)-ethanol. 2-(3-phenyl-3-(3-(trifluoromethyl)phenyl)-2-propen-1-yloxy)ethanol (5.0 g, 15.5 mmol) was dissolved into dry dioxan (80 ml) and stirred under an atmosphere of hydrogen for 18 h at room temperature in the presence of 10% palladium on carbon catalyst (50% aqueous paste) and then filtered. The filtrate was evaporated in vacuo to give 4.0 g (95%) of 2-(3-phenyl-3-(3trifluoromethyl)phenyl)-1-propyloxy)ethanol.

¹H NMR (CDCl₃) δ 4.20 (t, 1H).

A solution of 2-(3-phenyl-3-(3-trifluoromethyl)phenyl)1-propyloxy)ethanol (4.8 g, 15 mmol) in dry THF (35 ml) kept under a nitrogen atmosphere was cooled to 10° C. and a solution of n-butyllithium in hexanes (6.0 ml, 2.5 M) was added dropwise. The reaction mixture was stirred for 0.5 h at room temperature, heated at reflux temperature for 1 h and cooled to room temperature. p-Toluenesulphonyl chloride (2.9 g, 15 mmol) was added and the mixture was heated at reflux temperature for 1.5 h and then cooled to room temperature. Ethyl (R)-3-piperidinecarboxylate (3.2 g, 20 mmol) and potassium carbonate (2.8 g, 20 mmol) were added and the mixture was heated at reflux temperature for 4.5 h. The reaction mixture was diluted with ice water (100 ml) and ethyl acetate (150 ml). The separated organic phase was washed with a diluted sodium bicarbonate solution, dried ($Na_2SO_4$) and the solvent evaporated in vacuo. Flash chromatography of the residue on silica gel (100 g) using a mixture of cyclohexane and ethyl acetate (7:3) as eluent provided 2.4 g (35%) of the title compound as an oil.

TLC: rf=0.11 (SiO₂; cyclohexane/ethyl acetate=7:3).
¹H NMR (CDCl₃) δ 4.20 (t, 1H).

Example 21
(R)-N-(2-(3-Phenyl-3-(3-(trifluoromethyl)phenyl)-1-propyloxy)ethyl)-3-piperidinecarboxylic acid hydrochloride The ester prepared in Example 20 (2.4 g, 5.2 mmol) was dissolved in ethanol (10 ml) and a 12 N sodium hydroxide solution (1.1 ml) was added. The reaction mixture was stirred at room temperature for 4 h. A concentrated hydrochloric acid solution (1.6 ml) was added with cooling on an ice-bath and dichloromethane (400 ml) was added. The resulting emulsion was dried ($Na_2SO_4$) and the solvent evaporated in vacuo to give an oily residue which was stripped twice with acetone and dissolved in toluene (50 ml). The organic solution was extracted with water (2×50 ml) and the combined aqueous extracts was washed with ethyl acetate (2×25 ml). Water was evaporated from the aqueous phase in vacuo to give a residue which was stripped with dichloromethane. This afforded 0.8 g (33%) of the title compound as an amorphous solid.

HPLC retention time=11.4 minutes (system A).

Calculated for $C_{24}H_{29}ClF_3NO_3,H_2O$: C, 58.8%; H, 6.4%; Cl, 7.5%; N, 2.9% Found: C, 58.6%; H, 6.5%; Cl, 7.5%; N, 2.7%;

¹H NMR (DMSO-d₆) δ 4.30 (dt, 1H).

Example 22
(R)-N-(2-(3,3-Bis(4-Chlorophenyl)-1-propyloxy)ethyl)3-piperidinecarboxylic acid ethyl ester 2-(3,3-Bis(4-Chlorophenyl)-2-propen-1-yloxy)ethanol (4.5 g, 14.0 mmol, prepared as described in Example 38) was dissolved in dry dioxan (50 ml) and stirred under an atmosphere of hydrogen for 18 h at room temperature in the presence of 10% palladium on carbon catalyst (50% aqueous paste) and then filtered. The solvent was evaporated in vacuo to give an oil which was submitted to flash chromatography on silica gel (100 g) using a mixture of cyclohexane/ethyl acetate (6:4) as eluent. This afforded 3.5 g (78%) of 2-(3, 3bis(4-chlorophenyl)-1-propyloxy)ethanol.

TLC: rf=0.40 (SiO₂; n-heptane/ethyl acetate=3:7).
¹H NMR (CDCl₃) δ 4.08 (t, 1H).

A solution of 2-(3,3-bis(4-chlorophenyl)-1-propyloxy) ethanol (3.5 g, 10.8 mmol) in dry THF (25 ml) kept under a nitrogen atmosphere was cooled to 10° C. and a solution of n-butyllithium in hexanes (4.3 ml, 2.5 M) was added dropwise. When addition was complete the reaction mixture was stirred for 1 h at room temperature. p-Toluenesulphonyl chloride (2.1 g, 10.8 mmol) was added and the mixture was stirred at room temperature for 1.5 h. The solvent was evaporated in vacuo and acetone (30 ml) was added to the residue. The mixture was filtered and to the filtrate was added ethyl (R)-3-piperidinecarboxylate (1.8 g, 11.5 mmol) and potassium carbonate (1.5 g, 10.8 mmol). The mixture was heated at reflux temperature for 3 h and then stirred for 2 days at room temperature. The reaction mixture was filtered and the solvent was evaporated in vacuo.

Column chromatography of the residue on silica gel (200 g) using a mixture of n-heptane and ethyl acetate (6:4) as eluent provided 2.0 g (40 %) of the title compound as an oil.

TLC: rf=0.17 (SiO₂; n-heptane/ethyl acetate=7:3).
¹H NMR (CDCl₃) δ 4.13 (t, 1H).

Example 23
(R)-N-(2-(3,3-Bis(4-Chlorophenyl)-1-propyloxy)ethyl)-3-piperidinecarboxylic acid hydrochloride The ester prepared in Example 22 (1.9 g, 4.0 mmol) was dissolved in ethanol (15 ml) and a 4 N sodium hydroxide solution (3.0 ml) was added. The reaction mixture was stirred at room temperature for 4 h. A concentrated hydrochloric acid solution (1.5 ml) was added with cooling on an ice-bath and dichloromethane (400 ml) was added. The phases were separated and the organic phase was dried ($Na_2SO_4$). The solvent was evaporated in vacuo to give an oily residue which was stripped twice with acetone and crystallised from ethyl acetate. This afforded 1.4 g (74 %) of the title compound as a crystalline material.

M.P. 165–167° C.

HPLC retention time=13.7 minutes (system A);
¹H NMR (DMSO-d₆) δ 4.20 (t, 1H).

Example 24
(R)-N-(2-(3,3-Diphenyl-2-propen-1-yloxy)ethyl)-3-piperidinecarboxylic acid ethyl ester To a well-stirred solution of propiophenone (20.1 g, 0.15 mol) in dry diethyl ether (125 ml) kept under nitrogen at room temperature was added a solution of phenylmagnesium bromide (55 ml, 3 M in diethyl ether) in dry diethyl ether (25 ml). The reaction mixture was stirred for 1 h and a mixture of a saturated ammonium chloride solution (100 ml) and water (50 ml) was added. The phases were separated and the aqueous phase was extracted with diethyl ether (100 ml). The combined organic phases was washed with a 0.5 N hydrochloric acid solution and dried ($Na_2SO_4$). The solvent was evaporated in vacuo to give a solid residue which was triturated with cyclohexane (100 ml). The solid was collected by filtration and dried to give 26.4 g (83%) of 1,1-diphenyl-1-propanol.

A mixture of 1,1-diphenyl-1-propanol (64 g, 0.30 mol), isopropanol (300 ml) and a 5 N solution of sulphuric acid (150 ml) was heated at reflux temperature for 18 h. The reaction mixture was cooled, diluted with water (600 ml) and extracted with toluene (3×150 ml). The combined organic phases was dried ($Na_2SO_4$) and the solvent was evaporated in vacuo to give a solid residue which was triturated with iso-octane. The solid was collected by filtration to give 28.8 g (49%) of 1,1-diphenyl-1-propene.

A mixture of 1,1-diphenyl-1-propene (17.0 g, 0.10 mol), carbontetrachloride (100 ml), benzoylperoxide (0.2 g) and N-bromosuccinimide (17.8 g, 0.10 mol) was heated at reflux temperature for 18 h. The reaction mixture was allowed to cool to room temperature, filtered and the solvent was evaporated in vacuo to give 3-bromo-1, 1-diphenyl-1-propene in a quantitative yield.

A solution of n-butyllithium in hexanes (7.3 ml, 2.5 M) was added drop-wise under a nitrogen atmosphere to ethylene glycol (20 ml) at 10° C. When addition was complete the mixture was stirred for 0.5 h at room temperature. 3-Bromo-1,1-diphenyl-1-propene (5.0 g, 18.3 mmol) was added and the reaction mixture was stirred at room temperature for 1 h, at 80° C. for 0.5 h and finally at room temperature for 3 h. Water (100 ml) was added and the mixture was extracted with ethyl acetate (100 ml). The phases were separated and the organic phase was washed with water (2×50 ml), dried ($Na_2SO_4$) and the solvent was evaporated in vacuo. Flash chromatography of the residue on silica gel (150 g) using n-heptane and THF (4:1) as eluent provided 2.9 g (62%) of 2-(3,3-diphenyl-2-propen-1-yloxy)ethanol.

A solution of 2-(3,3-diphenyl-2-propen-1l-yloxy)ethanol (3.0 g, 11.8 mmol) in dry THF (30 ml) kept under a nitrogen atmosphere was cooled to 10° C. and a solution of n-butyllithium in hexanes (5.0 ml, 2.5 M) was added dropwise. The reaction mixture was stirred for 0.5 h at room temperature and p-toluenesulphonyl chloride (2.3 g, 12.1 mmol) was added. The mixture was stirred at room temperature for 1 h. Ethyl (R)-3-piperidinecarboxylate (2.7 g, 17.7 mmol) and potassium carbonate (2.5 g, 17.7 mmol) were added and the mixture was heated at reflux temperature for 5 h. The cooled reaction mixture was poured into water (100 ml) and extracted with ethyl acetate (2×75 ml). The combined organic phases was washed with water and a sodium citrate buffer solution (2×100 ml, pH 6). The organic phase was then extracted with a 5% citric acid solution (3×75 ml) and the combined acidic aqueous extracts was washed with ethyl acetate (25 ml). To the acidic aqueous solution was added a 4 N sodium hydroxide solution until pH 11 and this solution was immediately extracted with ethyl acetate (3×50 ml). The combined organic extracts was dried ($Na_2SO_4$) and the solvent evaporated in vacuo to give 1.5 g (33%) of the title compound as an oil.

TLC: rf=0.20 ($SiO_2$; n-heptane/THF=7:3);
$^1$H NMR ($CDCl_3$) δ 4.08 (d, 2H); 6.22 (t, 1H).

Example 25
(R)-N-(2-(3,3-Diphenyl-2-propen-1-yloxy)ethyl)-3-piperidinecarboxylic acid hydrochloride The ester prepared in Example 24 (1.4 g, 3.6 mmol) was dissolved in ethanol (10 ml) and a 12 N sodium hydroxide solution (0.9 ml) was added. The reaction mixture was stirred at room temperature for 3.5 h. A concentrated hydrochloric acid solution (2.0 ml) was added with cooling on an ice-bath and dichloromethane (250 ml) was added. The resulting emulsion was dried ($Na_2SO_4$) and the solvent evaporated in vacuo to give an oily residue which was agitated with acetone. This afforded 0.85 g (60%) of the title compound as a crystalline solid.

M.P. 160–165° C.
HPLC retention time=16.6 minutes (system A).
$^1$H NMR (DMSO-$d_6$) δ 4.03 (d, 2H); 6.22 (t, 1H).

Example 26
(R)-N-(2-(3-(2-Methylphenyl)-3-phenyl-2-propen-1-yloxy)ethyl)-3-piperidinecarboxylic acid hydrochloride Propiophenone (6.7 g, 50 mmol) was added dropwise to a solution of 2-methylphenylmagnesium chloride (30 ml of a 2.0 M solution in diethyl ether) and dry THF (50 ml) under a nitrogen atmosphere. When the addition was complete the reaction mixture was heated at reflux temperature for 5 h. Excess of a saturated ammonium chloride solution was added and the mixture was extracted with diethyl ether (2×100 ml). The combined organic extracts were dried over potassium carbonate and the solvent was evaporated in vacuo to give 10.4 g (92%) of 1-(2-methyl phenyl)-1-phenyl-1-propanol.

TLC: rf=0.50 ($SiO_2$; n-heptane/THF=7:3). 1-(2-Methylphenyl)-1-phenyl-1-propanol (10.4 g, 46 mmol) was dissolved into isopropanol (100 ml) and a 4 N sulphuric acid solution (50 ml) was added. The reaction mixture was heated at reflux temperature for 18 h and cooled to room temperature. Water (300 ml) was added and the mixture was extracted with dichloromethane (2×200 ml). The combined organic extracts was washed with a diluted sodium bicarbonate solution, dried ($Na_2SO_4$) and the solvent evaporated in vacuo to give 9.0 g (91%) of 1-(2-methylphenyl)-1-phenyl-1-propene. To a solution of 1-(2-methylphenyl)-1-phenyl-1-propene (9.0 g, 43 mmol) in carbon-tetrachloride (40 ml), N-bromosuccinimide (7.7 g, 43 mmol) and benzoylperoxide (0.1 g) were added. The reaction mixture was heated at reflux temperature for 18 h. The cooled reaction mixture was filtered through silica gel and the solvent evaporated in vacuo to give 9.3 g (76 %) of 3-bromo-1 (2-methylphenyl)-1-phenyl-1-propene.

A solution of n-butyllithium in hexanes (13.0 ml, 2.5 M) was added dropwise under a nitrogen atmosphere to ethylene glycol (30 ml) at 10° C. When addition was complete the mixture was stirred 0.5 h at room temperature. 3-Bromo-1-(2-methylphenyl)-1-phenyl-1-propene (9.3 g, 32 mmol) was added and the reaction mixture was stirred at room temperature for 100 h. The mixture was poured into water (200 ml) and extracted with ethyl acetate (3×75 ml). The combined organic extracts was dried ($Na_2SO_4$) and the solvent evaporated in vacuo. Flash chromatography of the residue on silica gel (200 g) using a mixture of n-heptane and THF (4:1) as eluent provided 3.9 g (45%) of 2-(3-(2-methylphenyl)-3-phenyl-2-propen-1-yloxy)ethanol.

TLC: rf=0.20 ($SiO_2$; n-heptane/THF=7:3).

A solution of 2-(3-(2-methylphenyl)-3-phenyl-2-propen-1-yloxy)ethanol (3.4 g, 12.5 mmol) in dry THF (30 ml) kept under a nitrogen atmosphere was cooled to 10° C. and a solution of n-butyllithium in hexanes (5.5 ml, 2.5 M) was added dropwise. The reaction mixture was stirred for 0.5 h at room temperature and p-toluenesulphonyl chloride (2.6 g, 13.8 mmol) was added. The mixture was stirred at room temperature for 1.5 h. Ethyl (R)-3-piperidinecarboxylate (2.9 g, 18.8 mmol) and potassium carbonate (2.6 g, 18.8 mmol) were added and the mixture was heated at reflux temperature for 18 h. The cooled reaction mixture was poured into ice water (200 ml) and extracted with ethyl acetate (2×100 ml). The combined organic extracts was washed with a 10% sodium citrate buffer solution (2×100 ml, pH 6). The organic phase was extracted with a 5% citric acid solution (4×75 ml) and the combined acidic aqueous extracts was washed with toluene (50 ml). To the acidic aqueous solution was added a 4 N sodium hydroxide solution until pH 9 and this solution was immediately extracted with ethyl acetate (2×100 ml). The combined organic extracts was dried ($Na_2SO_4$) and the solventevaporated in vacuo to give 2.3 g (45%) of (R)-N-(2-(2-(2-methylphenyl)-3-phenyl-2-propen-1-yloxy)ethyl)3-piperidinecarboxylic acid ethyl ester as an oil.
TLC: rf=0.23 ($SiO_2$; n-heptane/THF=7:3).
(R)-N-(2-(3-(2-Methylphenyl)-3-phenyl-2-propen-1-yloxy)ethyl)-3-piperidinecarboxylic acid ethyl ester (2.3 g, 5.6 mmol) was dissolved in ethanol (10 ml) and a 12 N sodium hydroxide solution (1.4 ml) was added. The reaction mixture was stirred at room temperature for 4 h. A concentrated hydrochloric acid solution was added with cooling of the reaction vessel in an ice-bath until pH 1 and dichloromethane (250 ml) was added. The resulting emulsion was dried ($Na_2SO_4$) and the solvent was evaporated in vacuo to give a residue which was crystallised from acetone. This afforded 1.75 g (76%) of the title compound.
M.P. 145–150° C.
Calculated for $C_{24}H_{30}ClNO_3$: C, 69.3%; H, 7.3%; Cl, 8.5%; N, 3.4% Found: C, 69.0%; H, 7.4%; Cl, 8.5%; N, 3.4%;
$^1$H NMR (DMSO-$d_6$) δ 3.86 (d, 2H); 6.42 (t, 1H).

Example 27

(R)-N-(2-(3-(2-Methylphenyl)-3-phenyl-1-propyloxy) ethyl)-3-piperidinecarboxylic acid hydrochloride The acid prepared in Example 26 (1.0 g, 2.4 mmol) was dissolved in methanol (20 ml) and stirred under an atmosphere of hydrogen for 1 h at room temperature in the presence of 10% palladium on carbon catalyst (50% aqueous paste) and then filtered. The filtrate was evaporated to dryness leaving a residue which was treated with ethyl acetate to give 0.8 g (80%) of the title compound as a solid.
M.P. 137–140° C.
HPLC retention time=17.1 minutes (system A).
$^1$H NMR (DMSO-$d_6$) δ 4.30 (t, 1H).

Example 28

(R)-N-(2-(3,3-Bis(4-(Trifluoromethyl)phenyl)-2-propen-1-yloxy)ethyl)-3-piperidinecarboxylic acid A solution of n-butyllithium in hexanes (34.2 ml, 2.5 M) was added dropwise under a nitrogen atmosphere to ethylene glycol (8 ml) below 15° C. When addition was complete the mixture was stirred for 1 h at room temperature. A solution of 3-bromo-1,1-bis(4-(trifluoromethyl)phenyl)-1-propene (35 g, 0.086 mol, prepared similarly to the method described in Example 26) in toluene (40 ml) was added and the reaction mixture was stirred at room temperature for 60 h and then at 55° C. for 36 h. Water (300 ml) was added to the cooled reaction mixture and the mixture was extracted with ethyl acetate (250+50 ml). The combined organic extracts was washed with brine and dried ($Na_2SO_4$). The solvent was evaporated in vacuo to give a residue which was stripped with methanol and dichloromethane sucessively. This afforded 33.1 g (99%) of 2-(3,3-bis(4-(trifluoromethyl)-phenyl)-2-propen-1-yloxy)ethanol.
TLC: rf=0.50 ($SiO_2$; dichloromethane/methanol=19:1).
A mixture of 2-(3,3-bis(4-(trifluoromethyl)phenyl)-2-propen-1-yloxy)ethanol (25.0 g, 64 mmol) and triethylamine (16.2 g, 0.16 mol) in dry toluene (100 ml) kept under a nitrogen atmosphere was cooled to 10° C. and a solution of methanesulphonyl chloride (14.6 g, 0.13 mol) in dry toluene (100 ml) was added dropwise keeping the temperature below 10° C. When addition was complete the reaction mixture was stirred for 45 minutes at 5° C. and then for 30 minutes at 15° C. Water was added (100 ml) and the mixture was stirred at room temperature for 15 minutes. The phases were separated and the aqueous phase was extracted with two small portions of toluene. The combined organic extracts was washed with brine, dried ($Na_2SO_4$) and filtered. To the filtrate was added ethyl (R)-3-piperidine carboxylate (20.1 g, 0.13 mol) and potassium carbonate (22.1 g, 0.16 mol) and the mixture was heated at reflux temperature for 2 days and then stirred at room temperature for 2 days. The reaction mixture was filtered and the solvent evaporated in vacuo to give a residue which was dissolved into a mixture of ethyl acetate (125 ml) and water (75 ml). A 10% citric acid solution was added until pH 4 and the phases were separated. The organic phase was evaporated in vacuo to give a residue which was dissolved in toluene (150 ml). A mixture of a 34% citric acid solution (56 ml) and water (150 ml) was added and the phases were separated. The organic phase was extracted once more with a mixture of a 34% citric acid solution (20 ml) and water (50 ml). To the combined aqueous extracts was added ethyl acetate (150 ml) and excess of a 5% aqueous sodium bicarbonate solution. The phases were separated, the organic phase was dried ($Na_2SO_4$) and the solvent evaporated in vacuo to give 21.7 g (64%) of (R)-N-(2-(3,3-bis(4-(trifluoromethyl)phenyl)-2-propen-1-yloxy)ethyl)3-piperidinecarboxylic acid ethyl ester as an oil.
TLC: rf=0.60 ($SiO_2$; dichloromethane/methanol/acetic acid=20:2:1).
(R)-N-(2-(3,3-bis(4-(trifluoromethyl)phenyl)-2-propen 1-yloxy)ethyl)-3-piperidinecarboxylic acid ethyl ester (2.0 g, 3.8 mmol) was dissolved in ethanol (30 ml) and a 1 M sodium hydroxide solution (17 ml) was added. The reaction mixture was stirred at room temperature for 3 h. The solvent was evaporated in vacuo and dichloromethane (100 ml) was added. A concentrated hydrochloric acid solution was added (1.9 ml) and the phases were separated. Ethyl acetate was added to the organic phase which was then dried ($Na_2SO_4$). The solvent was evaporated in vacuo to give 2.0 g (99%) of the title compound as a solid.
HPLC retention time=7.8 minutes (system C).
$^1$H NMR (DMSO-$d_6$) δ 4.07 (d, 2H); 6.50 (t, 1H).

Example 29

(R)-N-(2-(3,3-Bis(4-(Trifluoromethyl)phenyl)-1-propyloxy)ethyl)-3-piperidinecarboxylic acid hydrochloride The acid prepared in Example 28 (1.6 g, 3.0 mmol) was dissolved in methanol (45 ml) and stirred under an atmosphere of hydrogen for 1 h at room temperature in the presence of 10% palladium on carbon catalyst (35% aqueous paste) and then filtered. The filtrate was evaporated to dryness leaving a residue which was stripped several times with diethyl ether to give 1.6 g (97%) of the title compound as a solid.

HPLC retention time=6.9 minutes (system C).

$^1$H NMR (DMSO-d$_6$) δ 4.44 (t, 1H).

Example 30

(R)-N-(2-(3-(3-Methoxyphenyl)-3-(2-methylphenyl)-2-propen-1-yloxy)-ethyl)-3-piperidinecarboxylic acid hydrochloride A solution of ethyl magnesium bromide in diethyl ether (58 ml, 3 M) was added dropwise at room temperature to a mixture of 3-methoxybenzonitrile (21.2 g, 0.159 mol) and dry THF (250 ml). When addition was complete the mixture was stirred for 1 h at room temperature, 3 h at 40° C. and finally stirred overnight at room temperature. Water (250 ml) was added followed by a saturated ammonium chloride solution (250 ml) and the mixture was stirred for 1 h at room temperature. The phases were separated and the aqueous phase was extracted with ethyl acetate (100 ml). The combined organic phases was dried (MgSO$_4$) and the solvent evaporated in vacuo to give 25.9 g (99%) of 3-methoxypropiophenone.

To a solution of 2-methylphenyl magnesium bromide (prepared from 4.9 g magnesium turnings and 24 ml of 2-bromotoluene) in dry THF (300 ml) was added dropwise a solution of 3-methoxypropiophenone (25.9 g, 0.16 mol) in dry THF (200 ml). When addition was complete the mixture was heated at reflux temperature for 2 h. Water (250 ml) was added followed by a saturated ammonium chloride solution (250 ml)and the mixture was left overnight. A 4 N hydrochloric acid solution was added until a clear solution was obtained and the phases were separated. The organic phase was dried (MgSO$_4$) and the solvent evaporated in vacuo. The residue was submitted to flash chromatography on silica gel (690 g) using a gradient of n-heptane in ethyl acetate to give 28.2 g (55%) of 1-(3-methoxy-phenyl)-1-(2-methylphenyl)-1-propanol.

A mixture of 1-(3-methoxyphenyl)-1-(2-methylphenyl)-1-propanol (26.2 g, 0.10 mol), isopropanol (300 ml) and a 6 N solution of sulphuric acid (150 ml) was stirred at room temperature for 2 h. The reaction mixture was neutralised with a 4 N sodium hydroxide solution and extracted with ethyl acetate (2×200 ml). The combined organic phases was dried (MgSO$_4$) and the solvent was evaporated in vacuo. The residue was submitted to flash chromatography on silica gel (800 g) using n-heptane as eluent to give 18.4 g (76%) of 1-(3-methoxy-phenyl)-1-(2-methylphenyl)-1-propene.

A mixture of 1-(3-methoxyphenyl)-1-(2-methylphenyl)-1-propene (18.3 g, 0.077 mol), carbon tetrachloride (80 ml), benzoylperoxide (0.15 g) and N-bromosuccinimide (14.2 g, 0.080 mol) was heated at reflux temperature for 5 h. The reaction mixture was left overnight at room temperature, filtered and the filtrate was evaporated in vacuo to give 3-bromo-1-(3-methoxyphenyl)-1-(2-methylphenyl)-1-propene in a quantitative yield.

A solution of n-butyllithium in hexanes (32.2 ml, 2.5 M) was added dropwise under a nitrogen atmosphere to ethylene glycol (60 ml) at 10° C.

When addition was complete the mixture was stirred for 0.5 h at room temperature. A solution of 3-bromo-1-(3-methoxyphenyl)-1-(2-methylphenyl)-1-propene (24.4 g, 77 mmol) in toluene (50 ml) was added and the reaction mixture was stirred at room temperature for 4 days and at 65° C. for 6 h. The solvent was evaporated in vacuo, water (250 ml) was added and the mixture was extracted with ethyl acetate (2×200+100 ml). The combined organic phases was dried (MgSO$_4$) and the solvent was evaporated in vacuo. Flash chromatography of the residue on silica gel (320 g) using a mixture of cyclohexane and ethyl acetate gradient as eluent provided 16.6 g (72%) of 2-(3-(3-methoxyphenyl)-3-(2-methylphenyl)-2-propen-1-yloxy) -ethanol.

A solution of 2-(3-(3-methoxyphenyl)-3-(2-methylphenyl)-2-propen-1-yloxy)ethanol (7.6 g, 25.4 mmol) in dry toluene (150 ml) was cooled on an ice-bath and a solution of n-butyllithium in hexanes (11.2 ml, 2.5 M) was added dropwise. The reaction mixture was stirred for 0.5 h at room temperature and p-toluenesulphonyl chloride (5.3 g, 28 mmol) was added. The mixture was stirred at room temperature for 1.5 h. Ethyl (R)-3-piperidinecarboxylate (8.8 g, 50 mmol) and potassium carbonate (7.7 g, 50 mmol) were added and the mixture was stirred at room temperature for 4 h. Toluene (100 ml), acetone (50 ml) and potassium iodide (1.7 g) were added and the reaction mixture was heated at 75° C. for 84 h. The cooled reaction mixture was filtered and the solvent evaporated in vacuo. The residue was submitted to flash chromatography on silica gel (250 g) using a mixture of n-heptane and ethyl acetate (4:1) as eluent to give 7.5 g (68%) of (R)-N-(2-(3-(3-methoxyphenyl)-3-(2-methyl-phenyl)-2-propen-1-yloxy)ethyl)-3-piperidinecarboxylic acid ethyl ester as an oil.

TLC: rf=0.20 (SiO$_2$; ethyl acetate).

(R)-N-(2-(3-(3-Methoxyphenyl)-3-(2-methylphenyl)-2-propen-1-yloxy)ethyl)-3-piperidinecarboxylic acid ethyl ester (7.3 g, 16.7 mmol) was dissolved in ethanol (50 ml) and a 50% sodium hydroxide solution (6.7 g) was added. The reaction mixture was stirred at room temperature for 2 h and water (250 ml) was added. The mixture was extracted with diethyl ether (2×25 ml) and the aqueous phase was neutralised with concentrated hydrochloric acid solution. Part of the solvent was evaporated in vacuo and pH was adjusted to 1 with concentrated hydrochloric acid. The acidic aqueous solution was extracted with dichloromethane (2 ×250+150 ml). The combined organic extracts was dried (MgSO$_4$) and the solvent evaporated in vacuo. The residue was crystallised from acetone and then recrystallized from a mixture of toluene and methanol to give 5.1 g (68%) of the title compound.

M.P. 180–182° C.

Calculated for C$_{25}$H$_{32}$ClNO$_4$: C, 67.3%; H, 7.2%; Cl, 8.0%; N, 3.1% Found: C, 67.3%; H, 7.4%; Cl, 7.9%; N, 3.0%;

$^1$H NMR (DMSO-d$_6$) 63.85 (d, 2H), 6.43 (t, 1H).

Example 31

(R)-N-(2-(3-(3-Methoxyphenyl)-3-(2-methylphenyl)-1-propyloxy)ethyl)-3-piperidinecarboxylic acid hydrochloride The acid prepared in Example 30 (2.0 g, 4.5 mmol) was dissolved into methanol (50 ml) and stirred under an atmosphere of hydrogen for 1 h at room temperature in the presence of 10% palladium on carbon catalyst (65% aqueous paste) and then filtered. The filtrate was evaporated to dryness leaving a solid residue which was recrystallised from a mixture of acetone and ethyl acetate to give 0.30 g (23%) of the title compound.

M.P. 132–138° C.

Calculated for C$_{25}$H$_{34}$ClNO$_4$,1/2H$_2$O: C, 65.7%; H, 7.7%; Cl, 7.8%; N, 3.1% Found: C, 65.4%; H, 7.6%; Cl, 8.2%; N, 2.9%;

$^1$H NMR (DMSO-d$_6$) δ 4.23 (t, 1H).

Example 32
(R)-N-(2-(3,3-Bis(2-Methylphenyl)-2-propen-1-yloxy)ethyl)-3-piperidinecarboxylic acid hydrochloride A solution of n-butyllithium in hexanes (14 ml, 2.5 M) was added drop-wise under a nitrogen atmosphere to ethylene glycol (28 ml) at 0° C. When addition was complete the mixture was stirred 0.5 h at room temperature. 3-Bromo-1,1-bis(2-methyl-phenyl)-1-propene (10.5 g, 35 mmol, prepared in a similar way to the method described in Example 26) was added and the reaction mixture was stirred at room temperature for 12 h and at 70° C. for 24 h. Water (100 ml) was added and the mixture was extracted with ethyl acetate (3×100 ml). The combined organic extracts was dried ($MgSO_4$) and the solvent evaporated in vacuo. Flash chromatography of the residue on silica gel (250 g) using a mixture of n-heptane and ethyl acetate (10:1) as eluent provided 3.0 g (30%) of 2-(3, 3-bis(2-methylphenyl)-2-propen-1-yloxy) ethanol.

A solution of 2-(3,3-bis(2-methylphenyl)-2-propen-1-yloxy)ethanol (3.0 g, 10.7 mmol) in dry toluene (100 ml) was cooled on an ice-bath and a solution of n-butyllithium in hexanes (4.7 ml, 2.5 M) was added drop-wise. The reaction mixture was stirred for 15 minutes at room temperature and p-toluenesulphonyl chloride (2.2 g, 11.7 mmol) was added. The mixture was stirred at room temperature for 2.5 h. Ethyl (R)-3-piperidinecarboxylate (3.4 g, 21.4 mmol) and potassium carbonate (2.9 g, 21.4 mmol) were added and the mixture was stirred at room temperature for 1 h and then at 75° C. for 12 h. Potassium iodide (0.9 g) was added and the mixture was heated at reflux temperature for 15 h. The cooled reaction mixture was filtered and the solvent evaporated in vacuo. Flash chromatography of the residue on silica gel (150 g) using a gradient of n-heptane in ethyl acetate as eluent afforded 2.2 g (49%) of (R)-N-(2-(3,3-bis(2-methylphenyl)-3-propen-1-yl)oxyethyl)-3-piperidinecarboxylic acid ethyl ester as an oil.

TLC: rf=0.55 ($SiO_2$; ethyl acetate/methanol=9:1).

(R)-N-(2-(3,3-bis(2-methylphenyl)-2-propen-1-yloxy)-ethyl)-3-piperidinecarboxylic acid ethyl ester (2.2 g, 5.1 mmol) was dissolved in ethanol (20 ml) and 12 N sodium hydroxide solution (2.1 ml) was added. The reaction mixture was stirred at room temperature for 0.5 h. Water (200 ml) was added and the mixture was extracted with diethyl ether (5×20 ml). pH was adjusted to 1 with concentrated hydrochloric acid and the mixture was extracted with dichloromethane (2×250+100 ml). The combined organic extracts were dried ($MgSO_4$) and the solvent was evaporated in vacuo to give a residue which was crystallised from ethyl acetate and finally recrystallized from a mixture of methanol and toluene. This provided 1.4 g (66%) of the title compound.

M.P. 188–190° C.

Calculated for $C_{25}H_{32}ClNO_3$: C, 69.8%; H, 7.5%; N, 3.3% Found: C, 70.0%; H, 7.7%; N, 3.2%;

$^1$H NMR (DMSO-$d_6$) δ 3.95 (d, 2H); 5.90 (t, 1H).

Example 33
(R)-N-(2-(3,3-Bis(2-Methylphenyl)-1-propyloxy)ethyl)-3-piperidinecarboxylic acid hydrochloride The acid prepared in Example 32 (1.1 g, 2.6 mmol) was dissolved in methanol (25 ml) and stirred under an atmosphere of hydrogen for 1 h at room temperature in the presence of 10% palladium on carbon catalyst (35% aqueous paste) and then filtered. The filtrate was evaporated to dryness leaving a residue which was treated with a mixture of ethyl acetate and acetone and filtered to give a solid which was recrystallised from a mixture of methanol and toluene to give 0.75 g (67%) of the title compound as a solid.

M.P. 193–195.5° C.

Calculated for $C_{25}H_{34}ClNO_3$: C, 69.5%; H, 7.9%; N, 3.2% Found: C, 69.6%; H, 8.3%; N, 3.2%;

$^1$H NMR (DMSO-$d_6$) δ 4.38 (t, 1H).

Example 34
(R)-N-(3-(3,3-Bis(2-Methylphenyl)-2-propen-1-yloxy)-1-propyl)-3-piperidinecarboxylic acid hydrochloride A solution of n-butyllithium in hexanes (15.2 ml, 2.5 M) was added dropwise under a nitrogen atmosphere to 1,3-propanediol (31 ml) on an ice-bath. When addition was complete the mixture was stirred 0.5 h at room temperature. 3-Bromo-1, 1-bis(2-methylphenyl)-1-propene (11.5 g, 38 mmol), prepared in a similar way to the method described in Example 26) was added and the reaction mixture was stirred at room temperature for 48 h and at 75° C. for 36 h. Water (100 ml) was added and the mixture was extracted with ethyl acetate (100 ml). The phases were separated and the organic phase was washed with water (2×50 ml), dried ($MgSO_4$) and the solvent evaporated in vacuo. Flash chromatography of the residue on silica gel (300 g) using a gradient of n-heptane in ethyl acetate as eluent provided 3.5 g (31%) of 3-(3,3-bis(2-methyl phenyl)-2-propen-1-yloxy)-1-propanol.

A solution of 3-(3,3-bis(2-methylphenyl)-2-propen-1-yloxy)-1-propanol (3.45 g, 11.6 mmol) in dry toluene (150 ml) was cooled in an ice-bath and a solution of n-butyllithium in hexanes (5.1 ml, 2.5 M) was added dropwise. The reaction mixture was stirred for 15 minutes at room temperature and p-toluenesulphonyl chloride (2.44 g, 12.8 mmol) was added. The mixture was stirred at room temperature for 3 h. Ethyl (R)-3-piperidinecarboxylate (4.5 g, 23.3 mmol) and potassium carbonate (3.2 g, 23.3 mmol) were added and the mixture was stirred at room temperature for 0.5 h and then at 75° C. for 12 h. Potassium iodide (1.0 g) and acetone (40 ml) were added and the mixture was heated at reflux temperature for 15 h. Acetone (50 ml) was added and the cooled reaction mixture was filtered and the solvent evaporated in vacuo. Flash chromatography of the residue on silica gel (280 g) using a gradient of n-heptane in ethyl acetate as eluent afforded 2.6 g (52%) of (R)-N-(3-(3,3-bis-(2-methylphenyl)-2-propen-1-yloxy)-1-propyl)-3-piperidinecarboxylic acid ethyl ester as an oil.

TLC: rf=0.52 ($SiO_2$; methanol/ethyl acetate=1:9).

(R)-N-(3-(3,3-Bis(2-Methylphenyl)-2-propen-1-yloxy)-1-propyl)-3-piperidinecarboxylic acid ethyl ester (2.6 g, 6.0 mmol) was dissolved in ethanol (20 ml) and a 12 N sodium hydroxide solution (2.5 ml) was added. The reaction mixture was stirred at room temperature for 0.5 h. Water (250 ml) was added and the mixture was extracted with diethyl ether (2×50 ml). A 2 M hydrochloric acid solution was added to the aqueous phase until pH 1 and the mixture was extracted with dichloromethane (3×200 ml). The combined organic extracts was dried ($MgSO_4$) and the solvent was evaporated in vacuo to give a residue which was treated with a mixture of ethyl acetate and acetone and finally recrystallised from a mixture of methanol and toluene. This provided 1.3 g (49%) of the title compound.

TLC: rf=0.47 ($SiO_2$; methanol/dichloromethane=1:1).

M.P. 156–158° C.

Calculated for $C_{26}H_{34}ClNO_3$: C, 70.3%; H, 7.7%; N, 3.2% Found: C, 70.3%; H, 7.7%; N, 2.9%;

$^1$H NMR (DMSO-$d_6$) δ 3.89 (d, 2H); 5.87 (t, 1H).

Example 35
(R)-N-(3-(3,3-Bis(2-Methylphenyl)-1-propyloxy)-1-propyl)-3-piperidinecarboxylic acid hydrochloride The acid prepared in Example 34 (0.75 g, 1.7 mmol) was dissolved in methanol (25 ml) and stirred under an atmosphere of hydrogen for 1 h at room temperature in the presence of 10% palladium on carbon catalyst (35% aqueous paste) and then filtered. The filtrate was evaporated to dryness leaving a residue which was treated with a mixture of ethyl acetate and acetone and filtered to give a solid which was recrystallised from toluene to give 0.20 g (26%) of the title compound as a solid.

TLC: rf=0.39 (SiO$_2$; methanol/dichloromethane=1:1).

M.P. 186–187° C.

Calculated for C$_{26}$H$_{36}$ClNO$_3$: C, 70.0%; H, 8.1%; N, 3.1%; Found: C, 69.7%; H, 8.2%; N, 3.0%;

$^1$H NMR (DMSO-d$_6$) δ 4.39 (t, 1H).

Example 36

(R)-N-(2-(3-(3-Methoxyphenyl)-3-phenyl-2-propen-1-yloxy)ethyl)-3-piperidinecarboxylic acid A solution of n-butyllithium in hexanes (76 ml, 2.5 M) was added drop-wise under a nitrogen atmosphere to ethylene glycol (30 ml) at 10° C. When addition was complete the mixture was stirred for 0.5 h at room temperature. 3-Bromo-1-(3-methoxyphenyl)-1-phenyl-1-propene (57.5 g, 0.19 mol, prepared in a similar way to the method described in Example 26) in toluene (40 ml) was added and the reaction mixture was stirred at room temperature for 84 h. The mixture was poured into water (400 ml) and extracted with ethyl acetate (250+100 ml). The combined organic extracts was washed with water, brine and dried (Na$_2$SO$_4$). The solvent was evaporated in vacuo to give a residue which was stripped with methanol and dichloromethane successively. This afforded 53.1 g (99%) of 2-(3-(3-methoxyphenyl)-3-phenyl-2-propen-1-yloxy)ethanol.

TLC: rf=0.41 (SiO$_2$; chloroform/methanol=19:1).

A mixture of 2-(3-(3-methoxyphenyl)-3-phenyl-2-propen-1-yloxy)ethanol (52 g, 0.18 mol) and triethylamine (46 g, 0.46 mol) in dry toluene (200 ml) kept under a nitrogen atmosphere was cooled below 10 C and a solution of methanesulphonyl chloride (41.7 g, 0.36 mol) in dry toluene (200 ml) was added dropwise keeping the temperature below 10° C. When addition was complete the reaction mixture was stirred for 1 h at 5° C. and then for 0.5 h at approximately 15° C. Water was added (250 ml) and the mixture was stirred at room temperature for 0.5 h. The separated organic phase was washed with a 5% sodium bicarbonate solution, brine and dried (Na$_2$SO$_4$). The mixture was filtered and the filtrate was reduced to approximately 500 ml in vacuo. Ethyl (R)-3-piperidinecarboxylate (57.2 g, 0.36 mol) and potassium carbonate (62.8 g, 0.46 mol) were added and the mixture was heated at reflux temperature for 48 h. The cooled reaction mixture was filtered and the solid was washed with toluene and ethyl acetate successively. The combined organic filtrates was evaporated in vacuo to an oily residue which was dissolved into ethyl acetate (250 ml). Water (150 ml) was added and pH was adjusted to 4 with 10% citric acid solution. The phases were separated and the organic phase was washed with water (150 ml). The combined aqueous phases was extracted with ethyl acetate (150 ml) and then discarded. The combined organic phases was washed with a 5% sodium bicarbonate solution, brine, dried (Na$_2$SO$_4$) and the solvent evaporated in vacuo. The residue was dissolved in toluene (150 ml) and a solution of tartaric acid (42 g) in water (120 ml) was added. The phases were separated and the organic phase was extracted with another solution of tartaric acid (12 g) in water (50 ml). The combined aqueous extracts was extracted with ethyl acetate (200 ml) which was discarded. Ethyl acetate (200 ml) was added to the acidic aqueous phase which was made alkaline with excess of a sodium bicarbonate solution. The separated organic phase was washed with brine and dried (Na$_2$SO$_4$). The solvent was evaporated in vacuo to give 46.6 g (60%) of (R)-N-(2-(3-(3-methoxyphenyl)-3-phenyl-2-propen1-yloxy)ethyl)-3-piperidinecarboxylic acid ethyl ester as an oil.

TLC: rf=0.36 (SiO$_2$; chloroform/methanol/acetic acid=20:2:1).

(R)-N-(2-(3-(3-Methoxyphenyl)-3-phenyl-2-propen-1-yloxy)ethyl)-3-piperidinecarboxylic acid ethyl ester (25 g, 59 mmol) was dissolved into 96% ethanol (275 ml) and a 12 N sodium hydroxide solution (22 ml) was added. The reaction mixture was stirred at room temperature for 3.5 h. The solvent was evaporated in vacuo and dichloromethane was added (250 ml). A concentrated hydrochloric acid solution (29.5 ml) was added with cooling of the reaction vessel in an ice-bath. The phases were separated and the organic phase was dried (Na$_2$SO$_4$). The solvent was evaporated in vacuo to give a residue which was dissolved into water (250 ml). The aqueous solution was extracted with toluene (3×50 ml) and diethyl ether (50 ml). The organic extracts were discarded and from the aqueous phase water was evaporated in vacuo to give 25 g (98%) of the title compound as an oil.

TLC: rf=0.23 (SiO$_2$; chloroform/methanol/acetic acid=80:15:5).

HPLC retention time=12.0 and 12.4 minutes (system B).

$^1$H NMR (DMSO-d$_6$) δ 4.02 (t, 2H); 6.25 (dt, 1H).

Example 37

(R)-N-(2-(3-(3-Methoxyphenyl)-3-phenyl-1-propyloxy) ethyl)-3-piperidinecarboxylic acid fumarate The acid prepared in Example 36 (20.0 g, 46.3 mmol) was dissolved in methanol (300 ml) and stirred under an atmosphere of hydrogen for 1 h at room temperature in the presence of 10% palladium on carbon catalyst (35% aqueous paste) and then filtered. The filtrate was evaporated to dryness leaving a residue which was stripped with dichloromethane to give 19.2 g (96%) of the title compound as a foam. The material was submitted to reverse phase column chromatography using a mixture of methanol, a 2 M aqueous ammonia solution and a 3% aqueous sodium chloride solution (60:10:30) as eluent. This afforded 12.0 g (53%) of the title compound as a solid.

HPLC retention time=11.0 minutes (system B).

$^1$H NMR (DMSO-d$_6$) δ 4.05 (t, 1H).

Example 38

(R)-N-(2-(3,3-Bis(4-Chlorophenyl)-2-propen-1-yloxy) ethyl)-3-piperidinecarboxylic acid ethyl ester A solution of n-butyllithium in hexanes (15.0 ml, 2.5 M) was added dropwise under a nitrogen atmosphere to ethylene glycol (30 ml) at 10° C. When addition was complete the mixture was stirred for 0.5 h at room temperature. 3-Bromo-1,1-bis(4-chlorophenyl)-1-propene (13.0 g, 38 mmol, prepared similarly to the method described in Example 26) was added and the reaction mixture was stirred at room temperature for 72 h. The mixture was poured into water (100 ml) and extracted with ethyl acetate (2×75 ml). The combined organic extracts was dried (Na$_2$SO$_4$) and the solvent evaporated in vacuo. Flash chromatography of the residue on silica gel (200 g) using a mixture of n-heptane and ethyl acetate (3:2) as eluent provided 8.1 g (66%) of 2-(3,3-bis-(4-chlorophenyl)-2-propen- 1-yloxy)ethanol.

M.P. 93–95° C.

A solution of 2-(3,3-bis(4-chlorophenyl)-2-propen-1-yloxy)ethanol (4.0 g, 12.4 mmol) in dry THF (25 ml) kept under a nitrogen atmosphere was cooled to 10° C. and a solution of n-butyllithium in hexanes (5.4 ml, 2.5 M) was added dropwise. The reaction mixture was stirred for 15 minutes at room temperature and p-toluenesulphonyl chloride (2.6 g, 13.8 mmol) was added. The mixture was stirred at room temperature for 1 h. Ethyl (R)-3-piperidinecarboxylate (1.9 g, 12.1 mmol) and potassium carbonate (3.4 g, 24.6 mmol) were added and the mixture was heated at reflux temperature for 18 h. To the cooled reaction mixture THF (50 ml) was added. The mixture was filtered and the solvent evaporated in vacuo. Column chromatography of the residue on silica gel (100 g) using a mixture of n-heptane and ethyl acetate (3:2) as eluent provided 0.6 g (11 %) of the title compound as an oil.

$^1$H NMR (CDCl$_3$) δ 4.02 (d, 2H); 6.20 (t, 1H).

Example 39

(R)-N-(2-(3,3-Bis(4-Chlorophenyl)-2-propen-1-yloxy) ethyl)-3-piperidinecarboxylic acid hydrochloride The ester prepared in Example 38 (0.6 g, 1.3 mmol) was dissolved in ethanol (10 ml) and a 12 N sodium hydroxide solution (0.5 ml) was added. The reaction mixture was stirred at room temperature for 5 h. A concentrated hydrochloric acid solution was added with cooling on an ice-bath until pH 1 and dichloromethane (300 ml) was added. The resulting emulsion was dried (Na$_2$SO$_4$) ant the solvent evaporated in vacuo to give a residue which was agitated with acetone. This afforded 0.3 g (50 %) of the title compound as a solid.

M.P. 203–204° C.

Calculated for C$_{23}$H$_{26}$Cl$_3$NO$_3$.H$_2$O: C, 56.5%; H, 5.8%; Cl, 7.3%; N, 2.9%; Found: C, 56.6%; H, 5.5%; Cl, 7.4%; N, 2.6%;

$^1$H NMR (DMSO-d$_6$) δ 4.02 (d, 2H); 6.30 (t, 1H).

The compound in Example 40 was prepared by a method similar to that described in Examples 38 and 39.

Example 40

(R)-1-(2-((1,1-Bis(4-fluorophenyl)-1-propen-3-yl)oxy) ethyl)-3-piperidinecarboxylic acid hydrochloride

M.P. 184–186° C.

Calculated for C$_{23}$H$_{26}$ClF$_2$NO$_3$: C, 63.1%; H, 6.0%; N, 3.2%; Found: C, 62.9%; H, 6.2%; N, 3.1%.

Example 41

(R)-N-(2-(3-(3-Chlorophenyl)-3-phenyl-2-propen-1-yloxy)-ethyl)-3-piperidinecarboxylic acid A solution of n-butyllithium in hexanes (75 ml, 2.5 M) was added drop-wise under a nitrogen atmosphere to ethylene glycol (150 ml) at 5° C. When addition was complete the mixture was stirred at room temperature for 0.5 h. 3-Bromo-1-(3-chlorophenyl)-1-phenyl-1-propene (58.5 g, 0.19 mol, prepared in a similar way to the method described in Example 26) was added and the reaction mixture was stirred at room temperature for 96 h. The reaction mixture was poured into water (200 ml) and extracted with ethyl acetate (2×200 ml). The combined organic extracts was washed with brine and dried (Na$_2$SO$_4$). The solvent was evaporated in vacuo to give a residue which was stripped with methanol and dichloromethane sucessively. This afforded 52.2 g (96%) of 2-(3-(3-chloro-phenyl)-3-phenyl-2-propen-1-yloxy)ethanol.

TLC: rf=0.10 (SiO$_2$; n-heptane/ethyl acetate=4:1).

A mixture of 2-(3-(3-chlorophenyl)-3-phenyl-2-propen-1-yloxy)ethanol (52.2 g, 0.18 mol) and triethylamine (45.7 g, 0.45 mol) in dry toluene (200 ml) kept under a nitrogen atmosphere was cooled to 5° C. and a solution of methanesulphonyl chloride (41.4 g, 0.36 mol) in dry toluene (200 ml) was added dropwise keeping the temperature below 10° C. When addition was complete the reaction mixture was stirred for 1 h at 5° C. Water was added (250 ml) and the mixture was stirred at room temperature for 10 minutes. The phases were separated and the aqueous phase was extracted with a small portion of toluene. The combined organic extracts were washed with brine and dried (Na$_2$SO$_4$). The mixture was filtered and the filtrate was reduced in vacuo to approximately 500 ml. Ethyl (R)-3-piperidinecarboxylate (56.8 g, 0.36 mol) and potassium carbonate (49.9 g, 0.36 mol) were added and the mixture was heated at reflux temperature for 7 days. The cooled reaction mixture was poured into water (200 ml) and extracted with ethyl acetate (2×200 ml). The combined organic extracts were washed with a sodium citrate buffer solution (pH 5) and then extracted with a 34% aqueous tartaric acid solution (3×100 ml). The combined acidic aqueous extracts were poured into a mixture of ice water (3 l) and ethyl acetate (400 ml). Sodium hydroxide pellets (27.2 g) was added until pH was measured at ca. 4 and the phases were separated. The organic phase was washed with a 5% sodium bicarbonate solution (3×150 ml) and dried (Na$_2$SO$_4$). The solvent was evaporated in vacuo to give 57.5 g (74%) of (R)-N-(2-(3-(3-chlorophenyl)-3-phenyl-2-propen-1-yloxy)ethyl)-3-piperidinecarboxylic acid ethyl ester as an oil.

TLC: rf=0.45 (SiO$_2$; dichloromethane/methanol/acetic acid=20:2:1).

(R)-N-(2-(3-(3-Chlorophenyl)-3-phenyl-2-propen-1-yloxy)-ethyl)-3-piperidinecarboxylic acid ethyl ester (3.0 g, 7.0 mmol) dissolved in 96% ethanol (10 ml) and a 12 N sodium hydroxide solution (1.75 ml) was added. The reaction mixture was stirred at room temperature for 5 h. The solvent was evaporated in vacuo and dichloromethane was added (100 ml). A concentrated hydrochloric acid solution (2.9 ml) was added with cooling on an ice-bath. The phases were separated, and from the organic phase the solvent was evaporated in vacuo. Water (100 ml) was added to the residue and the aqueous solution was washed with small portions of ethyl acetate. The aqueous phase was reduced in vacuo to approx. 50 ml and dichloromethane (250 ml) was added. A 4 N sodium hydroxide solution was added until the pH was measured as 8.3. The phases were separated and the organic phase was dried (Na$_2$SO$_4$). The solvent was evaporated in vacuo to give 2.7 g (96%) of the title compound.

HPLC retention time=16.0 and 16.3 minutes (system B).

$^1$H NMR (CDCl$_3$) δ 4.02 (t, 2H); 6.20 (dt, 1H).

The compounds in Examples 42–46 were prepared by a method similar to that described in Example 41.

Example 42

(R)-1-(2-(1,1-Bis(4-fluoro-2-methylphenyl)-1-propen-3-yl) oxy)-ethyl)-3—piperidinecarboxylic acid hydrochloride

M.P. 170–177° C.

Calculated for C$_{25}$H$_{30}$ClF$_2$NO$_3$.1/4H$_2$O: C, 63.8%; H, 6.5%; N, 3.0%; Found: C, 63.9%; H, 6.6%; N, 2.9%;

$^1$H NMR (400 MHz, DMSO-d.) δ 5.93 (t, 1H); 3.93 (d, 2H).

Example 43

(R)-1-(3-((1,1-Diphenyl-1-propen-3-yl)oxy)-1-propyl)-3-piperidinecarboxylic acid hydrochloride Amorph.

HPLC retention time=23.1 minutes (system D).

$^1$H NMR (400 MHz, DMSO-d$_6$) δ 6.21 (t, 1H); 3.97 (d, 2H).

Example 44
(R)-1-(2-(1,1-Bis(4-chloro-2-methylphenyl)-1-propen-3-yl)oxy)ethyl)-3-piperidinecarboxylic acid hydrochloride Amorph.

HPLC retention time=30.1 minutes (system D).

$^1$H NMR (400 MHz, DMSO-d$_6$) δ 5.93 (t, 1H); 3.88 (d, 2H); 2.23 (s, 3H); 2.00 (s, 3H).

Example 45
1-(2-(1,1-Bis(4-fluoro-2-methylphenyl)-1-propen-3-yl)oxy)-ethyl)-1,2,5,6-tetrahydropyridine-3-carboxylic acid hydrochloride Amorph.

Calculated for C$_{25}$H$_{28}$ClF$_2$NO$_3$.3/4H$_2$O: C, 62.9%; H, 6.2%; Cl, 7.4%; N, 2.9%; Found: C, 63.0%; H, 6.2%; Cl, 7.3%; N, 2.7%;

$^1$H NMR (400 MHz, DMSO-d$_6$) δ 5.93 (t, 1H); 3.95 (d, 2H).

Example 46
(S)-1-(2-(1,1-Bis(4-fluoro-2-methylphenyl)-1-propen-3-yl)oxy)-ethyl)-3—piperidinecarboxylic acid hydrochloride

M.P. 184–186° C.

Calculated for C$_{25}$H$_{30}$ClF$_2$NO$_3$: C, 64.4%; H, 6.5%; N, 3.0%; Found: C, 64.3%; H, 6.7%; N, 2.8%;

$^1$H NMR (400 MHz, DMSO-d$_6$) δ 5.93 (t, 1H); 4.93 (d, 2H).

Example 47
(R)-N-(2-(3-(3-Methylphenyl)-3-phenyl-2-propen-1-yloxy)ethyl)-3-piperidinecarboxylic acid A solution of n-butyllithium in hexane (73 ml, 2.5 M) was added drop-wise under a nitrogen atmosphere to ethylene glycol (150 ml) at 5° C. When addition was complete the mixture was stirred for 0.5 h at room temperature. 3-Bromo-1-(3-methylphenyl)-1-phenyl-1-propene (52 g, 0.18 mol, prepared in a similar way to that described in Example 26) was added and the reaction mixture was stirred at room temperature for 5 days. The reaction mixture was poured into water (200 ml) and extracted with diethyl ether (2×200 ml). The combined organic extracts was washed with brine and dried (MgSO$_4$). The solvent was evaporated in vacuo to give a residue which was submitted to flash chromatography on silica gel (900 g) using a mixture of n-heptane and ethyl acetate as eluent. This afforded 31 g (64%) of 2-(3-(3-methylphenyl)-3-phenyl-2-propen-1-yloxy)ethanol.

TLC: rf=0.08 (SiO$_2$; n-heptane/ethyl acetate=4:1).

A mixture of 2-(3-(3-methylphenyl)-3-phenyl-2-propen-1-yl-oxy)ethanol (16 g, 60 mmol) and triethylamine (15.1 g, 149 mmol) in dry toluene (75 ml) kept under a nitrogen atmosphere was cooled to 5° C. and a solution of methane-sulphonyl chloride (13.7 g, 119 mmol) in dry toluene (75 ml) was added dropwise keeping the temperature below 10° C. When addition was complete the reaction mixture was stirred for 1.5 h at 5° C. Water was added (100 ml) and the mixture was stirred at room temperature for 0.5 h. The phases were separated and the aqueous phase was extracted with a small portion of toluene. The combined organic extracts was washed with brine, dried (Na$_2$SO$_4$) and filtered. To the filtrate was added ethyl (R)-3-piperidinecarboxylate (10.3 g, 66 mmol) and potassium carbonate (9.9 g, 72 mmol) and the mixture was heated at reflux temperature for 6 days. Another portion of ethyl (R)-3-piperidinecarboxylate (5.3 g) was added and the mixture was heated at reflux temperature for another 24 h. The reaction mixture was poured into ice water (200 ml) and extracted with ethyl acetate (2×200 ml). The combined organic extracts was washed with a sodium citrate buffer solution (2×100 ml, pH 5) and then extracted with a 5% aqueous citric acid solution (4×30 100 ml). Toluene (120 ml) was added to the combined acidic extracts and sodium hydroxide pellets was added to the mixture until the pH was measured at 8.5. The phases were separated and the organic phase was dried (Na$_2$SO$_4$). The solvent was evaporated in vacuo to give 9.4 g (39 %) of (R)-N-(2-(3-(3-methylphenyl)-3-phenyl-2-propen-1-yloxy)ethyl)-3-piperidinecarboxylic acid ethyl ester as an oil.

TLC: rf=0.50 (SiO$_2$; dichloromethane/methanol/acetic acid=20:2:1).

(R)-N-(2-(3-(3-Methylphenyl)-3-phenyl-2-propen-1-yloxy)ethyl)-3-piperidinecarboxylic acid ethyl ester (3.5 g, 8.6 mmol) was dissolved in 96% ethanol (10 ml) and a 12 N sodium hydroxide solution (2.2 ml) was added. The reaction mixture was stirred at room temperature for 4 h. The solvent was evaporated in vacuo and dichloromethane (100 ml) and water (10 ml) were added. A concentrated hydrochloric acid solution (3.4 ml) was added with cooling on an ice-bath. The phases were separated and from the organic phase the solvent was evaporated in vacuo. Water (100 ml) was added to the residue and the aqueous solution was washed with small portions of ethyl acetate. The aqueous phase was reduced to approx. 10 ml in vacuo. Dichloromethane (250 ml) and water (40 ml) were added and pH of the solution was adjusted to 8.5 with a 4 N sodium hydroxide solution. The phases were separated and the organic phase was dried (Na$_2$SO$_4$). The solvent was evaporated in vacuo to give 2.4 g (74%) of the title compound.

HPLC retention time=17.8 minutes (system B).

$^1$H NMR (CDCl$_3$) δ 4.03 (dd, 2H); 6.17 (t, 1H).

Example 48
(R)-N-(2-(3-(3-Methylphenyl)-3-phenyl-1-propyloxy)ethyl)-3-piperidinecarboxylic acid The acid prepared in Example 47 (8.2 g, 21.6 mmol) was dissolved in methanol (150 ml) and stirred under an atmosphere of hydrogen for 1 h at room temperature in the presence of 10% palladium on carbon catalyst (35% aqueous paste) and then filtered. The filtrate was evaporated to dryness leaving a residue which was disolved into dichloromethane and dried (Na$_2$SO$_4$). The solvent was evaporated in vacuo to give 2.3 g (28 %) of the title compound as a foam.

HPLC retention time=16.0 minutes (system B).

$^1$H NMR (DMSO-d$_6$) δ 4.05 (t, 1H).

The compound in Example 49 was prepared by a method similar to that described in Example 48.

Example 49
(R)-1-(2-(3,3-Bis(4-fluoro-2-methylphenyl)-1-propyloxy)ethyl-3-piperidinecarboxylic acid hydrochloride Amorph.

HPLC retention time=25.9 minutes (system D).

$^1$H NMR (400 MHz, DMSO-d$_6$) δ 4.35 (t, 1H); 2.25 (s, 6H).

Example 50
(R)-1-(2-((2,2-Diphenylethenyl)oxy)ethyl)-3-piperidinecarboxylic acid ethyl ester The (R)-enantiomer of ethyl nipecotate (100 g, 0.64 mole) (Akkerman, A. M. et al., *Gazz.Chim.Ital.*, 102 (1972) 189) was mixed in dry acetone (300 ml) with 2-bromoethanol (85 g, 0.68 mole), dried, powdered potassium carbonate (188 g, 1.28 mole) and potassium iodide (21.6 g, 0.13 mole). The reaction mixture was stirred at room temperature for 18 h and at reflux for 24 h. Filtration of the reaction mixture and evaporation of the resultant filtrate gave (R)-1-(2-hydroxyethyl)nipecotic acid ethyl ester as an oil, which was purified by distillation in vacuo (110–115C, 0.1 mmHg), yield (72.2 g, 56%). TLC: rf=0.20 (SiO$_2$; dichloromethane/methanol=19:1).

A sample of the above alcohol (140 g, 0.70 mole) was dissolved in toluene (400 ml) and thionyl bromide (80 ml, 0.77 mole) was introduced with vigorous stirring. After 1.5 h the exotherm reaction had subsided and diethyl ether (400 ml) was added. The resultant precipitate was collected by filtration and washed with diethyl ether. The solid was triturated with ethyl acetate, again collected on a filter and dried to provide (R)-1-(2-bromoethyl)nipecotic acid ethyl ester hydrobromide (175 g, 73%) as a white solid.

M.P. 210–215° C.

Diphenylacetaldehyde (4.9 g, 0.025 mole) was added dropwise to a mixture of sodium hydride (1.5 g, 0.05 mole, 80% oil dispersion) and dry toluene (25 ml) at 0 C. This mixture was stirred at room temperature for 0.5 h, heated to 50° C. and allowed to cool to room temperature. The above (R)-1-(2-bromoethyl)nipecotic acid ethyl ester hydrobromide (8.6 g, 0.025 mole) was added portionwise whilst the temperature was kept below 30° C. with an ice-water bath. After being stirred for 1 h the reaction mixture was filtered, and the filtrate was evaporated to dryness.

Flash chromatography of the residue on silica gel (200 g) using a mixture of heptane and tetrahydrofuran (4:1) as eluent provided the title compound (6.6 g, 69%) as an oil.

TLC: rf=0.24 (SiO$_2$; heptane/THF=7:3).

Example 51
(R)-1-(2-((2,2-Diphenylethenyl)oxy)ethyl)-3-piperidinecarboxylic acid hydrochloride (R)-1-(2-((2,2-Diphenylethenyl)oxy)ethyl)-3-piperidinecarboxylic acid ethyl ester (Example 50) (3.0 g, 0.079 mol) was dissolved in ethanol (20 ml) and 12 N sodium hydroxide solution (2.0 ml) was introduced. After stirring the solution at room temperature for 2.5 h, 37% hydrochloric acid (ca. 2.2 ml) was added, with acidity measured at pH 2. Dichloro-methane (300 ml) was introduced, and the mixture was dried (MgSO$_4$). Filtration and evaporation of the filtrate gave a solid, which was triturated with diethyl ether, to give the title compound (2.65 g, 86%) as a white solid.

M.P. 210–216° C.

Calculated for C$_{22}$H$_{26}$ClNO$_3$: C, 68.1%; H, 6.8%; N, 3.6%; Cl, 9.15%; Found: C, 67.6%; H, 6.7%; N, 3.65%; Cl, 9.0%.

Example 52
Z-(R)-1-(2-((2-(2-Methylphenyl)-2-phenylethenyl)oxy)ethyl)-3-piperidinecarboxylic acid hydrochloride Z-(R)-1-(2-((2-(2-Methylphenyl)-2-phenylethenyl)oxy)ethyl)-3-piperidinecarboxylic acid ethyl ester (2.0 g, 0.0051 mol, prepared similarly to the method described in Example 50) was dissolved in ethanol (8 ml) and 12 N sodium hydroxide solution (1.3 ml) was introduced. After stirring the solution at room temperature for 2 h, 37% hydrochloric acid (ca. 1.8 ml) was added with cooling, followed by dichloromethane (300 ml) and the mixture was dried (Na$_2$SO$_4$). Filtration and evaporation of the filtrate gave a residue, which was co-evaporated with acetone. The solid product was triturated with ethyl acetate, collected by filtratiion and dried in vacuo to give the title compound (0.70 g, 34%).

M.P. 206–211° C.

Calculated for C$_{23}$H$_{28}$ClNO$_3$: C, 68.7%; H, 7.0%; N, 3.5%; Cl, 8.8%; Found: C, 67.7%; H, 7.1%; N, 3.5%; Cl, 8.9%.

Example 53
E-(R)-1-(2-((2-(2-Methylphenyl)-2-phenylethenyl)oxy)ethyl)-3-piperidinecarboxylic acid hydrochloride E-(R)-1-(2-((2-(2-Methylphenyl)-2-phenylethenyl)oxy)ethyl)-3-piperidinecarboxylic acid ethyl ester (1.1 g, 0.0028 mol, prepared similarly to the method described in Example 50) was dissolved in ethanol (5 ml) and 12 N sodium hydroxide solution (0.7 ml) was introduced. After stirring the solution at room temperature for 2 h, 37% hydrochloric acid solution (ca. 1.0 ml) was added (with cooling) followed by dichloromethane (300 ml) and the mixture was dried (Na$_2$SO$_4$). Filtration and evaporation of the filtrate gave a residue, which was co-evaporated with acetone. The solid product was triturated with ethyl acetate, collected by filtration and dried in vacuo to provide the title compound (0.70 g, 62%).

M.P. 195–196° C.

Calculated for C$_{23}$H$_{28}$ClNO$_3$: C, 68.7%; H, 7.0%; N, 3.5%; Cl, 8.8%; Found: C, 68.1%; H, 7.2%; N, 3.4%; Cl, 8.7%.

Example 54
E or Z-(R)-1-(2-((2-(2-Chlorophenyl)-2-phenylethenyl)oxy)ethyl)-3-piperidinecarboxylic acid hydrochloride E or Z-(R)-1-(2-((2-(2-Chlorophenyl)-2-phenylethenyl)oxy)ethyl)-3-piperidinecarboxylic acid ethyl ester (1.0 g, 0.0024 mol, prepared similarly to the method described in Example 50) was dissolved in ethanol (10 ml) and 10 N sodium hydroxide solution (2.42 ml) was introduced. After stirring the solution at room temperature for 5 h, water (100 ml) was added and the mixture was neutralized with 2 N hydrochloric acid solution.

Evaporation of ethanol under reduced pressure gave an aqueous solution, which was acidified to pH 0.5 with 2 N hydrochloric acid solution and extracted with dichloromethane (4×100 ml). The combined extracts was dried (Na$_2$SO$_4$) and evaporated to an oil, which was dissolved in a trace of methanol. Toluene (20 ml) was introduced, and the product solution was heated on a steam bath. On cooling the title compound (0.64 g, 62%), a white crystalline solid, was collected and dried in vacuo.

M.P. softens at 170° C.; melts at 198° C.

Calculated for C$_{22}$H$_{25}$Cl$_2$NO$_3$: C, 62.6%; H. 5.7%; N, 3.2%; Cl, 16.8%; Found: C, 62.5%; H, 6.0%; N, 3.2%; Cl, 16.6%.

Example 55
E or Z-(R)-1-(2-((2-(2-Chlorophenyl)-2-phenylethenyl)oxy)ethyl)-3-piperidinecarboxylic acid hydrochloride E or Z-(R)-1-(2-((2-(2-Chlorophenyl)-2-phenylethenyl)oxy)ethyl)-3-piperidinecarboxylic acid ethyl ester (1.0 g, 0.0024 mol) (opposite geometric isomer of Example 54) was dissolved in ethanol (20 ml) and 10 N sodium hydroxide solution (2.42 ml) was introduced. After stirring the reaction mixture at room temperature for 16 h, water (100 ml) was added and the mixture was neutralized with 2 N hydrochloric acid solution. Evaporation of ethanol under reduced pressure gave an aqueous solution, which was acidified to pH 1 with 2 N hydrochloric acid and extracted with dichloromethane (4×100 ml). The combined extracts was dried (Na$_2$SO$_4$) and evaporated to a solid, which was recrystallized from methanol/toluene to give the title compound (0.58 g, 56%) as white crystals after drying in vacuo.

M.P. 227–228° C.

Calculated for C$_{22}$H$_{25}$Cl$_2$NO$_3$: C, 62.6%; H, 5.7%; N, 3.3%; Cl, 16.8%; Found: C, 62.6%; H, 6.1%; N, 3.2%; Cl, 16.7%.

Example 56

(R)-1-(3-((2,2-Diphenylethenyl)oxy)-1-propyl)-3-piperidinecarboxylic acid hydrochloride (R)-1-(3-((2,2-Diphenylethenyl)oxy)propyl)-3-piperidinecarboxylic acid ethyl ester (0.60 g, 0.0015 mol, prepared similarly to the method described in Example 50) was dissolved in ethanol (5 ml) and 12 N sodium hydroxide solution (0.4 ml) was introduced. After stirring the solution at room temperature for 2 h, 37% hydrochloric acid (ca. 0.52 ml) was added with cooling followed by dichloromethane (250 ml). The mixture was dried ($Na_2SO_4$). Filtration and evaporation 15 of the filtrate gave a residue, which was co-evaporated with acetone. The solid product was triturated with acetone, collected by filtration and dried in vacuo to give the title compound (0.30 g, 50%).

M.P. 176–180° C.

Calculated for $C_{23}H_2,ClNO_3,0.25H_2O$: C, 68.0%; H, 7.1%; N, 3.45%; Cl, 8.7%; Found: C, 67.9%; H, 7.1%; N, 3.4%; Cl, 8.3%.

Example 57

(R)-1-(2-((2-(2-Methylphenyl)-2-(3-methyl-2-thienyl)ethenyl)oxy)ethyl)-3-piperidinecarboxylic acid hydrochloride (R)-1-(2-((2-(2-Methylphenyl)-2-(3-methyl-2-thienyl)ethenyl)oxy)ethyl)-3-piperidinecarboxylic acid ethyl ester (6.0 g, 0.0133 mol, prepared similarly to the method described in Example 50) was dissolved in ethanol (100 ml) and 10 N sodium hydroxide solution (13.3 ml) was introduced. After stirring the solution at room temperature for 3 h water (200 ml) was added, and the ethanol was evaporated under reduced pressure. The aqueous solution was acidified to pH 1 with 2 N hydrochloric acid solution and extracted with dichloromethane (4×150 ml). The combined extracts were dried ($MgSO_4$) and evaporated to a solid, which was recrystallized from methanol/toluene/cyclohexane to give the title compound (4.09 g, 68%) as white crystals.

M.P. 207–212° C.

Calculated for $C_{22}H_{28}ClNO_3S,0.33PhCH_3$: C, 64.6%; H, 6.8%; N, 3.1%; Cl, 7.8%; S, 7.6%; Found: C, 64.6%; H, 6.8%; N, 3.1%; Cl, 7.8%; S, 7.3%.

Example 58

E or Z-(R)-1-(2-((2-(3-Fluorophenyl)-2-(2-methylphenyl)ethenyl)oxy)ethyl)-3-piperidinecarboxylic acid hydrochloride E or Z-(R)-1-(2-((2-(3-Fluorophenyl)-2-(2-methylphenyl)ethenyl)oxy)ethyl)-3-piperidinecarboxylic acid ethyl ester (0.40 g, 0.00097 mol, prepared similarly to the method described in Example 50) was dissolved in ethanol (5 ml) and 12 N sodium hydroxide solution (0.3 ml) was introduced. After stirring the solution at room temperature for 5 h, 37% hydrochloric acid solution was added until the pH was measured as ca. 1. Dichloromethane (250 ml) was introduced, and the resultant precipitate was dissolved by addition of ice portionwise with vigorous stirring. The organic phase was separated, dried ($Na_2SO_4$) and evaporated to a residue, which was co-evaporated with acetone. Recrystallization from acetone provided the title compound (0.10 g, 24%) as a white solid.

M.P. 193–195° C.

Calculated for $C_{23}H_{27}ClFNO_3$: C, 65.8%; H, 6.5%; N, 3.3%; Cl, 8.4%; Found: C, 65.4%; H, 6.6%; N, 3.7%; Cl, 8.2%.

Example 59

Z or E-(R)-1-(2-((2-(3-Fluorophenyl)-2-(2-methylphenyl)ethenyl)oxy)ethyl)-3-piperidinecarboxylic acid hydrochloride Z or E-(R)-1-(2-((2-(3-Fluorophenyl)-2-(2-methylphenyl)ethenyl)oxy)ethyl)-3-piperidinecarboxylic acid ethyl ester (0.50 g, 0.00123 mol, prepared similarly to the method described in Example 50) (opposite geometric isomer of example 58) was dissolved in ethanol (5 ml) and 12 N sodium hydroxide solution (0.3 ml) was introduced. After stirring the solution at room temperature for 5 h, 37% hydrochloric acid solution was added until the pH was measured as ca. 1. Dichloromethane (250 ml) was introduced, and the resultant precipitate was dissolved by addition of ice with vigorous stirring. The organic phase was separated, dried ($Na_2SO_4$) and evaporated to a residue, which was co-evaporated with acetone. Recrystallization from acetone provided the title compound (0.10 g, 20%) as a white solid.

M.P. 193–195° C.

Calculated for $C_{23}H_{27}ClFNO_3$: C, 65.8%; H, 6.5%; N, 3.3%; Cl, 8.4%; Found: C, 65.5%; H, 6.6%; N, 3.5%; Cl, 8.3%.

The compounds in Examples 60–64 were prepared by methods similar to those described in Examples 50–59.

Example 60

(R)-1-(2-((2,2-Bis(4-fluorophenyl)ethenyl)oxy)ethyl)-3-piperidinecarboxylic acid hydrochloride Amorph.

HPLC retention time=22.6 minutes (system D).

$^1$H NMR (400 MHz, DMSO-$d_8$) δ 6.75 (s, 1H); 4.05 (t, 2H).

Example 61

(R)-1 -(2-((2,2-Bis(2-chloro-4-fluorophenyl)ethenyl)oxy)ethyl)-3-piperidinecarboxylic acid hydrochloride

M.P. 180–182° C.

$^1$H NMR (400 MHz, DMSO-d.) 6 6.80 (s, 1H); 4.43 (m, 2H).

Example 62

(R)-1-(2-((2,2-Bis(2,4-difluorophenyl)ethenyl)oxy)ethyl)-3-piperidinecarboxylic acid hydrochloride

M.P. 148–150° C.

Calculated for $C_{22}H_{22}ClF_4NO_3,3/4H_2O$: C, 55.8%; H, 5.0%; N, 3.0%; Found: C, 55.8%; H, 4.9%; N, 2.7%.

Example 63

(R)-1-(2-(((2,4-Difluorophenyl)-2-(2,5-difluorophenyl)ethenyl)oxy)ethyl)-3-piperidinecarboxylic acid hydrochloride

M.P. 162–164° C.

Calculated for $C_{22}H_{22}ClF_4NO_3,1/2H_2O$: C, 56.4%; H, 4.8%; Cl, 7.6%; N, 3.1%; Found: C, 56.2%; H, 5.0%; Cl, 7.5%; N, 2.9%.

Example 64

(R)-1-(2-((2,2-Bis(2,5-difluorophenyl)ethenyl)oxy)ethyl)-3-piperidinecarboxylic acid hydrochloride

M.P. 215–217° C.

Calculated for $C_{22}H_{22}ClF_4NO_3$: C, 57.5%; H, 4.8%; N, 3.1%; Found: C, 57.7%; H, 4.9%; N, 2.9%.

Example 65

(R)-1-(2-((2,2-bis(3-Methyl-2-thienyl)ethenyl)oxy)ethyl)-3-piperidinecarboxylic acid ethyl ester 2-(Triphenylmethoxy)ethanol (3.98 g, 0.013 mol) was dissolved in dry THF (50 ml) and a 2.5 M solution of butyllithium in hexanes (5.5 ml, 0.0137 mol) was added at 0° C. A solution of bromoacetic acid (1.81 g, 13.0 mmol) was separately treated with a 2.5 M solution of butyllithium in hexanes (5.5 ml, 13.7 mmol) at 0° C. before the two solutions were mixed. This reaction mixture was heated at reflux for 68 h, cooled, and water (200 ml) was added. Washing with ethyl acetate was followed by acidification of the aqueous phase with 0.5 M citric acid solution (50 ml).

Extraction with ethyl acetate (2×100 ml) and drying (MgSO$_4$) provided crude (2-(triphenylmethoxy)ethoxy)acetic acid (2.78 g, 58%). This acid was dissolved in dichloro methane (30 ml) and dicyclohexylcarbodiimide (1.72 g, 0.0083 mol) was added, followed by 4-pyrrolidinopyridine (0.11 g, 0.00074 mol) and ethanol (0.89 ml, 2 equiv.) (A. Hassner et al., Tetrahedron Lett. (1978) 4475). The reaction mixture was stirred for 16 h at room temperature and filtered to remove dicyclo-hexylurea. The filtrate was evaporated, and the residue was purified by flash chromatography on silica gel (3×20 cm). Elution with cyclohexane containing 1–3% ethyl acetate provided the desired (2-(triphenylmethoxy)ethoxy)acetic acid ethyl ester (1.5 g, 50%) as an oil.

2-Bromo-3-methylthiophene (1.5 g, 0.0085 mol) and magnesium turnings (0.22 g) were heated gently in dry THF (30 ml) and the reaction rapidly became exothermic. After 0.2 h the reaction mixture was heated at reflux for 0.5 h, and the above ester (1.5 g, 0.0038 mol) was introduced as a solution in THF (20 ml). The mixture was again heated at reflux for 0.5 h, cooled, and ammonium chloride solution (100 ml) was added. Stirring for 0.5 h at room temperature was followed by extraction with ethyl acetate (3×70 ml). The combined extracts were dried (MgSO$_4$) and evaporated. The residue was dissolved in a mixture of 2 N hydrochloric acid (50 ml), THF (50 ml) and ethanol (50 ml) and the solution was heated at 50° C. for 1 h, and basified to pH 9.5 with sodium hydroxide solution. The organic solvents were removed in vacuo and the aqueous residue was extracted with ethyl acetate (3×75 ml). Drying of the combined extracts (MgSO$_4$) and evaporation gave an oil, which was purified by flash chromatography on silica gel (2×15 cm). Elution with cyclohexane/ethyl acetate (9:1) provided 2-(2-(2-hydroxyethoxy)-1-(3-methyl-2-thienyl)ethenyl)-3-methylthiophene (0.54 g, 50%) as a gum.

The above alcohol (0.53 g, 0.0019 mol) was dissolved in dry toluene (20 ml) and the solution was cooled to 0° C. A solution of n-butyllithium (2.5 M in hexanes) (0.9 ml, 0.0023 mol) was introduced, and the reaction mixture was allowed to stand at 0° C. for 1 h after which time a solution of p-toluenesulphonyl chloride (0.47 g, 0.0025 mol) in toluene (10 ml) was added. The mixture was left at room temperature for 20 h and to the resulting tosylate solution was added the (R)-enantiomer of ethyl nipecotate (0.59 g, 0.0038 mol) and powdered, dried potassium carbonate (1.04 g, 0.0075 mol). The temperature was increased to 80° C. and maintained for 50 h. The reaction mixture was cooled and water (50 ml) was added. The toluene phase was separated and the water phase was extracted with ethyl acetate (50 ml). The combined organic extracts was dried (MgSO$_4$) and evaporated to give an oil, which was purified by flash chromatography on silica gel. Elution with cyclohexane/ethyl acetate (19:1–5:1) provided the title compound (0.25 g, 31%) as a gum.

TLC: rf=0.26 (SiO$_2$; heptane/THF=7:3).

Example 66

(R)-1-(2-((2,2-bis(3-Methyl-2-thienyl)ethenyl)oxy)ethyl)-3-piperidinecarboxylic acid (R)-1-(2-((2,2-bis(3-Methyl-2-thienyl)ethenyl)oxy)ethyl) 3-piperidinecarboxylic ethyl ester (420 mg, 1 mmol, Example 65) was dissolved in ethanol (20 ml) and 10 N sodium hydroxide solution (1.00 ml) was introduced. After 3 h at room temperature the pH of the solution was adjusted to 9 with 2 N hydrochloric acid. The ethanol was removed by evaporation and the pH of the solution was adjusted to 2.5. Extraction with dichloromethane (4×15 ml), drying of the combined extracts (MgSO$_4$) and evaporation of the filtrate provided a residue, which was recrystallized from water. This provided the title compound (0.34 g, 84%) as a cream solid.

TLC: rf=0.37 (SiO$_2$, dichloromethane/methanol=1:1).

M.P. 55–70° C.

Calculated for C$_{20}$H$_{25}$NO$_3$S$_2$,3/4H$_2$O: C, 59.3%; H, 6.6%; N, 3.45%; S, 15.8%; Found: C, 59.3%; H, 6.6%; N, 3.5%; S, 15.85%.

Example 67

1-(2-((2,2-bis(2-Methylphenyl)ethenyl)oxy)ethyl)-1,2,5,6-tetrahydro-3-pyridinecarboxylic acid hydrochloride 1-(2-((2,2-bis(2-Methylphenyl)ethenyl)oxy)ethyl)-1,2,5,6-tetrahydro-3-pyridinecarboxylic acid methyl ester (0.70 g, 0.0018 mol, prepared similarly to the method described in Example 65) was dissolved in ethanol (30 ml) and 10 N sodium hydroxide solution (1.79 ml) was introduced. The reaction mixture was stirred at room temperature for 2.5 h and water (100 ml) was added, followed by 2 N hydrochloric acid solution to pH 10. Ethanol was removed by evaporation under reduced pressure, and the aqueous solution was washed with ethyl acetate (20 ml). The aqueous phase was separated, acidified to pH 2 with 2 N hydrochloric acid solution, and extracted with dichloromethane (4×50 ml). The combined extracts was dried (MgSO$_4$) and the residue was crystallized from propanol/toluene to give the title compound (0.53 g, 76%).

M.P. 195–198° C.

Calculated for C$_{24}$H$_{28}$ClNO$_3$: C, 69.65%; H, 6.8%; N, 3.4%; Cl, 8.55%; Found: C, 69.6%; H, 6.85%; N, 3.2%; Cl, 8.1%.

Example 68

(R)-1-(2-((2-(4-Fluoro-2-methylphenyl)-2-(2-methylphenyl)ethenyl)oxy)ethyl)-3-piperidinecarboxylic acid hydrochloride (4-Fluoro-2-methylphenyl)-(2-methylphenyl)acetaldehyde (3.5 g, 0.0144 mol) was dissolved in dry THF (20 ml) and added dropwise to a suspension of sodium hydride (60% oil dispersion) (0.63 g, 0.0158 mol) in dry THF (30 ml). The mixture was stirred at room temperature for 1 h and heated at reflux for 0.5 h. After cooling 1,2-dibromoethane (12.4 ml, 10 equiv.) was added, and the reaction mixture was allowed to stand at room temperature for 192 h. The reaction mixture was filtered and evaporated. The residue was pumped in vacuo, but still contained ca. 30% starting aldehyde, so the above procedure was repeated. The filtered reaction mixture was evaporated and to the residue water (100 ml), saturated brine (100 ml) and ethyl acetate (200 ml) were added. The aqueous phase was separated and washed with ethyl acetate (100 ml).

The combined ethyl acetate extracts was washed with brine (100 ml), dried (MgSO$_4$) and evaporated. The crude 1-(2-(2-Bromo-ethoxy)-1-(2-methylphenyl)ethenyl)-4-fluoro-2-methylbenzene (2.3 g, ca. 46%) was used in the next stage, without further purification.

The above bromo compound (1.15 g, 0.0033 mol), the (R)-enantiomer of ethyl nipecotate hydrochloride (1.92 g, 0.0099 mol) and dried potassium carbonate (2.28 g, 0.0165 mol) were stirred in acetone (100 ml) at reflux temperature for 54 h. The cooled reaction mixture was filtered, and the filtrate was evaporated. The residue was purified by flash chromatography on silica gel (4,5×15 cm) eluting with heptane/ethyl acetate (9:1→4:1) to give (R)-1-(2-((2-(4-Fluoro-2-methyl-phenyl)-2-(2-methylphenyl)-ethenyl)oxy)ethyl)-3-piperidinecarboxylic acid ethyl ester as a gum (0.57 g, 40%).

TLC: rf=0.4 (SiO$_2$, ethyl acetate/heptane=1:1).

The above ester (0.56 g, 0.0013 mol) was dissolved in ethanol (6 ml) and 10 N sodium hydroxide was introduced. After stirring the solution at room temperature for 2 h, water (200 ml) was added, and the ethanol was evaporated under reduced pressure. The aqueous solution was acidified to pH 5 with 2 N hydrochloric acid solution and extracted with dichloromethane (3×100 ml). The combined extracts was dried (MgSO$_4$) and evaporated to a residue which was treated with toluene (20 ml) and the mixture was filtered. To the filtrate, methanol (0.06 ml) and chlorotrimethylsilane (0.20 ml) were added, and the hydrochloride salt precipitated.

Evaporation of the mixture, followed by crystallization of the residue from trace methanol/toluene provided the title compound (0.38 g, 67%).

M.P. softens at 195° C.; melts finally at 210° C.

Calculated for C$_{24}$H$_{29}$ClFNO$_3$: C, 66.4%; H, 6.7%; N, 3.2%; Cl, 8.2%; Found: C, 66.3%; H, 6.8%; N, 3.1%; Cl, 8.4%.

Example 69

1-(2-((2-(4-Fluoro-2-methylphenyl)-2-(2-methylphenyl)ethenyl)oxy)ethyl)-1,2,5,6-tetrahydro-3-pyridinecarboxylic acid hydrochloride 1-(2-((2-(4-Fluoro-2-methylphenyl)-2-(2-methyl-phenyl)ethenyl)oxy)ethyl)-1,2,5,6-tetrahydro-3-pyridinecarboxylic acid methyl ester (0.74 g, 0.0018 mol, prepared similarly to the method described in Example 68) was dissolved in ethanol (15 ml) and 10 N sodium hydroxide solution (1.8 ml) was introduced. After stirring the reaction mixture for 2 h at room temperature TLC indicated that saponification was incomplete, so further 10 N sodium hydroxide solution (1.8 ml) was added, and the reaction mixture was heated for 10 min. at 40° C. Water (400 ml) was added, and the solution was extracted with diethyl ether (100 ml). The aqueous layer was acidified to pH 5 with 2 N hydrochloric acid solution and extracted with dichloromethane (4×50 ml). The combined extracts was dried (MgSO$_4$) and evaporated to a residue (0.61 g) which was dissolved in toluene (50 ml). Methanol (0.2 ml) and chlorotrimethylsilane (0.216 ml) were added, and after mixing, a portion of cyclohexane (ca. 30 ml) was added. After storing this mixture at 4° C. for 18 h, the title compound was collected by filtration (0.60 g, 77%).

M.P. 190–201° C.

Calculated for C$_{24}$H$_{27}$ClFNO$_3$,0.1 PhCH$_3$: C, 67.3%; H, 6.4%; N, 3.2%; Cl, 8.0%; Found: C, 67.1%; H, 6.4%; N, 3.1%; Cl, 8.1%.

Example 70

1-(2-((2,2-bis(3-Fluorophenyl)ethenyl)oxy)ethyl)-1,2,5,6-tetrahydro-3-pyridinecarboxylic acid hydrochloride bis(3-Fluorophenyl)acetaldehyde (4.82 g, 0.0208 mol) was dissolved in dichloromethane (50 ml) and tetra-n-butylammonium bromide (0.67 g, 0.00208 mol) was added. 12 N sodium hydroxide solution (50 ml) and 1,2-dibromoethane (17.9 ml, 0.208 mol) were introduced and the mixture was stirred vigorously at room temperatue for 20 h. Dichloromethane (100 ml) and saturated brine (50 ml) were added, and the phases were separated. The aqueous phase was extracted further with dichloromethane (50 ml) and the combined dichloromethane extracts were washed with water (2×75 ml) and saturated brine (50 ml). Drying of the dichloromethane solution (Na$_2$SO$_4$) and evaporation provided 1-(2-(2-bromoethoxy)-1-(3-fluoro-phenyl) ethenyl)-3-fluorobenzene as an oil (6.66 g, 95%).

TLC: rf=0.71 (SiO$_2$; dichloromethane).

To the above bromide (6.57 g, 0.0194 mol) in acetone (100 ml) was added 1,2,5,6-tetrahydro-3-pyridinecarboxylic acid methyl ester hydrochloride (5.57 g, 0.0291 mol), dried potassium carbonate (8.03 g, 0.0581 mol) and potassium iodide (0.32 g, 0.0019 mol). The suspension was stirred at room temperature for 50 h and filtered. The filtrate was evaporated to an oil (8.2 g) which was dissolved in ethyl acetate (100 ml). Water (40 ml) was added, and the pH of the aqueous phase was adjusted to 4 with 34% aqueous tartaric acid. The aqueous layer was separated, and the organic phase was washed with pH 4 aqueous tartaric acid (20 ml), after which water (40 ml) was added. The pH of the aqueous phase was adjusted to ca. 8 with 2 N sodium hydroxide solution, and the phases were separated. The organic phase was washed with saturated brine (10 ml), dried (Na$_2$SO$_4$) and evaporated to an oil. To this oil in toluene (20 ml) at 45° C. was added methanol (0.68 ml, 0.0167 mol) followed by chlorotrimethylsilane (1.173 g, 0.0156 mol). After stirring at room temperature for 18 h the ester hydrochloride had precipitated, and the suspension was cooled to 0° C. for 2 h. The solid was collected by filtration, washed with cold toluene (15 ml) and suspended in dry diethyl ether (25 ml). Filtration provided 1-(2-((2,2-bis(3-fluorophenyl)ethenyl) oxy)ethyl)-1,2,5,6-tetrahydro-3-pyridinecarboxylic acid methyl ester hydrochloride (3.56 g, 59%) as a white solid.

TLC: rf=0.68 (SiO$_2$; dichloromethane/methanol/acetic acid=20:2:1).

To the above ester hydrochloride (3.50 g, 0.0078 mol) in 96% aqueous ethanol (25 ml) at 5 was added 12 N sodium hydroxide solution (2.1 ml). After stirring the solution at room temperature for 4.5 h, pH was adjusted to 6 with 4 N hydrochloric acid solution, and the mixture was evaporated to an oil. Ethyl acetate (50 ml) and water (20 ml) were added, and the organic phase was separated. The aqueous phase was washed with ethyl acetate (25 ml) and the combined organic phases was washed with saturated brine (10 ml). The ethyl acetate phase was dried (Na$_2$SO$_4$) and the residue was co-evaporated with dichloromethane (3×15 ml). To the residue in toluene (22 ml) at 45° C. was added methanol (0.225 ml) and chlorotrimethylsilane (0.705 ml). On cooling and stirring at room temperature for 18 h the product hydrochloride had precipitated, and the suspension was cooled to 0° C. for 1.5 h. The solid was collected by filtration and dried in vacuo to give the desired product (2.65 g, 80%). Recrystallization from water provided the title compound (1.60 g, 53%).

M.P. 158–159° C.

Calculated for C$_{22}$H$_{22}$ClF$_2$NO$_3$,0.3H$_2$O: C, 61.8%; H, 5.1%; N, 3.3%; Cl, 8.3%; Found: C, 61.5%; H, 5.3%; N, 3.1%; Cl, 8.4%.

Example 71

(R)-1-(2-((2, 2-bis(2-Methylphenyl)ethenyl)oxy)ethyl)-3-piperidinecarboxylic acid hydrochloride (R)-1-(2-((2,2-bis(2-Methylphenyl)ethenyl)oxy)ethyl)-3-piperidinecarboxylic acid ethyl ester (2.20 g, 0.0054 mol, prepared similarly to the method described in Example 70) was dissolved in ethanol (20 ml) and 10 N sodium hydroxide solution (7 ml) was introduced. After stirring the solution at room temperature for 3 h, water (300 ml) was added, and the solution was washed with diethyl ether (100 ml). The aqueous layer was washed further with diethyl ether (100 ml). The pH of the aqueous layer was adjusted to 5 and then extracted with dichloromethane (4×100 ml). The combined extracts was dried ($MgSO_4$), evaporated, and the residue was dissolved in toluene (50 ml). Methanol (0.4 ml) and chlorotrimethylsilane (0.7 ml) were added, and the product precipitated. This solid was collected by filtration and recrystallized from water to give the title compound (1.4 g, 62%).

M.P. 217–226° C.

Calculated for $C_{24}H_{30}ClNO_3$: C, 69.3%; H, 7.3%; N, 3.4%; Cl, 8.5%; Found: C, 69.4%; H, 7.4%; N, 3.3%; Cl, 8.5%.

Example 72

(R)-1-(2-((2,2-bis(4-Fluoro-2-methylphenyl)ethenyl)oxy)ethyl)-3-piperidinecarboxylic acid hydrochloride (R)-1-(2-((2,2-bis(4-Fluoro-2-methylphenyl)ethenyl)oxy)ethyl)-3-piperidinecarboxylic acid ethyl ester (1.72 g, 0.0039 mol, prepared similarly to the method described in Example 70) was dissolved in ethanol (20 ml) and 10 N sodium hydroxide solution (4 ml) was introduced. The solution was stirred at room temperature for 3 h and water (100 ml) was added. The solution was extracted with diethyl ether (2×100 ml) and the aqueous phase was acidified to pH 5 with 2 N hydrochloric acid solution. Extraction with dichloromethane (4×80 ml) and drying of the combined extracts ($MgSO_4$) followed by evaporation gave a residue, which was dissolved in toluene (50 ml). Methanol (0.16 ml) and chlorotrimethylsilane (0.51 ml) were added, and the product precipitated. The mixture was evaporated to a solid and recrystallized from toluene to give the title compound as a white crystalline solid (0.78 g, 44%).

M.P. 175–185° C. (decomp.).

Calculated for $C_{24}H_{28}ClFNO_3$: C, 63.8%; H, 6.2%; N, 3.1%; Cl, 7.8%; Found: C, 64.1%; H, 6.3%; N, 3.0%; Cl, 7.3%.

Example 73

E or Z-(R)-1-(2-((2-(3-Methoxyphenyl)-2-(2-methylphenyl)ethenyl)oxy)ethyl)-3-piperidinecarboxylic acid hydrochloride E or Z-(R)-1-(2-((2-(3-Methoxyphenyl)-2-(2-methylphenyl)ethenyl)oxy)ethyl)-3-piperidinecarboxylic acid ethyl ester (0.50 g, 0.0012 mol, prepared similarly to the method described in Example 70) was dissolved in ethanol (15 ml) and 12 N sodium hydroxide solution (0.2 ml) was introduced. After stirring the solution at room temperature for 6 h, ice (100 g) was added, and the pH of the reaction mixture was adjusted to ca. 7 with 37% hydrochloric acid solution. Dichloromethane (200 ml) was added, and the pH was further adjusted below 2 with 37% hydrochloric acid solution. The dichloromethane phase was dried ($Na_2SO_4$) and evaporated to a solid (0.3 g, 60%).

M.P. 188–192° C.

Calculated for $C_{24}H_{30}ClNO_4,0.25H_2O$: C, 66.0%; H, 7.0%; N, 3.2%; Cl, 8.2%; Found: C, 66.1%; H, 7.2%; N, 3.1%; Cl, 8.1%.

Example 74

E or Z-(R)-1-(2-((2-(3-Methoxyphenyl)-2-(2-methylphenyl)ethenyl)oxy)ethyl)-3-piperidinecarboxylic acid hydrochloride E or Z-(R)-1-(2-((2-(3-Methoxyphenyl)-2-(2-methylphenyl)ethenyl)oxy)ethyl)-3-piperidinecarboxylic acid ethyl ester (0.80 g, 0.0019 mol) (opposite geometric isomer of Example 73) was dissolved in ethanol (15 ml) and 12 N sodium hydroxide solution (0.3 ml) was introduced. After stirring the solution at room temperature for 6 h, ice (50 g) was added, and the pH of the reaction mixture was adjusted to ca. 7 with 37% hydrochloric acid solution. Dichloromethane (200 ml) was added, and the pH was further adjusted below 2 with 37% hydrochloric acid solution. The dichloromethane phase was dried ($Na_2SO_4$) and evaporated to a solid (0.35 g, 44%).

M.P. 198–202° C.

Calculated for $C_{24}H_{30}ClNO_4$: C, 66.7%; H, 7.0%; N, 3.2%; Cl, 8.2%; Found: C, 66.5%; H, 7.2%; N, 3.0%; Cl, 7.6%.

Example 75

1-(2-((2-(3-Methoxyphenyl)-2-(2-methylphenyl)ethenyl)oxy)ethyl)-1,2,5,6-tetrahydro-3-pyridinecarboxylic acid hydrochloride 1-(2-((2-(3-Methoxyphenyl)-2-(2-methylphenyl)ethenyl)oxy)ethyl)-1,2,5,6-tetrahydro-3-pyridinecarboxylic acid methyl ester (1.15 g, 0.0027 mol, prepared similarly to the method described in Example 70) was dissolved in ethanol (15 ml) and 12 N sodium hydroxide solution (0.5 ml) was introduced. After stirring the solution at room temperature for 4 h, ice (30 g) was added, and pH of the reaction mixture was adjusted to ca. 7 with 37% hydrochloric acid solution. Dichloromethane (200 ml) was added, and the pH was further adjusted to ca. 1 with 37% hydrochloric acid solution. Water was added until the solid material was dissolved, and the dichloromethane phase was dried ($Na_2SO_4$) and evaporated to an oil, which was co-evaporated three times with acetone. The residue was triturated with diethyl ether to give the title compound (0.60 g, 52%).

HPLC retention times of 17.1 and 17.6 minutes (System D).

Calculated for $C_{24}H_{28}NO_4,0.8HCl,0.8H_2O$: C, 65.8%; H, 7.0%; N, 3.2%; Cl, 6.3%; Found: C, 65.3%; H, 7.0%; N, 3.2%; Cl, 6.9%.

Example 76

1-(2-((2-(3-Chlorophenyl)-2-(2-methylphenyl)ethenyl)oxy)ethyl)-1,2,5,6-tetrahydro-3-pyridinecarboxylic acid hydrochloride 1-(2-((2-(3-Chlorophenyl)-2-(2-methylphenyl)ethenyl)oxy)ethyl)-1,2,5,6-tetrahydro-3-pyridinecarboxylic methyl ester (0.60 g, 0.0014 mol, prepared similarly to the method described in Example 70) was dissolved in ethanol (5 ml) and 12 N sodium hydroxide solution (0.35 ml) was introduced. After stirring the solution at room temperature for 3 h, 37% hydro chloric acid solution was added, until the pH 1. Dichloromethane (200 ml) was introduced, and the mixture was dried ($Na_2SO_4$), filtered and evaporated to a residue, which was co-evaporated twice with acetone. The residue was recrystallized from acetone/ethyl acetate to give the title compound (0.33 g, 55%) as white crystals.

M.P. 168–170° C.

HPLC retention times 16.12 and 18.42 minutes (System D).

E or Z-1-(2-((2-(3-Chlorophenyl)-2-(2-methylphenyl)ethenyl)oxy)ethyl)-1,2,5,6-tetrahydro-3-pyridinecarboxylic acid hydrochloride E or Z-1-(2-((2-(3-Chlorophenyl)-2-(2-methylphenyl) ethenyl)oxy)ethyl)-1,2,5,6-tetrahydro-3-pyridinecarboxylic acid methyl ester (0.55 g, 0.0013 mol, prepared similarly to the method described in Example 70) was dissolved in ethanol (5 ml) and 12 N sodium hydroxide solution (0.33 ml) was introduced. After stirring the solution at room temperature for 3 h, 37% hydrochloric acid solution was added until pH 1. Dichloromethane (200 ml) was introduced, and the mixture was dried ($Na_2SO_4$), filtered and evaporated to a residue, which was co-evaporated twice with acetone. Recrystallization from acetone/ethyl acetate provided the title compound (0.17 g, 30%) as a white solid.

M.P. 214–215° C.

Calculated for $C_{23}H_{25}Cl_2NO_3$: C, 63.6%; H, 5.8%; N, 3.2%; Cl, 8.2%; Found: C, 63.2%; H, 5.8%; N, 3.4%; Cl, 8.0%.

Example 77

1-(2-((2,2-bis(2-Ethylphenyl)ethenyl)oxy)ethyl)-1,2,5,6-tetrahydro-3-pyridinecarboxylic acid hydrochloride 1-(2-((2,2-bis(2-Ethylphenyl)ethenyl)oxy)ethyl)-1,2,5,6-tetrahydro-3-pyridinecarboxylic acid methyl ester (1.40 g, 0.00323 mol, prepared similarly to the method described in Example 70) was dissolved in ethanol (10 ml) and 12 N sodium hydroxide solution (0.8 ml) was introduced. After stirring the solution at room temperature for 5 h, 37% hydrochloric acid solution was added until the pH was measured as ca. 1. Dichloromethane (250 ml) was introduced, and the mixture was dried ($Na_2SO_4$), filtered and evaporated to a residue, which was co-evaporated with acetone. Recrystallization from acetone provided the title compound (0.80 g, 57%) as a white solid.

M.P. 162–165° C. Calculated for $C_{26}H_{32}ClNO_3$: C, 70.7%; H, 7.3%; N, 3.2%; Cl, 8.0%; Found: C, 70.5%; H, 7.4%; N, 3.6%; Cl, 8.0%.

Example 78

(R)-1-(2-((2,2-bis(2-Ethylphenyl)ethenyl)oxy)ethyl)-3-piperidinecarboxylic acid hydrochloride (R)-1-(2-((2,2-bis(2-Ethylphenyl)ethenyl)oxy)ethyl)-3-piperidinecarboxylic acid ethyl ester (1.20 g, 0.00275 mol, prepared similarly to the method described in Example 70) was dissolved in ethanol (10 ml) and 12 N sodium hydroxide solution (0.7 ml) was introduced. After stirring the solution at room temperature for 5 h, 37% hydrochloric acid solution was added until pH 1. Dichloromethane (250 ml) was introduced, and the mixture was dried ($Na_2SO_4$), filtered and evaporated to a residue, which was co-evaporated with acetone. Recrystallization from acetone provided the title compound (0.85 g, 70%) as a white solid.

M.P. 205–206° C.

Calculated for $C_{26}H_{34}ClNO_3$: C, 70.3%; H, 7.7%; N, 3.2%; Cl, 8.0%; Found: C, 70.0%; H, 7.8%; N, 3.4%; Cl, 7.9%.

Example 79

1-(2-((2,2-Diphenylethenyl)oxy)ethyl)-1,2,5,6-tetrahydro-3-pyridinecarboxylic acid hydrochloride 1-(2-((2,2-Diphenylethenyl)oxy)ethyl)-1,2,5,6-tetrahydro3-pyridinecarboxylic acid methyl ester (4.33 g, 0.0115 mol, prepared similarly to the method described in Example 70) was dissolved in ethanol (50 ml) and 10 N sodium hydroxide solution (11.5 ml) was introduced, followed by water (5 ml). The solution was stirred at room tempeature for 2.5 h and stored at 4° C. for 18 h. 2 N hydrochloric acid solution was added until the pH 2, and the mixture was extracted with dichloromethane (3×60 ml). The combined extracts was dried ($MgSO_4$) and evaporated to give a foam (4.24 g) which was crystallized from 2-propanol to provide the compound (2.32 g, 52%) as a white solid.

M.P. 173–176° C.

Calculated for $C_{22}H_{24}ClNO_3,0.2H_2O$: C, 67.8%; H, 6.3%; N, 3.6%; Cl, 9.1%; Found: C, 67.7%; H, 6.3%; N, 3.4%; Cl, 8.8%.

Example 80

1-(2-((2-(2-Fluorophenyl)-2-(2-methylphenyl)ethenyl)oxy) ethyl)-1,2,5,6-tetrahydro-3-pyridinecarboxylic acid hydrochloride 1-(2-((2-(2-Fluorophenyl)-2-(2-methylphenyl)ethenyl) oxy)ethyl)-1,2,5,6-tetrahydro-3-pyridinecarboxylic acid methyl ester hydrochloride (2.18 g, 0.0049 mol, prepared similarly to the method described in Example 70) was dissolved in ethanol (24 ml) and 12 N sodium hydroxide solution (1.83 ml) was introduced at 5° C. The solution was stirred at room temperature for 2.5 h and stored at −10° C. for 18 h. The reaction mixture was evaporated to a residue after pH had been adjusted to 6.5 with 4 N hydrochloric acid solution. Water (20 ml) and ethyl acetate (50 ml) were added, the aqueous layer was separated and extracted again with ethyl acetate (25 ml). The combined ethyl acetate extracts was washed with saturated brine (40 ml), dried ($MgSO_4$) and evaporated to a residue, which was co-evaporated with dichloromethane (3×40 ml). The residue (1.9 g) was dissolved in toluene (15 ml) and methanol (0.2 ml) was introduced followed by chlorotrimethylsilane (0.62 ml). The mixture was stirred for 18 h at room temperature and cooled to 0° C. for 2 h. The title compound (1.9 g, 91%) was obtained as white crystals.

M.P. 183–185° C.

Calculated for $C_{23}H_{24}FNO_3,1.25HCl$: C, 64.7%; H, 6.0%; N, 3.3%; Cl, 10.4%; Found: C, 64.3%; H, 6.0%; N, 3.1%; Cl, 9.9%.

Example 81

1-(2-((2-(2,4-Dichlorophenyl)-2-(2-methylphenyl)ethenyl) oxy)ethyl)-1,2,5,6-tetrahydro-3-pyridinecarboxylic acid hydrochloride 1-(2-((2-(2,4-Dichlorophenyl)-2-(2-methylphenyl) ethenyl)oxy)ethyl)-1,2,5,6-tetrahydro-3-pyridinecarboxylic acid methyl ester hydrochloride (2.76 g, 0.0055 mol, prepared similarly to the method described in Example 70) was dissolved in ethanol (30 ml) and 12 N sodium hydroxide solution (2.1 ml) was introduced at 50° C. The solution was stirred at room temperature for 3 h and stored at −10° C. for 18 h. The reaction mixture was evaporated to a residue after the pH had been adjusted to 6.5 with 4 N hydrochloric acid solution. Water (50 ml), ethyl acetate (50 ml) and dichloromethane (50 ml) were added and the organic phase was separated. The aqueous phase was further extracted with ethyl acetate (50 ml), dichloromethane (50 ml) and the combined organic extracts was dried ($MgSO_4$) and evaporated. The resultant residue was co-evaporated twice with methanol and twice with carbontetrachloride to give a foam (2.7 g). This foam was dissolved in toluene (20 ml) and methanol (0.23 ml) was introduced followed by chlorotrimethylsilane (0.71 ml) at 35° C. The product began to crystallize at around 40° C. and the mixture was stirred for 18 h at room temperature and cooled to 0° C. for 2 h. The title compound (2.20 g, 84%) was obtained as white crystals.

M.P. 187–1900 (decomp.).

Calculated for $C_{23}H_{23}Cl_2NO_3,1.1HCl$: C, 58.5%; H, 5.2%; N, 3.0%; Cl 8.3%; Found: C, 58.2%; H, 5.1%; N, 2.8%; Cl, 8.1%.

Example 82
1-(2-((2,2-bis(2-Chlorophenyl)ethenyl)oxy)ethyl)-1,2,5,6-tetrahydro-3-pyridinecarboxylic acid hydrochloride 1-(2-((2,2-bis(2-Chlorophenyl)ethenyl)oxy)ethyl)-1,2,5,6-tetrahydro-3-pyridinecarboxylic acid methyl ester hydrochloride (3.60 g, 0.0075 mol, prepared similarly to the method described in Example 70) was dissolved in ethanol (40 ml) and 12 N sodium hydroxide solution (2.5 ml) was introduced at 5° C. The solution was stirred at room temperature for 6 h and stored at −10° C. for 18 h. The reaction mixture was evaporated to a residue after the pH had been adjusted to 6.5 with 4 N hydrochloric acid solution. Water (10 ml) and ethyl acetate (50 ml) were added, and the organic phase was separated. The ethyl acetate phase was washed with saturated brine (10 ml), dried ($Na_2SO_4$) and evaporated. The resultant residue was evaporated to give a foam (3.1 g). This foam was dissolved in toluene (23 ml) and methanol (0.30 ml) was introduced followed by chlorotrimethylsilane (0.94 ml) at 35° C. The product began to crystallize at around 40° C. and the mixture was stirred for 48 h at room temperature and cooled to 0° C. for 2 h. The title compound (2.5 g, 73%) was obtained as white crystals.

TLC: rf=0.16 ($SiO_2$; dichloromethane/methanol/acetic acid=80:8:4).

M.P. 200–203° C. (decomp.).

Example 83
1-(2-((2,2-bis(4-Fluoro-2-methylphenyl)ethenyl)oxy)ethyl)-1,2,5,6-tetrahydro-3-pyridinecarboxylic acid hydrochloride 1-(2-((2,2-bis(4-Fluoro-2-methylphenyl)ethenyl)oxy)ethyl)-1,2,5,6-tetrahydro-3-pyridinecarboxylic acid ethyl ester (1.27 g, 0.0029 mol, prepared similarly to the method described in Example 70) was dissolved in ethanol (30 ml) and 10 N sodium hydroxide solution (10 ml) was introduced. After stirring the solution at room temperature for 1 h, water (500 ml) was added and the solution was washed with diethyl ether (2×100 ml). pH of the aqueous layer was adjusted to 5 using 2 N hydrochloric acid solution and extracted with dichloromethane (3×200 ml). The combined extracts was dried ($MgSO_4$) and the solvent evaporated. The residue was dissolved in toluene (50 ml), and added to a solution of chlorotrimethylsilane (0.47 ml) and methanol (0.15 ml) in toluene (100 ml). The precipitate was collected by filtration after the mixture had been stored at room temperature for 18 h. The solid formed was recrystallized three times from toluene/trace methanol to give the title compound (0.85 g, 65%) as white crystals.

M.P. 195–209° C. (decomp.).

Calculated for $C_{24}H_{26}ClF_2NO_3 \cdot 0.2H_2O$: C, 63.6%; H, 5.9%; N, 3.1%; Cl, 7.9%; Found: C, 63.6%; H, 5.9%; N, 3.1%; Cl, 7.9%. 20

Example 84
(R)-1-(2-((2-(2-Chlorophenyl)-2-(2-methylphenyl)ethenyl)oxy)ethyl)-3-piperidinecarboxylic acid hydrochloride (R)-1-(2-((2-(2-Chlorophenyl)-2-(2-methylphenyl)ethenyl)oxy)ethyl)-3-piperidinecarboxylic acid ethyl ester (4.1 g, 0.0096 mol, prepared similarly to the method described in Example 70) was dissolved in ethanol (100 ml) and 18 N sodium hydroxide solution (10 ml) was introduced. After stirring the solution at room temperature for 1 h water (500 ml) was added, and the solution was washed with diethyl ether (2×100 ml). pH of the aqueous phase was adjusted to 1 using 2 N hydrochloric acid solution and extracted with dichloromethane (4×200 ml). The combined extracts was dried ($MgSO_4$), evaporated and the residue was crystallized from toluene/trace methanol to provide the title compound (3.47 g, 87%) as a white crystalline solid.

M.P. 231–234° C.

Calculated for $C_{23}H_{27}Cl_2NO_3$: C, 63.3%; H, 6.2%; N, 3.2%; Cl, 16.3%; Found: C, 63.2%; H, 6.4%; N, 3.1%; Cl, 16.3%.

Example 85
1-(2-(((2-(2-Chlorophenyl)-2-(2-methylphenyl)ethenyl)oxy)ethyl)-1,2,5,6-tetrahydro-3-pyridinecarboxylic acid hydrochloride 1-(2-(((2-(2-Chlorophenyl)-2-(2-methylphenyl)ethenyl)oxy)ethyl)-1,2,5,6-tetrahydro-3-pyridinecarboxylic acid ethyl ester (3.35 g, 0.0079 mol, prepared similarly to the method described in Example 70) was dissolved in ethanol (100 ml) and 18 N sodium hydroxide solution (10 ml) was introduced. After stirring the solution at room temperature for 2 h, water (500 ml) was added, and the reaction mixture was washed with diethyl ether (2×100 ml). The pH of the aqueous phase was adjusted to 1 using 25 2 N hydrochloric acid solution and it was extracted with dichloromethane (4×100 ml). The combined extracts was dried ($MgSO_4$), evaporated and the solid residue was recrystallized from toluene/trace methanol to provide the title compound (2.2 g, 64%) as a white crystalline solid.

M.P. 196–198° C.

Calculated for $C_{23}H_{25}Cl_2NO_3$: C, 63.6%; H, 5.8%; N, 3.2%; Cl, 16.3%; Found: C, 63.6%; H, 5.9%; N, 3.1%; Cl, 16.3%.

Example 86
(R)-1-(3-((2,2-bis(4-Fluorophenyl)ethenyl)oxy)-1-propyl)-3-piperidinecarboxylic acid hydrochloride (R)-1-(3-((2,2-bis(4-Fluorophenyl)ethenyl)oxy)-1-propyl)-3-piperidinecarboxylic acid ethyl ester tartrate (3.8 g, 0.0065 mol, prepared similarly to the method described in Example 70) was dissolved in ethanol (25 ml) and 12 N sodium hydroxide solution (2.2 ml) was introduced at 5° C. After stirring the solution at room temperature for 4.8 h, pH of the reaction mixture was adjusted to ca. 7 with 4 N hydrochloric acid solution, and the mixture was evaporated to a residue in vacuo. Water (25 ml) was added, and the mixture was extracted with dichloromethane (3×50 ml). The combined exctacts were dried ($MgSO_4$) and evaporated to a foam, which was dissolved in toluene (1.5 ml) and warmed to 40° C. Methanol (0.27 ml) was introduced followed by chlorotrimethylsilane (0.83 ml). The product precipitated slowly, and after the suspension had been allowed to stand for 18 h at room temperature it was collected by filtration. The title compound (2.9 g, 100%) was obtained as white crystals.

M.P. 177–180° C.

HPLC retention time 12.55 minutes (System C).

Example 87
(R)-1-(2-((2,2-Bis(2-chlorophenyl)ethenyl)oxy)ethyl)-3-piperidinecarboxylic acid hydrochloride

M.P. 243–245° C.

Calculated for $C_{22}H_{24}Cl_3NO_3$: C, 57.8%; H, 5.3%; Cl, 23.4%; N, 3.1%; Found: C, 57.9%; H, 5.4%; Cl, 23.4%; N, 2.9%.

Example 88
(R)-1-(2-((2,2-Diphenylethyl)oxy)ethyl)-3-piperidinecarboxylic acid hydrochloride (R)-1-(2-((2,2-Diphenylethyl)oxy)ethyl)-3-piperidinecarboxylic acid hydrochloride (2.0 g, 5.2 mmol) was dissolved in a mixture of methanol (50 ml) and water (50 ml) at 40° C. and stirred under an atmosphere of hydrogen for 2 h at room temperature in the presence of 10% palladium on carbon catalyst (52% aqueous paste) for 1 h and then filtered. The filtrate was evaporated to dryness leaving a residue, which was crystallised from acetone to give the title compound (1.6 g, 80%) as a solid.

M.P. 171–173° C.

$^1$H NMR (400 MHz, DMSO-d$_6$) δ 4.30 (t, 1H); 4.03 (d, 2H).

The compounds in Examples 89–93 were prepared by a method similar to that described in Example 88.

Example 89

(R)-1-(2-(2,2-Bis(2,4-difluorophenyl)ethoxy)ethyl)-3-piperidinecarboxylic acid hydrochloride

M.P. 159–160° C.

$^1$H NMR (400 MHz, DMSO-d$_6$) δ 4.73 (t, 1H); 4.00 (d, 2H).

Example 90

(R)-1-(2-(Bis(4-fluoro-2-methylphenyl)ethoxy)ethyl)-3-piperidinecarboxylic acid hydrochloride

M.P. 206–208° C.

$^1$H NMR (400 MHz, DMSO-d$_6$) δ 4.45 (t, 1H); 3.83 (m, 2×2H).

Example 91

(R)-1-(2-(2,2-Bis(2,5-difluorophenyl)ethoxy)ethyl)-3-piperidinecarboxylic acid hydrochloride

M.P. 200–202° C.

Calculated for C$_{23}$H$_{24}$ClF$_4$NO$_3$: C, 57.2%; H, 5.2%; N, 3.0%; Found: C, 57.2%; H, 5.3%; N, 2.9%.

Example 92

(R)-1-(2-((2,2-Bis(3-chlorophenyl)ethenyl)oxy)ethyl)-3-piperidinecarboxylic acid hydrochloride

M.P. 232–233° C.

Calculated for C$_{22}$H$_{24}$Cl$_3$NO$_3$: C, 57.9%; H, 5.3%; Cl, 7.8%; N, 3.1%; Found: C, 57.6%; H, 5.4%; Cl, 7.5%; N, 2.8%.

Example 93

(R)-1-(3-(2,2-Diphenylethoxy)-1-propyl)-3-piperidinecarboxylic acid hydrochloride Amorph.

Calculated for C$_{23}$H$_{30}$ClNO$_3$: C, 68.4%; H, 7.5%; N, 3.5%; Found: C, 68.7%; H, 7.8%; N, 3.2%.

$^1$H NMR (400 MHz, DMSO-d$_8$) δ 4.25 (t, 1H); 3.92 (d, 2H).

Example 94

(R)-1-(2-(((Diphenylmethylene)amino)oxy)ethyl)-3-piperidinecarboxylic acid hydrochloride The (R)-enantiomer of ethyl nipecotate (100 g, 0.64 mol) (A. M. Akkerman et al., Rec.Trav.Chim., 70 (1951), 899; G. Bettoni et al., Gazz.Chim.Ital., 102 (1972) 189) was mixed in dry acetone (300 ml) with 2-bromoethanol (85 g, 0.68 mol), dried, powdered potassium carbonate (177 g, 1.28 mol) and potassium iodide (21.6 g, 0.13 mol). The reaction mixture was stirred at room temperature for 18 h and at reflux for 24 h. Filtration and evaporation of the filtrate gave an oil which was purified by distillation in vacuo (110–115° C., 0.1 mmHg), yield 72 g (56%).

TLC: rf=0.20 (SiO$_2$; dichloromethane/methanol=19:1).

The above alcohol (19.9 g, 0.099 mol) was dissolved in toluene (125 ml). A solution of thionyl chloride (14.2 g, 0.12 mol) in toluene (50 ml) was added dropwise and the reaction mixture was stirred at room temperature for 2 h. Cooling in an icebath followed by filtration provided the (R)-N-(2-chloroethyl)nipecotic acid ethyl ester as a solid. A sample was recrystallized from 2-propanol.

M.P. 187.5–194.5° C.

To the above ester hydrochloride (2.56 g, 10 mmol), dried, powdered potassium carbonate (5.53 g, 40 mmol), acetone (200 ml) and benzophenone oxime (3.94 g, 20 mmol) was added. The suspension was heated at reflux for 96 h, cooled and filtered. The solvent was removed from the filtrate in vacuo to give a residue. Water (100 ml) and ethyl acetate (100 ml) were introduced. The aqueous layer was separated and further extracted with ethyl acetate (2×100 ml). The combined organic extracts were dried (MgSO$_4$) and evaporated to give a brown oil (6.2 g). This oil was purified by column chromatography eluting with a mixture of cyclohexane and ethyl acetate (5:1) to provide the (R)-1-(2-(((diphenylmethylene)amino)oxy)ethyl)-3-piperidinecarboxylic acid ethyl ester (2.66 g, 70%) as a gum.

TLC: rf=0.067 (SiO$_2$; cyclohexane/ethyl acetate=5:1).

The above ester (2.66 g, 6.99 mmol) was dissolved in ethanol (100 ml) and 10 N sodium hydroxide solution (6.99 ml) was introduced. After 2 h at room temperature the solution was cooled in an ice bath and the pH was adjusted to 3 with 4 N hydrochloric acid. Extraction with dichloromethane (3×50 ml), drying (MgSO$_4$) of the combined fractions and evaporation provided the title compound as a hydrate (1.3 g, 53%).

M.P. 241–242° C.

By the above general procedure the following oxime derivatives were prepared:

Example 95

(R)-1-(2-(((Bis(2-chloro-4-fluorophenyl)methylene)amino)oxy)ethyl)-3-piperidinecarboxylic acid hydrochloride

M.P. 186–187° C.

Calculated for C$_{21}$H$_{21}$Cl$_3$N$_2$O$_3$: C, 51.1%; H, 4.3%; N, 5.7%; Found: C, 51.2%; H, 4.4%; N, 5.8%.

Example 96

(R)-1-(2-(((Bis(2,4-diflourophenyl)methylene)amino)oxy)ethyl)-3-piperidinecarboxylic acid hydrochloride Amorph.

Calculated for C$_{21}$H$_{21}$ClF$_4$N$_2$O$_3$: C, 54.7%; H, 4.6%; N, 6.1%; Found: C, 55.1%; H, 4.8%; N, 6.0%.

$^1$H NMR (400 MHz, DMSO-d$_6$) δ 4.43 (m, 2H).

Example 97

(R)-1-(2-((((2,4-Difluorophenyl)-(2,5-difluorophenyl)methylene)amino)oxy)ethyl)-3-piperidinecarboxylic acid hydrochloride Amorph.

Calculated for C$_{21}$H$_{21}$ClF$_4$N$_2$O$_3$,1/2H$_2$O: C, 53.7%; H, 4.7%; N, 6.0; Found: C, 53.5%; H, 4.8%; N, 5.7%.

$^1$H NMR (400 MHz, DMSO-d$_6$) δ 4.60 (m, 2H).

Example 98

(R)-1-(2-(((Bis(3,5-difluorophenyl)methylene)amino)oxy)ethyl)-3-piperidinecarboxylic acid hydrochloride

M.P. 171–174° C.

$^1$H NMR (400 MHz, DMSO-d$_6$) δ 4.60 (m, 2H).

Example 99

(R)-1-(2-((((2-Fluorophenyl)-(2-methylphenyl)methylene)amino)oxy)ethyl)-3-piperidinecarboxylic acid hydrochloride

M.P. 164–166° C.

Calculated for C$_{22}$H$_{26}$ClFN$_2$O$_3$,1/4H$_2$O: C, 62.1%; H, 6.3%; N, 6.6%; Cl, 8.3%; Found: C, 62.0%; H, 6.3%; N, 6.3%; Cl, 8.5%.

Example 100
(R)-1-(2-(((Bis(2,5-difluorophenyl)methylene)amino)oxy) ethyl)-3-piperidinecarboxylic acid hydrochloride
Amorph.
HPLC retention time 16.60 minutes (System D).
$^1$H NMR (400 MHz, DMSO-$d_6$) δ 4.34 (m, 2H).

Example 101
E or Z-(R)-1-(2-((((2-Methylphenyl)-(3-methyl-2-thienyl-methylene)amino)oxy)ethyl)-3-piperidinecarboxylic acid hydrochloride
TLC: rf=0.30 (SiO$_2$; dichloromethane/methanol=1:1).

Example 102
(R)-1-(2-(((Bis(3-methyl-2-thienyl)methylene)amino)oxy) ethyl)-3-piperidinecarboxylic acid hydrochloride
M.P. 45° C.

Example 103
(R)-1-(2-((((2-Ethylphenyl)-(3-methyl-2-thienyl) methylene)amino)oxy)ethyl)-3-piperidinecarboxylic acid hydrochloride
M.P. 202–203° C.

Example 104
(R)-1-(2-((((3-Methyl-2-thienyl)-2-thienylmethylene) amino)oxy)ethyl)-3-piperidinecarboxylic acid hydrochloride
M.P. 210–216° C.

Example 105
(R)-1-(2-((((3-Methoxyphenyl)-(3-methyl-2-thienyl) methylene)amino)oxy)ethyl)-3-piperidinecarboxylic acid hydrochloride
TLC: rf=0.3 (SiO$_2$; dichloromethane/methanol=1:1).

Example 106
(R)-1-(2-((((2-Methylphenyl)-(1-methyl-1H-pyrrol-2-yl) methylene)amino)oxy)ethyl)-3-piperidinecarboxylic acid
TLC: rf=0.29 (SiO$_2$; dichloromethane/methanol=1:1).

Example 107
(R)-1-(2-((((1-Methyl-1H-pyrrol-2-yl)phenylmethylene) amino)-oxy)ethyl)-3-piperidinecarboxylic acid hydrochloride
M.P. 221.5–225° C.

Example 108
E or Z (R)-1-(2-((((3-Methoxyphenyl)-(4-methyl-2-thienyl)-methylene)amino)oxy)ethyl)-3-piperidinecarboxylic acid hydrochloride
TLC: rf=0.31 (SiO$_2$; dichloromethane/methanol=1:1).

Example 109
E or Z-(R)-1-(2-((((2-Methylphenyl)-(3-methyl-2-thienyl) methylene)amino)oxy)ethyl)-3-piperidinecarboxylic acid hydrochloride
TLC: rf=0.32 (SiO$_2$; dichloromethane/methanol=1:1).

Example 110
E or Z-(R)-1-(2-((((2-Methyl-2H-1,2,4-triazol-3-yl)-2-thienyl-methylene)amino)oxy)ethyl)-3-piperidinecarboxylic acid hydrochloride
TLC: rf=0.90 (reversed phase, Whatman KCl 8F, methanol/water=4:1).

Example 111
E or Z-(R)-1-(2-((((2-Methyl-2H-1,2,4-triazol-3-yl)-2-thienyl-methylene)amino)oxy)ethyl)-3-piperidinecarboxylic acid hydrochloride
TLC: rf=0.90 (reversed phase, Whatman KCl 8F, methanol/water=4:1).

Example 112
(R)-1-(2-((((3-Azidophenyl)(3-methyl-2-thienyl) methylene)amino)oxy)ethyl)-3-piperidinecarboxylic acid hydrochloride
TLC: rf=0.20 (SiO$_2$; methanol).

Example 113
E or Z-(R)-1-(2-((((2-Methylphenyl)-(3-methyl-2-thienyl) methylene)amino)oxy)ethyl)-3-piperidinecarboxylic acid ethyl ester
TLC: rf=0.35 (SiO$_2$; cyclohexane/ethyl acetate=1:1).

Example 114
(R)-1-(2-((((2-Azidophenyl)phenylmethylene)amino)oxy) ethyl)-3-piperidinecarboxylic acid hydrochloride
TLC: rf=0.14 (SiO$_2$; dichloromethane/methanol=1:1).

Example 115
(S)-1-(2-(((Diphenylmethylene)amino)oxy)ethyl)-3-piperidinecarboxylic acid hydrochloride
TLC: rf=0.38 (SiO$_2$; dichloromethane/methanol=1:1).

Example 116
(R)-1-(2-(((Bis(3-ethyl-2-thienyl)methylene)amino)oxy) ethyl)-3-piperidinecarboxylic acid hydrochloride
TLC: rf=0.30 (SiO$_2$; dichloromethane/methanol=1:1).

Example 117
(R)-1-(2-((((2,4-Dichlorophenyl)(3-methyl-2-thienyl) methylene)amino)oxy)ethyl)-3-piperidinecarboxylic acid hydrochloride
TLC: rf=0.52 (SiO$_2$; dichloromethane/methanol=1:1).

Example 118
(R)-1-(2-((((3-Methoxyphenyl)phenylmethylene)amino) oxy)ethyl)-3 -piperidinecarboxylic acid hydrochloride
M.P. 180–185° C.

Example 119
(R)-1-(2-((((2-Methylphenyl)(3-methoxyphenyl)methylene) amino)oxy)ethyl)-3-piperidinecarboxylic acid hydrochloride
M.P. 185–190° C.

Example 120
(R)-1-(2-(((Bis(4-chloro-2-methylphenyl)methylene) amino)oxy)ethyl)-3-piperidinecarboxylic acid hydrochloride
M.P. 230–232° C.

Example 121
E or Z-(R)-1-(2-((((2-Methylphenyl)-(3-methyl-2-thienyl) methylene)amino)oxy)ethyl)-3-piperidinecarboxylic acid ethyl ester hydrochloride
M.P. 124–125.5° C.

Example 122
(R)-1-(2-((((4-Chloro-2-methylphenyl)-(3-methyl-2-thienyl)methylene)amino)oxy)ethyl)-3-piperidinecarboxylic acid hydrochloride
M.P. 170–175° C.

Example 123

(R)-1-(2-(((Bis(2-methylphenyl)methylene)amino)oxy)ethyl)-3-piperidinecarboxylic acid hydrochloride TLC: rf=0.49 (SiO$_2$; dichloromethane/methanol=1:1).

Using (R/S)-N-(2-chloroethyl)nipecotic acid ethyl ester as a starting material the following (R,S)-enantiomeric mixtures were prepared (according to the method described in Example 94):

Example 124

1-(2-(((Diphenylmethylene)amino)oxy)ethyl)-3-piperidinecarboxylic acid hydrochloride

M.P. 234–235° C.

Example 125

E or Z-1-(2-((((2-Methylphenyl)-(3-methyl-2-thienyl)methylene)amino)oxy)ethyl)-3-piperidinecarboxylic acid hydrochloride TLC: rf=0.30 (SiO$_2$; dichloromethane/methanol=1:1).

Example 126

1-(2-((((1-Methyl-1H-imidazol-2-yl)phenylmethylene)amino)oxy)ethyl)3-piperidinecarboxylic acid TLC: rf=0.07 (SiO$_2$; methanol/dichloromethane=1:1).

Example 127

1-(2-(((Phenyl-2-pyridinylmethylene)amino)oxy)ethyl)-3-piperidinecarboxylic acid hydrochloride

M.P. 61–63° C.

Example 128

1-(2-(((Phenyl-1H-pyrrol-2-ylmethylene)amino)oxy)ethyl)-3-piperidinecarboxylic acid hydrochloride

M.P. 172.5–176° C.

Example 129

1-(2-(((Bis(4-chlorophenyl)methylene)amino)oxy)ethyl)-3-piperidinecarboxylic acid hydrochloride TLC: rf=0.25 (SiO$_2$; dichloromethane/methanol=1:1).

Example 130

1-(2-((((4-Azidophenyl)-phenylmethylene)amino)oxy)ethyl)-3-piperidinecarboxylic acid hydrochloride TLC: rf=0.30 (SiO$_2$; methanol).

Example 131

1-(2-((((4-Fluorophenyl)phenylmethylene)amino)oxy)ethyl)-3-piperidinecarboxylic acid hydrochloride TLC: rf=0.35 (SiO$_2$; dichloromethane/methanol=1:1).

Example 132

1-(2-((((2-Chlorophenyl)phenylmethylene)amino)oxy)ethyl)-3-piperidinecarboxylic acid hydrochloride TLC: rf=0.35 (SiO$_2$; dichloromethane/methanol=1:1).

Example 133

1-(2-((((4-Chloro-2-methylphenyl)-(2-methylphenyl)methylene)amino)oxy)ethyl)-3-piperidinecarboxylic acid hydrochloride TLC: rf=0.33 (SiO$_2$; dichloromethane/methanol=1:1).

Example 134

1-(2-((((3-Azidophenyl)phenylmethylene)amino)oxy)ethyl)-3-piperidinecarboxylic acid hydrochloride TLC: rf=0.30 (SiO$_2$; methanol).

Example 135

1-(2-((((3-Nitrophenyl)phenylmethylene)amino)oxy)ethyl)-3-piperidinecarboxylic acid hydrochloride TLC: rf=0.30 (SiO$_2$; methanol).

Example 136

1-(2-(((Bis(2-hydroxyphenyl)methylene)amino)oxy)ethyl)-3-piperidinecarbocylic acid hydrochloride

M.P. 215–220° C.

Example 137

1-(2-(((Bis(3-methoxyphenyl)methylene)amino)oxy)ethyl)-3-piperidinecarboxylic acid hydrochloride TLC: rf=0.31 (SiO$_2$; dichloromethane/methanol=1:1).

Example 138

1-(2-((((2,4-Dichlorophenyl)-(3-methyl-2-thienyl)methylene)amino)oxy)ethyl)-3-piperidinecarboxylic acid hydrochloride TLC: rf=0.30 (SiO$_2$; dichloromethane/methanol=1:1).

Example 139

(R)-1-(2-((((2-Chlorophenyl)-(2-methylphenyl)methylene)amino)oxy)ethyl)-3-piperidinecarboxylic acid hydrochloride TLC: rf=0.57 (SiO$_2$; dichloromethane/methanol=1:1).

Example 140

1-(2-((((2-Methylphenyl)(3-methylphenyl)methylene)amino)oxy)ethyl)-3-piperidinecarboxylic acid hydrochloride

M.P. 174–176° C.

Example 141

1-(2-((((4-Methyl-2-thienyl)-(2-tolyl)methylene)amino)oxy)ethyl)-3-piperidinecarboxylic acid hydrochloride

M.P. 209–211° C.

Example 142

1-(2-((((3-Hydroxyphenyl)phenylmethylene)amino)oxy)ethyl)-3-piperidinecarboxylic acid hydrochloride TLC: rf=0.40 (SiO$_2$; methanol).

Example 143

1-(2-(((Bis(2-tolyl)methylene)amino)oxy)-1-propyl)-3-piperidinecarboxylic acid

Tlc, rf=0.52 (reversed phase, Whatman KC18F, methanol/water 4/1).

Example 144

1-(2-(((Diphenylmethylene)amino)oxy)ethyl)-1,2,5,6-tetrahydro-3-pyridinecarboxylic acid hemihydrochloride Benzophenone oxime (3.94 g, 20 mmol), 1-bromo-2-chloroethane (28.7 g, 200 mmol) and dried, powdered potassium carbonate (5.53 g, 80 mmol) in acetone (60 ml) were heated at reflux for 72 h. The reaction mixture was cooled and filtered and the filtrate was evaporated to an oily residue which was purified by column chromatography (eluting with heptane/ethyl acetate=19:1) to provide diphenylmethanone 0-(2-chloroethyl)oxime (3.82 g, 73%) as an oil.

TLC: rf=0.36 (SiO$_2$; heptane/ethyl acetate=9:1).

The above chloroethyloxime (1.3 g, 5 mmol) was dissolved in acetone (25 ml) and guvacine methyl ester hydrochloride (1.8 g, lo mmol) powdered, dried potassium carbonate (2.1 g, 15 mmol) and potassium iodide (0.75 g, 5 mmol) were introduced. The reaction mixture was heated at reflux for 18 h and cooled. Filtration and evaporation of the filtrate provided an oil which was purified by column chromatography on silica gel, eluting with cyclohexene/ethyl acetate (2:1) to provide 1-(2-(((Diphenylmethylene)amino)oxy)ethyl)-1,2,5,6-tetrahydro-3-pyridinecarboxylic acid methyl ester (0.87 g, 48%) as a gum.

TLC: rf=0.30 (SiO$_2$; heptane/ethyl acetate=1:1).

The above methyl ester (0.81 g, 2.39 mmol) was dissolved in ethanol (25 ml) And 10 N sodium hydroxide solution (2.39 ml) was added. The solution was stirred at room temperature for 4 h and acidified to pH 2 with 2 N hydrochloric acid. The liquid was extracted with dichloromethane (3×50 ml) and the combined organic extracts was dried (MgSO$_4$).

Evaporation of the solvent gave a gum which was freeze-dried to give the title compound (0.83 g, 89%) as a hemi-hydrochloride.

TLC: rf=0.40 (SiO$_2$; dichloromethane/methanol=1:1).

Calculated for $C_{21}H_{22}N_2O_3, 1/2HCl, H_2O$: C, 65.2%; H, 6.4%; N, 7.2%; Cl, 4.6%; Found: C, 65.6%; H, 6.3%; N, 7.05%; Cl, 4.9%.

By the above general procedure (Example 144) the following oxime derivatives were prepared:

Example 145

(R)-1-(2-((((2,4-Dichlorophenyl)-(3-methoxyphenyl)methylene)amino)oxy)ethyl)-3-piperidinecarboxylic acid hydrochloride Foam.

Calculated for $C_{22}H_{25}Cl_3N_2O_{4,1}$ 1/2H$_2$O: C, 53.2%; H, 5.3%; N, 5.6%; Found: C, 53.0%; H, 5.4%; N, 5.3%.

$^1$H NMR (400 MHz, DMSO-d$_6$) δ 4.50 (s, 2H); 3.78 (s, 3H).

Example 146

(R)-1-(2-(((Bis(3-chlorophenyl)methylene)amino)oxy)ethyl)-3-piperidinecarboxylic acid hydrochloride Amorph.

Calculated for $C_{21}H_{23}Cl_3N_2O_3, 1/2H_2O$: C, 54.0%; H, 5.2%; N, 6.0%; Found: C, 54.0%; H, 5.2%; N, 5.7%.

$^1$H NMR (200 MHz, DMSO-d$_6$) δ 4.55 (m, 2H).

Example 147

E or Z-(R)-1-(2-((((2-Chloro-4-fluorophenyl)-(3-fluorophenyl)methylene)amino)oxy)ethyl)-3-piperidinecarboxylic acid hydrochloride

M.P. 166–168° C.

Calculated for $C_{23}H_{23}ClF_2N_2O_3$: C, 54.9%; H, 4.8%; N, 6.1%; Found: C, 55.1%; H, 5.0%; N, 6.0%.

Example 148

E- or Z-(R)-1-(2-((((2-Fluorophenyl)-(4-fluorophenyl)methylene)amino)oxy)ethyl)-3-piperidinecarboxylic acid hydrochloride

M.P. 185–188° C.

Calculated for $C_{21}H_{23}ClF_2N_2O_3$: C, 59.4%; H, 5.5%; N, 6.6%; Found: C, 59.5%; H, 5.5%; N, 6.5%.

Example 149

(R)-1-(2-(((Bis(4-fluoro-2-methylphenyl)methylene)amino)oxy)ethyl)-3-pyrrolidine-acetic acid hydrochloride Amorph.

HPLC retention time=23.8 minutes (system D).

$^1$H NMR (400 MHz, DMSO-d$_6$) δ 4.42 (t, 2H).

Example 150

1-(2-(((Bis(4-fluoro-2-methylphenyl)methylene)amino)oxy)ethyl)-3-piperidinecarboxylic acid hydrochloride Amorph.

HPLC retention time=23.9 minutes (system D).

$^1$H NMR (400 MHz, DMSO-d$_6$) δ 4.50 (m, 2H); 2.40 (s, 3H); 2.15 (s, 3H).

Example 151

(R)-1-(2-((((4-Chloro-2-methylphenyl)-2-methylphenyl)methylene)amino)oxy)ethyl)-3-piperidinecarboxylic acid hydrochloride

M.P. 180° C.

Calculated for $C_{23}H_{28}Cl_2N_2O_3$: C, 61.2%; H, 6.3%; N, 6.2%; Found: C, 61.5%; H, 6.4%; N, 6.1%.

Example 152

1-(2-(((Bis(3-methyl-2-thienyl)methylene)amino)oxy)ethyl)-1,2,5,6-tetrahydro-3-pyridinecarboxylic acid hydrochloride

M.P. 79–80° C.

Example 153

(S)-1-(2-(((Bis(3-methyl-2-thienyl)methylene)amino)oxy)ethyl)-3-piperidinecarboxylic acid hydrochloride

M.P. 168–169° C.

Example 154

(S)-1-(2-((((2-Methylphenyl)-(3-methyl-2-thienyl)methylene)amino)oxy)ethyl)-3-piperidinecarboxylic acid hydrochloride TLC: rf=0.30 (SiO$_2$; dichloromethane/methanol=1:1).

Example 155

1-(2-((((3-Methyl-2-thienyl)-2-thienylmethylene)amino)oxy)ethyl)-1,2,5,6-tetrahydro-3-pyridinecarboxylic acid hydrochloride TLC: rf=0.8 (reversed phase, Whatman KCl 8F, methanol/water=4:1).

Example 156

1-(2-((((2-methylphenyl)phenylmethylene)amino)oxy)ethyl)-1,2,5,6-tetrahydro-3-pyridinecarboxylic acid hydrochloride TLC: rf=0.49 (SiO$_2$; dichloromethane/methanol=1:1).

Example 157

1-(2-((((3-Fluorophenyl)-(2-methylphenyl)methylene)amino)oxy)ethyl)-1,2,5,6-tetrahydro-3-pyridinecarboxylic acid hydrochloride

M.P. 219–223° C.

Example 158

(R)-1-(2-(((Bis(4-fluoro-2-methylphenyl)methylene)amino)oxy)ethyl)-3-piperidinecarboxylic acid ethyl ester hydrochloride

M.P. 102–103° C.

Example 159

(R)-1-(2-(((Bis(4-fluoro-2-methylphenyl)methylene)amino)oxy)ethyl)-3-piperidinecarboxylic acid hydrochloride

M.P. 181–182° C.

Example 160

1-(2-((((2-Methylphenyl)-(3-methyl-2-thienyl)methylene)amino)oxy)ethyl)-1,2,5,6-tetrahydro-3-pyridinecarboxylic acid ethyl ester hydrochloride

M.P. 116–117° C.

Example 161
1-(2-((((2-Methylphenyl)-(3-methyl-2-thienyl)methylene)amino)oxy)ethyl)-1,2,5,6-tetrahydro-3-pyridinecarboxylic acid hydrochloride
M.P. 204–207° C.

Example 162
1-(2-(((Bis(4-Fluoro-2-methylphenyl)methylene)amino)oxy)ethyl)-1,2,5,6-tetrahydro-3-pyridinecarboxylic acid ethyl ester hydrochloride
M.P. 157–159° C.

Example 163
1-(2-(((Bis(4-fluoro-2-methylphenyl)methylene)amino)oxy)ethyl)-1,2,5,6-tetrahydro-3-pyridinecarboxylic acid hydrochloride
M.P. 241–244° C.

Example 164
1-(2-((((2,4-Dichlorophenyl)-(3-Methyl-2-thienyl)methylene)amino)oxy)ethyl)-1,2,5,6-tetrahydro-3-pyridinecarboxylic acid hydrochloride
TLC: rf=0.76 (reversed phase, Whatman KCl 8F, methanol/water=4:1).

Example 165
1-(2-((((2-Chlorophenyl)-(2-methylphenyl)methylene)amino)oxy)ethyl)-1,2,5,6-tetrahydro-3-pyridinecarboxylic acid hydrochloride
M.P. 152–155° C.

Example 166
1-(2-((((2-Methylphenyl)-(3-(trifluoromethyl)phenyl)methylene)amino)oxy)ethyl)-1,2,5,6-tetrahydro-3-pyridinecarboxylic acid hydrochloride
M.P. 205–207° C.

Example 167
(R)-1-(2-((((2-Methylphenyl)-(3-(trifluoromethyl)phenyl)methylene)amino)oxy)ethyl)-3-piperidinecarboxylic acid hydrochloride
M.P. 156–158° C.

Example 168
1-(2-(((2-(4-Fluoro-2-methylphenyl)-(2-methylphenyl)ethylidene)amino)oxy)ethyl)-1,2,5,6-tetrahydro-3-pyridinecarboxylic acid hydrochloride
M.P. 195–200° C.

Example 169
(S)-1-(2-((((2-Methylphenyl)-(3-methyl-2-thienyl)methylene)amino)oxy)ethyl)-3-piperidinecarboxylic acid ethyl ester hydrochloride
TLC: rf=0.35 (SiO$_2$; cyclohexane/ethyl acetate=1:1).

Example 170
1-(2-(((Bis(2-Methylphenyl)methylene)amino)oxy)ethyl)-1,2,5,6-tetrahydro-3-pyridinecarboxylic acid hydrochloride
M.P. 214–218.5° C.

Example 171
(S)-1-(2-(((Bis(2-methylphenyl)methylene)amino)oxy)ethyl)-3-piperidinecarboxylic acid hydrochloride
TLC: rf=0.39 (SiO$_2$; dichloromethane/methanol=1:1).

Example 172
1-(2-(((Diphenylmethylene)amino)oxy)ethyl)-3-piperidinecarboxamide
TLC: rf=0.41 (SiO$_2$; dichloromethane/methanol=9:1).

Example 173
1-(2-(((((4-Chloro-2-methylphenyl)(2-methylphenyl)methylene)amino)oxy)ethyl)-1,2,5,6-tetrahydro-3-pyridinecarboxylic acid hydrochloride
TLC: rf=0.45 (SiO$_2$; dichloromethane/methanol=1:1).

Example 174
1-(2-((((2-Chlorophenyl)phenylmethylene)amino)oxy)ethyl)-1,2,5,6-tetrahydro-3-pyridinecarboxylic acid hydrochloride
M.P. 198.5–200° C.

Example 175
1-(2-(((Phenyl-2-thienylmethylene)amino)oxy)ethyl)-1,2,5,6-tetrahydro-3-pyridinecarboxylic acid hydrochloride
TLC: rf=0.63 (SiO$_2$; dichloromethane/methanol=1:1).

Example 176
1-(2-((((3-Chlorophenyl)(2-methylphenyl)methylene)amino)oxy)ethyl)-1,2,5,6-tetrahydro-3-pyridinecarboxylic acid hydrochloride
M.P. 223° C. (dec).

Example 177
1-(2-((((3-Methoxyphenyl)phenylmethylene)amino)oxy)ethyl)-1,2,5,6-tetrahydro-3-pyridinecarboxylic acid hydrochloride
M.P. 140–145° C.

Example 178
1-(2-((((3-Methoxyphenyl) (2-methylphenyl)methylene)amino)oxy)ethyl)-1,2,5,6-tetrahydro-3-pyridinecarboxylic acid hydrochloride
M.P. 190–195° C.

Example 179
1-(2-((((4-Fluoro-2-methylphenyl) (2-methylphenyl)methylene)amino)oxy)ethyl)-1,2,5,6-tetrahydro-3-pyridinecarboxylic acid hydrochloride
M.p. 205–213° C.

Example 180
1-(2-(((Diphenylmethylene)amino)oxy)ethyl)-1,2,5,6-tetrahydro-3-pyridinecarboxylic acid ethyl ester hydrochloride
M.P. 110–116° C.

Example 181
1-(2-((((2-Fluorophenyl)(2-methylphenyl)methylene)amino)oxy)ethyl)-1,2,5,6-tetrahydro-3-pyridinecarboxylic acid hydrochloride
M.P. 195–196° C. (dec).

Example 182
1-(2-((((2-Chlorophenyl)phenylmethylene)amino)oxy)ethyl)-1,2,5,6-tetrahydro-3-pyridinecarboxylic acid ethyl ester hydrochloride
TLC: rf=0.25 (SiO$_2$; cyclohexane/ethyl acetate=1:1).

Example 183
1-(2-(((Bis(2-methylphenyl)methylene)amino)oxy)ethyl)-1,2,5,6-tetrahydro-3-pyridinecarboxylic acid ethyl ester hydrochloride
M.p. 163–164.5° C.

Example 184
1-(2-((((4-Chloro-2-methylphenyl)-(3-methyl-2-thienyl)methylene)amino)oxy)ethyl)-1,2,5,6-tetrahydro-3-pyridinecarboxylic acid hydrochloride
M.P. 213–216° C.

51

Example 185
1-(2-((((4-Fluoro-2-methylphenyl)-(3-methyl-2-thienyl) methylene)amino)oxy)ethyl)-1,2,5,6-tetrahydro-3-pyridinecarboxylic acid hydrochloride
M.P. 165–169° C.

Example 186
1-(2-((((3,4-Dichlorophenyl)-(2-methylphenyl)methylene) amino)oxy)ethyl)-1,2,5,6-tetrahydro-3-pyridinecarboxylic acid hydrochloride
M.P. 258–260° C.

Example 187
1-(2-(((Bis(2-ethylphenyl)methylene)amino)oxy)ethyl)-1,2, 5,6-tetrahydro-3-pyridinecarboxylic acid hydrochloride
M.P. 130–135° C.

Example 188
1-(3-(((Diphenylmethylene)amino)oxy)-1-propyl)-3-piperidinecarboxylic acid hydrochloride Ethyl nipecotate (15.7 g, 100 mmol) was mixed in dry acetone (120 ml) with 3-bromo-1-propanol (20.9 g, 150 mmol) and dried, powdered potassium carbonate (20.7 g, 150 mmol). The reaction mixture was heated at reflux for 3 h, cooled and filtered. The filtrate was evaporated to an oil (33 g) which was dissolved in dichloromethane. To this solution phosphorous tribromide (30.5 g, 112.5 mmol) was introduced dropwise maintaining reflux during addition, and when this was complete reflux was continued for 2.5 h. After cooling dry methanol (30 ml) was added and the mixture was poured into a mixture of saturated sodium bicarbonate solution (250 ml) and water (250 ml). The dichloromethane layer was separated and the aqueous layer was extracted with ethyl acetate (2×150 ml). The combined organic extracts was dried (MgSO$_4$) and evaporated to an oil which was purified by column chromatography.

Elution with a mixture of cyclohexane and tetrahydrofuran (3:1) provided N-(3-bromo-propyl)nipecotic acid ethyl ester (7.85 g, 28%) as a waxy solid.

Calculated for C$_{11}$H$_{20}$BrNO$_2$,0.2H$_2$O: C, 46.9%; H, 7.2%; N, 4.9%; Found: C, 47.3%; H, 7.9%; N, 4.7%.

This compound was used to alkylate benzophenone oxime, as outlined in

Example 1, and the subsequent ester was hydrolysed to provide the title compound as a gummy solid (0.5 g, 52% from N-(3-bromopropyl)nipecotic acid ethyl ester).

TLC: rf=0.70 (reversed phase, Whatman KC 18F, methanol/water=8:2).

Using (R)-N-(2-bromoethyl)nipecotic acid ethyl ester hydrobromide and an 2,2-diarylacetaldehyde oxime as starting materials the following compounds were prepared (according to the method described in Example 94).

Example 189
(R)-1-(2-(((2,2-Diphenylethylidene)amino)oxy)ethyl)-3-piperidinecarboxylic acid hydrochloride
TLC: rf=0.34 (SiO$_2$; dichloromethane/methanol=1:1).

Example 190
1(R)-1-(2-(((2-(2-Methylphenyl)-2-phenylethylidene) amino)oxy)ethyl)-3-piperidinecarboxylic acid hydrochloride
TLC: rf=0.40 (SiO$_2$; dichloromethane/methanol=1:1).

Example 191
E/Z-(R)-1-(2-(((2-(2-Methylphenyl)-2-(4-fluoro-2-methylphenyl)ethylidene)amino)oxy)ethyl)-3-piperidinecarboxylic acid hydrochloride
M.P. 190–200° C.

52

What is claimed is:

1. A method of treating filariae in the lymphatic system in a subject in need thereof comprising administering to said subject an effective amount of a compound of formula I

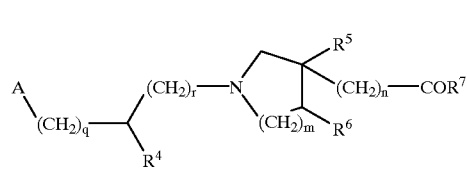

wherein A is

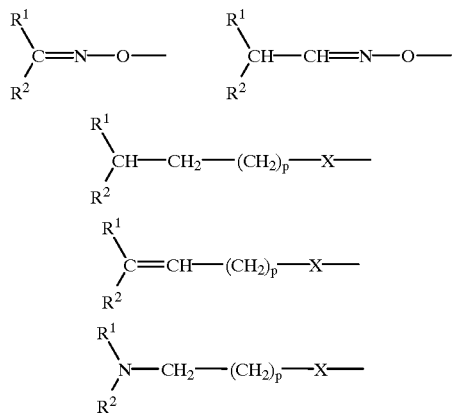

wherein R$^1$ and R$^2$ independently are furanyl, imidazolyl, oxazolyl, phenyl, pyrazolyl, pyrazinyl, pyridazinyl, pyridinyl, pyrimidinyl, pyrrolyl, thiazolyl, thienyl or triazolyl wherein each aromatic ring is optionally substituted with one, two or three substituents selected from —NR$^8$R$^9$, C$_{1-6}$-alkylthio, C$_{1-6}$-alkoxy, azido, cyano, halogen, hydroxy, C$_{1-6}$-alkyl, nitro, mercapto or trifluoromethyl; and X is —CH$_2$—, —O— or —N(R$^3$)— wherein R$^3$ is hydrogen or C$_{1-6}$-alkyl; and R$^4$ is hydrogen or C$_{1-6}$-alkyl; and m is 1 or 2; and n is 1 when m is 1 and n is 0 when m is 2; and R$^5$ and R$^6$ each represents hydrogen or may when m is 2 together represent a bond; and R$^7$ is hydroxy or C$_{1-6}$-alkoxy; and R$^8$ and R$^9$ independently are hydrogen or C$_{1-6}$-alkyl; and p is 0, 1, 2 or 3; and q is 0, 1 or 2; and r is 0, 1 or 2; or a pharmaceutically acceptable salt thereof.

2. The method according to claim 1 wherein the compound is selected from the following:

(R)-N-(2-(2-(Diphenylamino)ethoxy)ethyl)-3-piperidinecarboxylic acid ethyl ester, (R)-N-(2-(2-(Diphenylamino)ethoxy)ethyl)-3-piperidinecarboxylic acid, (R)-N-(6-(Diphenylamino)-1-hexyl)-3-piperidinecarboxylic acid ethyl ester, (R)-N-(6-(Diphenylamino)-1-hexyl)-3-piperidinecarboxylic acid, (R)-N-(3-(Diphenylamino)-1-propyl)-3-piperidinecarboxylic acid, (R)-N-(4-(Diphenylamino)-1-butyl)-3-piperidinecarboxylic acid,
(R)-N-(5-(Diphenylamino)-1-pentyl)-3-piperidinecarboxylic acid,
(R)-N-(7-(Diphenylamino)-1-heptyl)-3-piperidinecarboxylic acid,
(R)-N-(8-(Diphenylamino)-1-octyl)-3-piperidinecarboxylic acid,
(R)-N-(4-(2-(Diphenylamino)ethoxy)-1-butyl)-3-piperidinecarboxylic acid,
(R)-N-(3-(3-Diphenylamino-1-propyloxy)-1-propyl)-3-piperidinecarboxylic acid,
(R)-N-(2-(4-Diphenylamino-1-butyloxy)ethyl)-3-piperidinecarboxylic acid,
(R)-1-(2-((2-((3-Methylphenyl)(phenyl)amino)ethoxy)ethyl)-3-piperidinecarboxylic acid,
(R)-1-(2-(2-((3-Chlorophenyl)(phenyl)amino)ethoxy)ethyl)-3-piperidinecarboxylic acid,
(R)-N-(2-(3,3-Diphenyl-1-propyloxy)ethyl)-3-piperidinecarboxylic acid ethyl ester,
(R)-N-(2-(3,3-Diphenyl-1-propyloxy)ethyl)-3-piperidinecarboxylic acid,
N-(2-(3,3-Diphenyl-1-propyloxy)ethyl)-1,2,5,6-tetrahydro-3-pyridinecarboxylic acid ethyl ester,
N-(2-(3,3-Diphenyl-1-propyloxy)ethyl)-1,2,5,56-tetrahydro-3-pyridinecarboxylic acid,
(R)-1-(2-(3,3-Bis(4-fluorophenyl)-1-propyloxy)ethyl)-3-piperidinecarboxylic acid,
(R)-N-(2-(3-Phenyl-3-(3-(trifluoromethyl)phenyl)-1-propyloxy)ethyl)-3-piperidinecarboxylic acid ethyl ester,
(R)-N-(2-(3-Phenyl-3-(3-(trifluoromethyl)phenyl)-1-propyloxy)ethyl)-3-piperidinecarboxylic acid,
(R)-N-(2-(3,3-Bis(4-Chlorophenyl)-1-propyloxy)ethyl)-3-piperidinecarboxylic acid ethyl ester,
(R)-N-(2-(3,3-Bis(4-Chlorophenyl)-1-propyloxy)ethyl)-3-piperidinecarboxylic acid,
(R)-N-(2-(3,3-Diphenyl-2-propen-1-yloxy)ethyl)-3-piperidinecarboxylic acid ethyl ester,
(R)-N-(2-(3,3-Diphenyl-2-propen-1-yloxy)ethyl)-3-piperidinecarboxylic acid,
(R)-N-(2-(3-(2-Methylphenyl)-3-phenyl-2-propen-1-yloxy)ethyl)-3-piperidinecarboxylic acid,
(R)-N-(2-(3-(2-Methylphenyl)-3-phenyl-1-propyloxy)ethyl)-3-piperidinecarboxylic acid,
(R)-N-(2-(3,3-Bis(4-(Trifluoromethyl)phenyl)-2-propen-1-yloxy)ethyl)-3-piperidinecarboxylic acid,
(R)-N-(2-(3,3-Bis(4-(Trifluoromethyl)phenyl)-1-propyloxy)ethyl)-3-piperidinecarboxylic acid,
(R)-N-(2-(3-(3-Methoxyphenyl)-3-(2-methylphenyl)-2-propen-1-yloxy)ethyl)-3-piperidinecarboxylic acid,
(R)-N-(2-(3-(3-Methoxyphenyl)-3-(2-methylphenyl)-1-propyloxy)ethyl)-3-piperidinecarboxylic acid,
(R)-N-(2-(3,3-Bis(2-Methylphenyl)-2-propen-1-yloxy)ethyl)-3-piperidinecarboxylic acid,
(R)-N-(2-(3,3-Bis(2-Methylphenyl)-1-propyloxy)ethyl)-3-piperidinecarboxylic acid,
(R)-N-(3-(3,3-Bis(2-Methylphenyl)-2-propen-1-yloxy)-1-propyl)-3-piperidinecarboxylic acid,
(R)-N-(3-(3,3-Bis(2-Methylphenyl)-1-propyloxy)-1-propyl)-3-piperidinecarboxylic acid,
(R)-N-(2-(3-(3-Methoxyphenyl)-3-phenyl-2-propen-1-yloxy)ethyl)-3-piperidinecarboxylic acid,
(R)-N-(2-(3-(3-Methoxyphenyl)-3-phenyl-1-propyloxy)ethyl)-3-piperidinecarboxylic acid,
(R)-N-(2-(3,3-Bis(4-Chlorophenyl)-2-propen-1-yloxy)ethyl)-3-piperidinecarboxylic acid ethyl ester,
(R)-N-(2-(3,3-Bis(4-Chlorophenyl)-2-propen-1-yloxy)ethyl)-3-piperidinecarboxylic acid,
(R)-1-(2-((1,1-Bis(4-fluorophenyl)-1-propen-3-yl)oxy)ethyl)-3-piperidinecarboxylic acid,
(R)-N-(2-(3-(3-Chlorophenyl)-3-phenyl-2-propen-1-yloxy)-ethyl)-3-piperidinecarboxylic acid,
(R)-1-(2-(1, 1-Bis(4-fluoro-2-methylphenyl)-1-propen-3-yl)oxy)ethyl)-3-piperidinecarboxylic acid,
(R)-1-(3-((1,1-Diphenyl-1-propen-3-yl)oxy)-1-propyl)-3-piperidinecarboxylic acid,
(R)-1-(2-(1,1-Bis(4-chloro-2-methylphenyl)-1-propen-3-yl)oxy)- ethyl)- 3-piperidinecarboxylic acid, 1-(2-(1,1-Bis(4-fluoro-2-methylphenyl)-1-propen-3-yl)oxy)ethyl)-1,2,5,6-tetrahydropyridine-3-carboxylic acid,
(S)-1-(2-(1,1-Bis(4-fluoro-2-methylphenyl)-1-propen-3-yl)oxy)-ethyl)-3-piperidinecarboxylic acid,
(R)-N-(2-(3-(3-Methylphenyl)-3-phenyl-2-propen-1-yloxy)ethyl)-3-piperidinecarboxylic acid,
(R)-N-(2-(3-(3-Methylphenyl)-3-phenyl-1-propyloxy)ethyl)-3-piperidinecarboxylic acid,
(R)-1-(2-(3,3-Bis(4-fluoro-2-methylphenyl)-1-propyloxy)ethyl-3-piperidinecarboxylic acid,
(R)-1-(2-((2,2-Diphenylethenyl)oxy)ethyl)-3-piperidinecarboxylic acid ethyl ester,
(R)-1-(2-((2,2-Diphenylethenyl)oxy)ethyl)-3-piperidinecarboxylic acid,
Z-(R)-1-(2-((2-(2-Methylphenyl)-2-phenylethenyl)oxy)ethyl)-3-piperidinecarboxylic acid,
E-(R)-1-(2-((2-(2-Methylphenyl)-2-phenylethenyl)oxy)ethyl)-3-piperidinecarboxylic acid,
E-(R)-1-(2-((2-(2-Chlorophenyl)-2-phenylethenyl)oxy)ethyl)-3-piperidinecarboxylic acid,
Z-(R)-1-(2-((2-(2-Chlorophenyl)-2-phenylethenyl)oxy)ethyl)-3-piperidinecarboxylic acid,
E-(R)-1-(2-((2-(2-Chlorophenyl)-2-phenylethenyl)oxy)ethyl)-3-piperidinecarboxylic acid,
Z-(R)-1-(2-((2-(2-Chlorophenyl)-2-phenylethenyl)oxy)ethyl)-3-piperidinecarboxylic acid,
(R)-1-(3-((2,2-Diphenylethenyl)oxy)-1-propyl)-3-piperidinecarboxylic acid,
(R)-1-(2-((2-(2-Methylphenyl)-2-(3-methyl-2-thienyl)ethenyl)oxy)ethyl)-3-piperidinecarboxylic acid,
E-(R)-1-(2-((2-(3-Fluorophenyl)-2-(2-methylphenyl)-ethenyl)-oxy)ethyl)-3 -piperidinecarboxylic acid,
Z-(R)-1-(2-((2-(3-Fluorophenyl)-2-(2-methylphenyl)ethenyl)-oxy)ethyl)-3-piperidinecarboxylic acid,
E-(R)-1-(2-((2-(3-Fluorophenyl)-2-(2-methylphenyl)ethenyl)oxy)ethyl)-3-piperidinecarboxylic acid,
Z-(R)-1-(2-((2-(3-Fluorophenyl)-2-(2-methylphenyl)ethenyl)oxy)ethyl)-3-piperidinecarboxylic acid,
(R)-1-(2-((2,2-Bis(4-fluorophenyl)ethenyl)oxy)ethyl)-3-piperidinecarboxylic acid,
(R)-1-(2-((2,2-Bis(2-chloro-4-fluorophenyl)ethenyl)oxy)ethyl)-3-piperidinecarboxylic acid,
(R)-1-(2-((2,2-Bis(2,4-difluorophenyl)ethenyl)oxy)ethyl)-3-piperidinecarboxylic acid,
(R)-1-(2-(((2,4-Difluorophenyl)-2-(2,5-difluorophenyl)ethenyl)oxy)ethyl)-3-piperidinecarboxylic acid, (R)-1-(2-((2,2-Bis(2,5-difluorophenyl)ethenyl)oxy) ethyl)-3-piperidinecarboxylic acid,
(R)-1-(2-((2,2-bis(3-Methyl-2-thienyl)ethenyl)oxy) ethyl)-3-piperidinecarboxylic acid ethyl ester,
(R)-1-(2-((2,2-bis(3-Methyl-2-thienyl)ethenyl)oxy)ethyl) 3-piperidinecarboxylic acid,
1-(2-((2,2-bis(2-Methylphenyl)ethenyl)oxy)ethyl)-1,2,5, 6-tetrahydro-3-pyridinecarboxylic acid,
(R)-1-(2-((2-(4-Fluoro-2-methylphenyl)-2-(2-methylphenyl)ethenyl)oxy)ethyl)-3-piperidinecarboxylic acid,
1-(2-((2-(4-Fluoro-2-methylphenyl)-2-(2-methylphenyl) ethenyl)oxy)ethyl)-1,2,5,6-tetrahydro-3-pyridinecarboxylic acid,
1-(2-((2,2-bis(3-Fluorophenyl)ethenyl)oxy)ethyl)-1,2,5, 6-tetrahydro-3-pyridinecarboxylic acid,
(R)-1-(2-((2,2-bis(2-Methylphenyl)ethenyl)oxy)ethyl)-3-piperidinecarboxylic acid,
(R)-1-(2-((2,2-bis(4-Fluoro-2-methylphenyl)ethenyl) oxy)ethyl)-3-piperidinecarboxylic acid,
E-(R)-1-(2-((2-(3-Methoxyphenyl)-2-(2-methylphenyl) ethenyl)oxy)ethyl)-3-piperidinecarboxylic acid,
Z-(R)-1-(2-((2-(3-Methoxyphenyl)-2-(2-methylphenyl) ethenyl)oxy)ethyl)-3-piperidinecarboxylic acid,
1-(2-((2-(3-Methoxyphenyl)-2-(2-methylphenyl)ethenyl) oxy)ethyl)-1,2,5,6-tetrahydro-3-pyridine carboxylic acid,
1-(2-((2-(3-Chlorophenyl)-2-(2-methylphenyl)ethenyl) oxy)ethyl)-1,2,5,6-tetrahydro-3-pyridinecarboxylic acid,
1-(2-((2,2-bis(2-Ethylphenyl)ethenyl)oxy)ethyl)-1,2,5,6-tetrahydro-3-pyridinecarboxylic acid,
(R)-1-(2-((2,2-bis(2-Ethylphenyl)ethenyl)oxy)ethyl)-3-piperidinecarboxylic acid,
1-(2-((2,2-Diphenylethenyl)oxy)ethyl)-1,2,5,6-tetrahydro-3-pyridinecarboxylic acid,
1-(2-((2-(2-Fluorophenyl)-2-(2-methylphenyl)ethenyl) oxy)-ethyl)-1,2,5,6-tetrahydro-3-pyridinecarboxylic acid,
1-(2-((2-(2,4-Dichlorophenyl)-2-(2-methylphenyl) ethenyl)-oxy)ethyl)-1,2,5,6-tetra-hydro-3-pyridinecarboxylic acid,
1-(2-((2,2-bis(2-Chlorophenyl)ethenyl)oxy)ethyl)-1,2,5, 6-tetrahydro-3-pyridinecarboxylic acid,
1-(2-((2,2-bis(4-Fluoro-2-methylphenyl)ethenyl)oxy) ethyl)-1,2,5,6-tetrahydro-3-pyridinecarboxylic acid,
(R)-1-(2-((2-(2-Chlorophenyl)-2-(2-methylphenyl) ethenyl)oxy)ethyl)-3-piperidinecarboxylic acid, 1-(2-(((2-(2-Chlorophenyl)-2-(2-methylphenyl)ethenyl) oxy)ethyl)-1,2,5,6-tetra-hydro-3-pyridinecarboxylic acid,
(R)-1-(3-((2,2-bis(4-Fluorophenyl)ethenyl)oxy)-1-propyl)-3-piperidinecarboxylic acid,
(R)-1-(2-((2,2-Bis-(2-chlorophenyl)ethenyl)oxy)ethyl)-3-piperidinecarboxylic acid,
(R)-1-(2-((2,2-Diphenylethyl)oxy)ethyl)-3-piperidinecarboxylic acid,
(R)-1-(2-(2,2-Bis(2,4-difluorophenyl)ethoxy)ethyl)-3-piperidinecarboxylic acid,
(R)-1-(2-(Bis(4-fluoro-2-methylphenyl)ethoxy)ethyl)-3-piperidinecarboxylic acid,
(R)-1-(2-(2,2-Bis(2,5-difluorophenyl)ethoxy)ethyl)-3-piperidinecarboxylic acid,
(R)-1-(2-((2, 2-Bis(3-chlorophenyl)ethenyl)oxy)ethyl)-3-piperidinecarboxylic acid,
(R)-1-(3-(2,2-Diphenylethoxy)-1-propyl)-3-piperidinecarboxylic acid,
(R)-1-(2-(((Diphenylmethylene)amino)oxy)ethyl)-3-piperidinecarboxylic,
(R)-1-(2-(((Bis(2-chloro-4-fluorophenyl)methylene) amino)oxy)ethyl)-3-piperidinecarboxylic acid,
(R)-1-(2-(((Bis(2,4-diflourophenyl)methylene)amino) oxy)ethyl)-3-piperidinecarboxylic acid,
(R)-1-(2-((((2,4-Difluorophenyl)-(2,5-difluorophenyl) methylene)amino)oxy)ethyl)-3-piperidinecarboxylic acid,
(R)-1-(2-(((Bis(3,5-difluorophenyl)methylene)amino) oxy)ethyl)-3-piperidinecarboxylic acid,
(R)-1-(2-((((2-Fluorophenyl)-(2-methylphenyl) methylene)amino)oxy)ethyl)-3-piperidinecarboxylic acid,
(R)-1-(2-(((Bis(2,5-difluorophenyl)methylene)amino) oxy)ethyl)-3-piperidinecarboxylic acid,
E-(R)-1-(2-((((2-Methylphenyl)-(3-methyl-2-thienyl-methylene)amino)oxy)ethyl)-3-piperidinecarboxylic acid,
Z-(R)-1-(2-((((2-Methylphenyl)-(3-methyl-2-thienyl-methylene)amino)oxy)ethyl)-3-piperidinecarboxylic acid,
(R)-1-(2-(((Bis(3-methyl-2-thienyl)methylene)amino) oxy)ethyl)-3-piperidinecarboxylic acid,
(R)-1-(2-((((2-Ethylphenyl)-(3-methyl-2-thienyl) methylene)amino)oxy)ethyl)- 3-piperidinecarboxylic acid,
(R)-1-(2-((((3-Methyl-2-thienyl)-2-thienylmethylene) amino)oxy)ethyl)-3-piperidinecarboxylic acid,
(R)-1-(2-((((3-Methoxyphenyl)-(3-methyl-2-thienyl) methylene)amino)oxy)ethyl)-3-piperidinecarboxylic acid,
(R)-1-(2-((((2-Methylphenyl)-(1-methyl-1H-pyrrol-2-yl) methylene)amino)oxy)ethyl)-3-piperidinecarboxylic acid,
(R)-1-(2-((((1-Methyl-1H-pyrrol-2-yl)phenylmethylene) amino)-oxy)ethyl)-3-piperidinecarboxylic acid,
E-(R)-1-(2-((((3-Methoxyphenyl)-(4-methyl-2-thienyl) methylene)amino)oxy)ethyl)-3-piperidinecarboxylic acid,
Z-(R)-1-(2-((((3-Methoxyphenyl)-(4-methyl-2-thienyl) methylene)amino)oxy)ethyl)-3-piperidinecarboxylic acid,
E-(R)-1-(2-((((2-Methylphenyl)-(3-methyl-2-thienyl) methylene)amino)oxy)ethyl)-3-piperidinecarboxylic acid,
Z-(R)-1-(2-((((2-Methylphenyl)-(3-methyl-2-thienyl) methylene)amino)oxy)ethyl)-3-piperidinecarboxylic acid,
E-(R)-1-(2-((((2-Methyl-2H-1,2,4-triazol-3-yl)-2-thienyl-methylene)amino)oxy)ethyl-3-piperidinecarboxylic acid,
Z-(R)-1-(2-((((2-Methyl-2H-1,2,4-triazol-3-yl)-2-thienyl-methylene)amino)oxy)ethyl)-3-piperidinecarboxylic acid,
E-(R)-1-(2-((((2-Methyl-2H-1,2,4-triazol-3-yl)-2-thienyl-methylene)amino)oxy)ethyl)-3-piperidinecarboxylic acid,
Z-(R)-1-(2-((((2-Methyl-2H-1,2,4-triazol-3-yl)-2-thienyl-methylene)amino)oxy)ethyl)-3-piperidinecarboxylic acid, (R)-1-(2-((((3-Azidophenyl)(3-methyl-2-thienyl)methylene)amino)oxy)ethyl)-3-piperidinecarboxylic acid, E-(R)-1-(2-((((2-Methylphenyl)-(3-methyl-2-thienyl)methylene)amino)oxy)ethyl)-3-piperidinecarboxylic acid ethyl ester, Z-(R)-1-(2-((((2-Methylphenyl)-(3-methyl-2-thienyl)methylene)amino)oxy)ethyl)-3-piperidinecarboxylic acid ethyl ester, (R)-1-(2-((((2-Azidophenyl)phenylmethylene)amino)oxy)ethyl)-3-piperidinecarboxylic acid, (S)-1-(2-(((Diphenylmethylene)amino)oxy)ethyl)-3-piperidinecarboxylic acid, (R)-1-(2-(((Bis(3-ethyl-2-thienyl)methylene)amino)oxy)ethyl)-3-piperidinecarboxylic acid, (R)-1-(2-((((2,4-Dichlorophenyl)(3-methyl-2-thienyl)methylene)amino)oxy)ethyl)-3-piperidinecarboxylic acid, (R)-1-(2-((((3-Methoxyphenyl)phenylmethylene)amino)oxy)ethyl)-3-piperidinecarboxylic acid, (R)-1-(2-((((2-Methylphenyl)(3-methoxyphenyl)methylene)amino)oxy)ethyl)-3-piperidinecarboxylic acid, (R)-1-(2-(((Bis(4-chloro-2-methylphenyl)methylene)amino)oxy)ethyl)-3-piperidinecarboxylic acid, E-(R)-1-(2-((((2-Methylphenyl)-(3-methyl-2-thienyl)methylene)amino)oxy)ethyl)-3-piperidinecarboxylic acid ethyl ester, Z-(R)-1-(2-((((2-Methylphenyl)-(3-methyl-2-thienyl)methylene)amino)oxy)ethyl)-3-piperidinecarboxylic acid ethyl ester, (R)-1-(2-((((4-Chloro-2-methylphenyl)-(3-methyl-2-thienyl)methylene)amino)oxy)ethyl)-3-piperidinecarboxylic acid, (R)-1-(2-(((Bis(2-methylphenyl)methylene)amino)oxy)ethyl)-3-piperidinecarboxylic acid, 1-(2-(((Diphenylmethylene)amino)oxy)ethyl)-3-piperidinecarboxylic acid, E-1-(2-((((2-Methylphenyl)-(3-methyl-2-thienyl)methylene)-amino)oxy)ethyl)-3-piperidinecarboxylic acid, Z-1-(2-((((2-Methylphenyl)-(3-methyl-2-thienyl)methylene)-amino)oxy)ethyl)-3-piperidinecarboxylic acid, 1-(2-((((1-Methyl-1H-imidazol-2-yl)phenylmethylene)amino)oxy)ethyl)3-piperidinecarboxylic acid, 1-(2-(((Phenyl-2-pyridinylmethylene)amino)oxy)ethyl)-3-piperidinecarboxylic acid, 1-(2-(((Phenyl-1H-pyrrol-2-ylmethylene)amino)oxy)ethyl)-3-piperidinecarboxylic acid, 1-(2-(((Bis(4-chlorophenyl)methylene)amino)oxy)ethyl)-3-piperidinecarboxylic acid, 1-(2-((((4-Azidophenyl)phenylmethylene)amino)oxy)ethyl)-3-piperidinecarboxylic acid, 1-(2-((((4-Fluorophenyl)phenylmethylene)amino)oxy)ethyl)-3-piperidinecarboxylic acid, 1-(2-((((2-Chlorophenyl)phenylmethylene)amino)oxy)ethyl)-3-piperidinecarboxylic acid, 1-(2-((((4-Chloro-2-methylphenyl)-(2-methylphenyl)methylene)amino)oxy)ethyl)-3-piperidinecarboxylic acid, 1-(2-((((3-Azidophenyl)phenylmethylene)amino)oxy)ethyl)-3-piperidinecarboxylic acid, 1-(2-((((3-Nitrophenyl)phenylmethylene)amino)oxy)ethyl)-3-piperidinecarboxylic acid, 1-(2-(((Bis(2-hydroxyphenyl)methylene)amino)oxy)ethyl)-3-piperidinecarbocylic acid, 1-(2-(((Bis(3-methoxyphenyl)methylene)amino)oxy)ethyl)-3-piperidinecarboxylic acid, 1-(2-((((2,4-Dichlorophenyl)-(3-methyl-2-thienyl)methylene)amino)oxy)ethyl)-3-piperidinecarboxylic acid, (R)-1-(2-((((2-Chlorophenyl)-(2-methylphenyl)methylene)amino)oxy)ethyl)-3-piperidinecarboxylic acid, 1-(2-((((2-Methylphenyl)(3-methylphenyl)methylene)amino)oxy)ethyl)-3-piperidinecarboxylic acid, 1-(2-((((4-Methyl-2-thienyl)-(2-tolyl)methylene)amino)oxy)ethyl)-3-piperidinecarboxylic acid, 1-(2-((((3-Hydroxyphenyl)phenylmethylene)amino)oxy)ethyl)-3-piperidinecarboxylic acid, 1-(2-(((Bis(2-tolyl)methylene)amino)oxy)-1-propyl)-3-piperidinecarboxylic acid, 1-(2-(((Diphenylmethylene)amino)oxy)ethyl)-1,2,5,6-tetrahydro-3-pyridinecarboxylic acid, (R)-1-(2-((((2,4-Dichlorophenyl)-(3-methoxyphenyl)methylene)amino)oxy)ethyl)-3-piperidinecarboxylic acid, (R)-1-(2-(((Bis(3-chlorophenyl)methylene)amino)oxy)ethyl)-3-piperidinecarboxylic acid, E-(R)-1-(2-((((2-Chloro-4-fluorophenyl)-(3-fluorophenyl)methylene)amino)oxy)ethyl)-3-piperidinecarboxylic acid, Z-(R)-1-(2-((((2-Chloro-4-fluorophenyl)-(3-fluorophenyl)methylene)amino)oxy)ethyl)-3-piperidinecarboxylic acid, E-(R)-1-(2-((((2-Fluorophenyl)-(4-fluorophenyl)methylene)-amino)oxy)ethyl)-3-piperidinecarboxylic acid, Z-(R)-1-(2-((((2-Fluorophenyl)-(4-fluorophenyl)methylene)-amino)oxy)ethyl)-3-piperidinecarboxylic acid, (R)-1-(2-(((Bis(4-fluoro-2-methylphenyl)methylene)amino)oxy)ethyl)-3-pyrrolidine-acetic acid, 1-(2-(((Bis(4-fluoro-2-methylphenyl)methylene)amino)oxy)ethyl)-3-piperidinecarboxylic acid, (R)-1-(2-((((4-Chloro-2-methylphenyl)-2-methylphenyl)methylene)amino)oxy)ethyl)-3-piperidinecarboxylic acid, 1-(2-(((Bis(3-methyl-2-thienyl)methylene)amino)oxy)ethyl)-1,2,5,6-tetrahydro-3-pyridinecarboxylic acid, (S)-1-(2-(((Bis(3-methyl-2-thienyl)methylene)amino)oxy)ethyl)-3-piperidinecarboxylic acid, (S)-1-(2-((((2-Methylphenyl)-(3-methyl-2-thienyl)methylene)amino)oxy)ethyl)-3-piperidinecarboxylic acid, 1-(2-((((3-Methyl-2-thienyl)-2-thienylmethylene)amino)oxy)ethyl)-1,2,5,6-tetrahydro-3-pyridinecarboxylic acid, 1-(2-((((2-methylphenyl)phenylmethylene)amino)oxy)ethyl)-1,2,5,6-tetrahydro-3-pyridinecarboxylic acid, 1-(2-((((3-Fluorophenyl)-(2-methylphenyl)methylene)amino)oxy)ethyl)-1,2,5,6-tetrahydro-3-pyridinecarboxylic acid, (R)-1-(2-(((Bis(4-fluoro-2-methylphenyl)methylene)amino)oxy)ethyl)-3-piperidinecarboxylic acid ethyl ester, (R)-1-(2-(((Bis(4-fluoro-2-methylphenyl)methylene)amino)oxy)ethyl)-3-piperidinecarboxylic acid,
1-(2-((((2-Methylphenyl)-(3-methyl-2-thienyl)methylene)amino)oxy)ethyl)-1,2,5,6-tetrahydro-3-pyridinecarboxylic acid ethyl ester,
1-(2-((((2-Methylphenyl)-(3-methyl-2-thienyl)methylene)amino)oxy)ethyl)-1,2,5,6-tetrahydro-3-pyridinecarboxylic acid,
1-(2-(((Bis(4-Fluoro-2-methylphenyl)methylene)amino)oxy)ethyl)-1,2,5,6-tetrahydro-3-pyridinecarboxylic acid ethyl ester,
1-(2-(((Bis(4-fluoro-2-methylphenyl)methylene)amino)oxy)ethyl)-1,2,5,6-tetrahydro-3-pyridinecarboxylic acid,
1-(2-((((2,4,-Dichlorophenyl)-(3-Methyl-2-thienyl)methylene)amino)oxy)ethyl)-1,2,5,6-tetrahydro-3-pyridinecarboxylic acid,
1-(2-((((2-Chlorophenyl)-(2-methylphenyl)methylene)amino)oxy)ethyl)-1,2,5,6-tetrahydro-3-pyridinecarboxylic acid,
1-(2-((((2-Methylphenyl)-(3-(trifluoromethyl)phenyl)methylene)amino)oxy)ethyl)-1,2,5,6-tetrahydro-3-pyridinecarboxylic acid,
(R)-1-(2-((((2-Methylphenyl)-(3-(trifluoromethyl)phenyl)methylene)amino)oxy)-ethyl)-3-piperidinecarboxylic acid,
1-(2-(((2-(4-Fluoro-2-methylphenyl)-(2-methylphenyl)ethylidene)amino)oxy)ethyl)-1,2,5,6-tetrahydro-3-pyridinecarboxylic acid,
(S)-1-(2-((((2-Methylphenyl)-(3-methyl-2-thienyl)methylene)amino)oxy)ethyl)-3-piperidinecarboxylic acid ethyl ester,
1-(2-(((Bis(2-Methylphenyl)methylene)amino)oxy)ethyl)-1,2,5,6-tetrahydro-3-pyridinecarboxylic acid,
(S)-1-(2-(((Bis(2-methylphenyl)methylene)amino)oxy)ethyl)-3-piperidinecarboxylic acid,
1-(2-(((Diphenylmethylene)amino)oxy)ethyl)-3-piperidinecarboxamide,
1-(2-((((4-Chloro-2-methylphenyl) (2-methylphenyl)methylene)amino)oxy)ethyl)-1,2,5,6-tetrahydro-3-pyridinecarboxylic acid,
1-(2-((((2-Chlorophenyl)phenylmethylene)amino)oxy)ethyl)-1,2,5,6-tetrahydro-3-pyridinecarboxylic acid,
1-(2-(((Phenyl-2-thienylmethylene)amino)oxy)ethyl)-1,2,5,6-tetrahydro-3-pyridinecarboxylic acid,
1-(2-((((3-Chlorophenyl)(2-methylphenyl)methylene)amino)oxy)ethyl)-1,2,5,6-tetrahydro-3-pyridinecarboxylic acid,
1-(2-((((3-Methoxyphenyl)phenylmethylene)amino)oxy)ethyl)-1,2,5,6-tetrahydro-3-pyridinecarboxylic acid,
1-(2-((((3-Methoxyphenyl) (2-methylphenyl)methylene)amino)oxy)ethyl)-1,2,5,6-tetrahydro-3-pyridinecarboxylic acid,
1-(2-((((4-Fluoro-2-methylphenyl)(2-methylphenyl)methylene)amino)oxy)ethyl)-1,2,5,6-tetrahydro-3-pyridinecarboxylic acid,
1-(2-(((Diphenylmethylene)amino)oxy)ethyl)-1,2,5,6-tetrahydro-3-pyridinecarboxylic acid ethyl ester,
1-(2-((((2-Fluorophenyl)(2-methylphenyl)methylene)amino)oxy)ethyl)-1,2,5,6-tetrahydro-3-pyridinecarboxylic acid,
1-(2-((((2-Chlorophenyl)phenylmethylene)amino)oxy)ethyl)-1,2,5,6-tetrahydro-3-pyridinecarboxylic acid ethyl ester,
1-(2-(((Bis(2-methylphenyl)methylene)amino)oxy)ethyl)-1,2,5,6-tetrahydro-3-pyridinecarboxylic acid ethyl ester,
1-(2-((((4-Chloro-2-methylphenyl)-(3-methyl-2-thienyl)methylene)amino)oxy)ethyl)-1,2,5,6-tetrahydro-3-pyridinecarboxylic acid,
1-(2-((((4-Fluoro-2-methylphenyl)-(3-methyl-2-thienyl)methylene)amino)oxy)ethyl)-1,2,5,6-tetrahydro-3-pyridinecarboxylic acid,
1-(2-((((3,4-Dichlorophenyl)-(2-methylphenyl)methylene)amino)oxy)ethyl)-1,2,5,6-tetrahydro-3-pyridinecarboxylic acid,
1-(2-(((Bis(2-ethylphenyl)methylene)amino)oxy)ethyl)-1,2,5,6-tetrahydro- 3-pyridinecarboxylic acid,
1-(3-(((Diphenylmethylene)amino)oxy)-1-propyl)-3-piperidinecarboxylic acid,
(R)-1-(2-(((2,2-Diphenylethylidene)amino)oxy)ethyl)-3-piperidinecarboxylic acid,
(R)-1-(2-(((2-(2-Methylphenyl)-2-phenylethylidene)amino)oxy)ethyl)-3-piperidinecarboxylic acid,
E/Z-(R)-1-(2-(((2-(2-Methylphenyl)-2-(4-fluoro-2-methylphenyl)ethylidene)amino)-oxy)ethyl)-3-piperidinecarboxylic acid, or a pharmaceutically acceptable salt thereof.

3. The method according to claim 1 wherein A is $$\begin{matrix} R^1 \\ \phantom{R}\diagdown \\ \phantom{RR}C=N-O- \\ \phantom{R}\diagup \\ R^2 \end{matrix};$$

wherein $R^1$ and $R^2$ independently are thienyl or phenyl optionally substituted with one, two or three substituents selected from the group consisting of $-NR^8R^9$, $C_{1-6}$-alkylthio, $C_{1-6}$-alkoxy, azido, cyano, halogen, hydroxy, $C_{1-6}$-alkyl, nitro, mercapto and trifluoromethyl.

4. The method according to claim 1 wherein A is $$\begin{matrix} R^1 \\ \phantom{R}\diagdown \\ \phantom{RR}C=N-O- \\ \phantom{R}\diagup \\ R^2 \end{matrix};$$

wherein $R^1$ and $R^2$ independently are thienyl or phenyl optionally substituted with one, two or three substituents selected from the group consisting of $-NR^8R^9$, $C_{1-6}$-alkylthio, $C_{1-6}$-alkoxy, azido, cyano, halogen, hydroxy, $C_{1-6}$-alkyl, nitro, mercapto and trifluoromethyl.

5. The method according to claim 1 wherein A is $$\begin{matrix} R^1 \\ \phantom{R}\diagdown \\ \phantom{RR}CH-CH_2-(CH_2)_p-X- \\ \phantom{R}\diagup \\ R^2 \end{matrix}$$

wherein $R^1$ and $R^2$ independently are thienyl or phenyl optionally substituted with one, two or three substituents selected from $-NR^8R^9$, $C_{1-6}$-alkylthio, $C_{1-6}$-alkoxy, azido, cyano, halogen, hydroxy, $C_{1-6}$-alkyl, nitro, mercapto or trifluoromethyl; and X is $-CH_2$-, $-O-$ or $-N(R^3)-$ wherein $R^3$ is hydrogen or $C_{1-6}$-alkyl.

6. The method according to claim 1 wherein A is

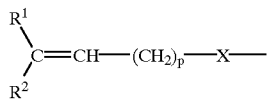

wherein $R^1$ and $R^2$ independently are thienyl or phenyl optionally substituted with one, two or three substituents selected from —$NR^8R^9$, $C_{1-6}$-alkylthio, $C_{1-6}$-alkoxy, azido, cyano, halogen, hydroxy, $C_{1-6}$-alkyl, nitro, mercapto or trifluoromethyl; and X is —$CH_2$—, —O— or —$N(R^3)$— wherein $R^3$ is hydrogen or $C_{1-6}$-alkyl.

7. The method according to claim 1 wherein A is

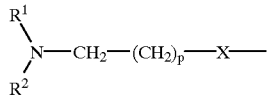

wherein $R^1$ and $R^2$ independently are thienyl or phenyl optionally substituted with one, two or three substituents selected from —$NR^8R^9$, $C_{1-6}$-alkylthio, $C_{1-6}$-alkoxy, azido, cyano, halogen, hydroxy, $C_{1-6}$-alkyl, nitro, mercapto or trifluoromethyl; and X is —$CH_2$—, —O— or —$N(R^3)$— wherein $R^3$ is hydrogen or $C_{1-6}$-alkyl.

8. The method according to claim 3 wherein m is 2 and n is 0.

9. The method according to claim 4 wherein m is 2 and n is 0.

10. The method according to claim 5 wherein m is 2 and n is 0.

11. The method according to claim 6 wherein m is 2 and n is 0.

12. The method according to claim 7 wherein m is 2 and n is 0.

13. The method according to claim 2 wherein the compound is:
(R)-N-(6-(Diphenylamino)-1-hexyl)-3-piperidinecarboxlic acid,
(R)-N-(3-(Diphenylamino)-1-propyl)-3-piperidinecarboxylic acid,
(R)-N-(4-(Diphenylamino)-1-butyl)-3-piperidinecarboxylic acid,
(R)-N-(5-(Diphenylamino)-1-pentyl)-3-piperidinecarboxylic acid,
(R)-N-(7-(Diphenylamino)-1-heptyl)-3-piperidinecarboxylic acid,
(R)-N-(8-(Diphenylamino)-1-octyl)-3-piperidinecarboxylic acid, or
(R)-N-(6-(Diphenylamino)-1-hexyl)-3-piperidinecarboxylic acid ethyl ester;
or a pharmaceutically acceptable salt thereof.

14. The method according to claim 2 wherein the compound is:
(R)-N-(2-(3-(2-Methylphenyl)-3-phenyl-2-propen-1-yloxy)ethyl)-3-piperidinecarboxylic acid,
(R)-N-(2-(3,3-Diphenyl-2-propen-1-yloxy)ethyl)-3-piperidinecarboxylic acid,
(R)-N-(2-(3,3-Bis(4-(Trifluoromethyl)phenyl)-2-propen-1-yloxy)ethyl)-3-piperidinecarboxylic acid,
(R)-N-(2-(3-(3-Methoxyphenyl)-3-(2-methylphenyl)-2-propen-1-yloxy)ethyl)-3-piperidinecarboxylic acid,
(R)-N-(2-(3,3-Bis(2-Methylphenyl)-2-propen-1-yloxy)ethyl)-3-piperidinecarboxylic acid,
(R)-N-(3-(3,3-Bis(2-Methylphenyl)-2-propen-1-yloxy)-1-propyl)-3-piperidinecarboxylic acid,
(R)-N-(2-(3-(3-Methoxyphenyl)-3-phenyl-2-propen-1-yloxy)ethyl)-3-piperidinecarboxylic acid,
(R)-N-(2-(3,3-Bis(4-Chlorophenyl)-2-propen-1-yloxy)ethyl)-3-piperidinecarboxylic acid,
(R)-1-(2-((1,1-Bis(4-fluorophenyl)-1-propen-3-yl)oxy)ethyl)-3-piperidinecarboxylic acid,
(R)-N-(2-(3-(3-Chlorophenyl)-3-phenyl-2-propen-1-yloxy)-ethyl)-3-piperidinecarboxylic acid,
(R)-N-(2-(3-(3-Methylphenyl)-3-phenyl-2-propen-1-yloxy)ethyl)-3-piperidinecarboxylic acid
(S)-1-(2-(1,1-Bis(4-fluoro-2-methylphenyl)-1-propen-3-yl)oxy)-ethyl)-3-piperidinecarboxylic acid,
(R)-1-(2-(1,1-Bis(4-fluoro-2-methylphenyl)-1-propen-3-yl)oxy)ethyl)-3-piperidinecarboxylic acid,
(R)-1-(3-((1,1-Diphenyl-1-propen-3-yl)oxy)-1-propyl)-3-piperidinecarboxylic acid,
(R)-1-(2-(1,1-Bis(4-chloro-2-methylphenyl)-1-propen-3-yl)oxy)ethyl)-3-piperidinecarboxylic acid,
1-(2-(1,1-Bis(4-fluoro-2-methylphenyl)-1-propen-3-yl)oxy)ethyl)-1,2,5,6-tetrahydropyridine-3-carboxylic acid,
(R)-N-(2-(3,3-Bis(4-Chlorophenyl)-2-propen-1-yloxy)ethyl)-3-piperidinecarboxylic acid ethyl ester, or
(R)-N-(2-(3,3-Diphenyl-2-propen-1-yloxy)ethyl)-3-piperidinecarboxylic acid ethyl ester;
or a pharmaceutically acceptable salt thereof.

15. The method according to claim 2 wherein the compound is:
(R)-N-(2-(3-(2-Methylphenyl)-3-phenyl-1-propyloxy)ethyl)-3-piperidinecarboxylic acid,
(R)-N-(2-(3,3-Diphenyl-1-propyloxy)ethyl)-3-piperidinecarboxylic acid,
(R)-1-(2-(3,3-Bis(4-fluorophenyl)-1-propyloxy)ethyl)-3-piperidinecarboxylic acid,
(R)-N-(2-(3-Phenyl-3-(3-(trifluoromethyl)phenyl)-1-propyloxy)ethyl)-3-piperidinecarboxylic acid,
(R)-N-(2-(3,3-Bis(4-Chlorophenyl)-1-propyloxy)ethyl)-3-piperidinecarboxylic acid,
(R)-N-(3-(3,3-Bis(2-Methylphenyl)-1-propyloxy)-1-propyl)-3-piperidinecarboxylic acid,
(R)-N-(2-(3-(3-Methoxyphenyl)-3-phenyl-1-propyloxy)ethyl)-3-piperidinecarboxylic acid,
(R)-N-(2-(3,3-Bis(4-(Trifluoromethyl)phenyl)-1-propyloxy)ethyl)-3-piperidinecarboxylic acid,
(R)-N-(2-(3-(3-Methoxyphenyl)-3-(2-methylphenyl)-1-propyloxy)ethyl)-3-piperidinecarboxylic acid,
(R)-N-(2-(3,3-Bis(2-Methylphenyl)-1-propyloxy)ethyl)-3-piperidinecarboxylic acid,
(R)-N-(2-(3-(3-Methylphenyl)-3-phenyl-1-propyloxy)ethyl)-3-piperidinecarboxylic acid,
(R)-N-(2-(3,3-Diphenyl-1-propyloxy)ethyl)-3-piperidinecarboxylic acid ethyl ester,
(R)-N-(2-(3-Phenyl-3-(3-(trifluoromethyl)phenyl)-1-propyloxy)ethyl)-3-piperidinecarboxylic acid ethyl ester,
(R)-N-(2-(3,3-Bis(4-Chlorophenyl)-1-propyloxy)ethyl)-3-piperidinecarboxylic acid ethyl ester,
(R)-1-(2-((2,2-Diphenylethyl)oxy)ethyl)-3-piperidinecarboxylic acid, (R)-1-(2-(2,2-Bis(2,4-difluorophenyl)ethoxy)ethyl)-3-piperidinecarboxylic acid,
(R)-1-(2-(Bis(4-fluoro-2-methylphenyl)ethoxy)ethyl)-3-piperidinecarboxylic acid,
(R)-1-(3-(2,2-Diphenylethoxy)-1-propyl)-3-piperidinecarboxylic acid,
(R)-1-(2-(3,3-Bis(4-fluoro-2-methylphenyl)-1-propyloxy)ethyl-3-piperidinecarboxylic acid,
(R)-1-(2-(2,2-Bis(2,5-difluorophenyl)ethoxy)ethyl)-3-piperidinecarboxylic acid,
(R)-N-(2-(4-Diphenylamino-1-butyloxy)ethyl)-3-piperidinecarboxylic acid,
(R)-1-(2-((2,2-Diphenylethenyl)oxy)ethyl)-3-piperidinecarboxylic acid,
Z-(R)-1-(2-((2-(2-Methylphenyl)-2-phenylethenyl)oxy)ethyl)-3-piperidinecarboxylic acid,
E-(R)-1-(2-((2 (2-Methylphenyl)-2-phenylethenyl)oxy)ethyl)-3-piperidinecarboxylic acid,
E-(R)-1-(2-((2-(2-Chlorophenyl)-2-phenylethenyl)oxy)ethyl)-3-piperidinecarboxylic acid,
Z-(R)-1-(2-((2-(2-Chlorophenyl)-2-phenylethenyl)oxy)ethyl)-3-piperidinecarboxylic acid,
E-(R)-1-(2-((2-(2-Chlorophenyl)-2-phenylethenyl)oxy)ethyl)-3-piperidinecarboxylic acid,
Z-(R)-1-(2-((2-(2-Chlorophenyl)-2-phenylethenyl)oxy)ethyl)-3-piperidinecarboxylic acid,
E-(R)-1-(2-((2-(3-Fluorophenyl)-2-(2-methylphenyl)-ethenyl)-oxy)ethyl)-3-piperidinecarboxylic acid,
Z-(R)-1-(2-((2-(3-Fluorophenyl)-2-(2-methylphenyl)ethenyl)-oxy)ethyl)-3-piperidinecarboxylic acid,
E-(R)-1-(2-((2-(3-Fluorophenyl)-2-(2-methylphenyl)ethenyl)oxy)ethyl)-3-piperidinecarboxylic acid,
Z-(R)-1-(2-((2-(3-Fluorophenyl)-2-(2-methylphenyl)ethenyl)oxy)ethyl)-3-piperidinecarboxylic acid,
(R)-1-(2-((2,2-Bis(4-fluorophenyl)ethenyl)oxy)ethyl)-3-piperidinecarboxylic acid,
(R)-1-(2-((2,2-Bis(2-chloro-4-fluorophenyl)ethenyl)oxy)ethyl)-3-piperidinecarboxylic acid,
(R)-1-(2-((2,2-Bis(2,4-difluorophenyl)ethenyl)oxy)ethyl)-3-piperidinecarboxylic acid,
(R)-1-(2-(((2,4-Difluorophenyl)-2-(2, 5-difluorophenyl)ethenyl)oxy)ethyl)3-piperidinecarboxylic acid,
(R)-1-(2-((2,2-Bis(2,5-difluorophenyl)ethenyl)oxy)ethyl)-3-piperidinecarboxylic acid,
(R)-1-(2-((2-(4-Fluoro-2-methylphenyl)-2-(2-methylphenyl)ethenyl)oxy) ethyl)-3-piperidinecarboxylic acid,
(R)-1-(2-((2,2-bis(2-Methylphenyl)ethenyl)oxy)ethyl)-3-piperidinecarboxylic acid,
(R)-1-(2-((2,2-bis(4-Fluoro-2-methylphenyl)ethenyl)oxy)ethyl)-3-piperidinecarboxylic acid,
E-(R)-1-(2-((2-(3-Methoxyphenyl)-2-(2-methylphenyl)ethenyl)oxy)ethyl)-3-piperidinecarboxylic acid,
Z-(R)-1-(2-((2-(3-Methoxyphenyl)-2-(2-methylphenyl)ethenyl)oxy)ethyl)-3-piperidinecarboxylic acid,
(R)-1-(2-((2-(2-Chlorophenyl)-2-(2-methylphenyl)ethenyl)oxy)ethyl)-3-piperidinecarboxylic acid,
(R)-1-(3-((2,2-bis(4-Fluorophenyl)ethenyl)oxy)-1-propyl)-3-piperidinecarboxylic acid,
(R)-1-(2-((2,2-Bis-(2-chlorophenyl)ethenyl)oxy)ethyl)-3-piperidinecarboxylic acid,
(R)-1-(2-((2,2-bis(2-Ethylphenyl)ethenyl)oxy)ethyl)-3-piperidinecarboxylic acid,
(R)-1-(2-((2,2-Bis(3-chlorophenyl)ethenyl)oxy)ethyl)-3-piperidinecarboxylic acid,
(R)-1-(2-((2,2-Diphenylethenyl)oxy)ethyl)-3-piperidinecarboxylic acid ethyl ester,
(R)-1-(3-((2,2-Diphenylethenyl)oxy)-1-propyl)-3-piperidinecarboxylic acid,
1-(2-((2,2-bis(3-Fluorophenyl)ethenyl)oxy)ethyl)-1,2,5,6-tetrahydro-3-pyridinecarboxylic acid,
1-(2-((2,2-bis(4-Fluoro-2-methylphenyl)ethenyl)oxy)ethyl)-1,2,5,6-tetrahydro-3-pyridinecarboxylic acid,
1-(2-((2-(4-Fluoro-2-methylphenyl)-2-(2-methylphenyl)ethenyl)oxy) ethyl)-1,2,5,6-tetrahydro-3-pyridinecarboxylic acid,
1-(2-((2-(2-Fluorophenyl)-2-(2-methylphenyl)ethenyl)oxy)-ethyl)-1,2,5,6-tetrahydro-3-pyridinecarboxylic acid,
1-(2-((2-(2,4-Dichlorophenyl)-2-(2-methylphenyl)ethenyl)-oxy)ethyl)-1,2,5,6-tetra-hydro-3-pyridinecarboxylic acid,
1-(2-((2,2-bis(2-Ethylphenyl)ethenyl)oxy)ethyl)-1,2,5,6-tetrahydro-3-pyridinecarboxylic acid,
1-(2-((2,2-bis(2-Ethylphenyl)ethenyl)oxy)ethyl)-1,2,5,6-tetrahydro-3-pyridinecarboxylic acid,
1-(2-(((2-(2-Chlorophenyl)-2-(2-methylphenyl)ethenyl)oxy)ethyl)-1,2,5,6-tetrahydro-3-pyridinecarboxylic acid,
1-(2-((2,2-bis(2-Methylphenyl)ethenyl)oxy)ethyl)-1,2,5,6-tetrahydro-3-pyridinecarboxylic acid,
1-(2-((2-(3-Methoxyphenyl)-2-(2-methylphenyl)ethenyl)oxy)ethyl)-1,2,5,6-tetrahydro-3-pyridine carboxylic acid,
1-(2-((2-(3-Chlorophenyl)-2-(2-methylphenyl)ethenyl)oxy)ethyl)-1,2,5,6-tetrahydro-3-pyridinecarboxylic acid,
1-(2-((2,2-bis(2-Chlorophenyl)ethenyl)oxy)ethyl)-1,2,5,6-tetrahydro-3pyridinecarboxylic acid, 1-(2-((2,2-Diphenylethenyl)oxy)ethyl)-1,2,5,6-tetrahydro-3-pyridinecarboxylic acid,
N-(2-(3,3-Diphenyl-1-propyloxy)ethyl)-1,2,5,6-tetrahydro-3-pyridinecarboxylic acid ethyl ester, or
N-(2-(3,3-Diphenyl-1-propyloxy)ethyl)-1,2,5,6-tetrahydro-3-pyridinecarboxylic acid;
or a pharmaceutically acceptable salt thereof.

16. The method according to claim 2 wherein the compound is:
(R)-1-(2-((2-(2-Methylphenyl)-2-(3-methyl-2-thienyl)ethenyl)oxy)ethyl)-3-piperidinecarboxylic acid,
(R)-1-(2-((2,2-bis(3-Methyl-2-thienyl)ethenyl)oxy)ethyl)3-piperidinecarboxylic acid, or
(R)-1-(2-((2,2-bis(3-Methyl-2-thienyl)ethenyl)oxy)ethyl)-3-piperidinecarboxylic acid ethyl ester;
or a pharmaceutically acceptable salt thereof.

17. The method according to claim 2 wherein the compound is:
(S)-1-(2-(((Bis(2-methylphenyl)methylene)amino)oxy)ethyl)-3 piperidinecarboxylic acid,
(R)-1-(2-(((Diphenylmethylene)amino)oxy)ethyl)-3-piperidinecarboxylic acid,
(R)-1-(2-(((Bis(2-chloro-4-fluorophenyl)methylene)amino)oxy)ethyl)-3-piperidinecarboxylic acid,
(R)-1-(2-(((Bis(2,4-diflourophenyl)methylene)amino)oxy)ethyl)-3-piperidinecarboxylic acid,
(R)-1-(2-(((Bis(4-fluoro-2-methylphenyl)methylene)amino)oxy)ethyl)-3-piperidinecarboxylic acid, (R)-1-(2-((((3-Methoxyphenyl)phenylmethylene)amino)
oxy)ethyl)-3-piperidinecarboxylic acid,
(R)-1-(2-((((2-Methylphenyl)(3-methoxyphenyl)
methylene)amino)oxy)ethyl)-3-piperidinecarboxylic
acid,
(R)-1-(2-(((Bis(4-chloro-2-methylphenyl)methylene)
amino)oxy)ethyl)-3-piperidinecarboxylic acid,
(R)-1-(2-(((Bis(2-methylphenyl)methylene)amino)oxy)
ethyl)-3-piperidinecarboxylic acid,
(R)-1-(2-((((2,4-Difluorophenyl)-(2,5-difluorophenyl)
methylene)amino)oxy) ethyl)-3-piperidinecarboxylic
acid,
(R)-1-(2-(((Bis(3,5-difluorophenyl)methylene)amino)
oxy)ethyl)-3-piperidinecarboxylic acid,
(R)-1-(2-((((2-Fluorophenyl)-(2-methylphenyl)
methylene)amino)oxy)ethyl)-3-piperidinecarboxylic
acid,
(R)-1-(2-(((Bis(2,5-difluorophenyl)methylene)amino)
oxy)ethyl)-3-piperidinecarboxylic acid,
(R)-1-(2-((((2-Chlorophenyl)-(2-methylphenyl)
methylene)amino)oxy)ethyl)-3-piperidinecarboxylic
acid,
1-(2-(((Diphenylmethylene)amino)oxy)ethyl)-3-
piperidinecarboxylic acid,
1-(2-(((Phenyl-2-pyridinylmethylene)amino)oxy)ethyl)-
3piperidinecarboxylic acid,
1-(2-(((Phenyl-1H-pyrrol-2-ylmethylene)amino)oxy)
ethyl)-3piperidinecarboxylic acid,
1-(2-(((Bis(4-chlorophenyl)methylene)amino)oxy)ethyl)-
3piperidinecarboxylic acid,
1-(2-((((4-Azidophenyl)phenylmethylene)amino)oxy)
ethyl)-3piperidinecarboxylic acid,
(S)-1-(2-(((Diphenylmethylene)amino)oxy)ethyl)-3-
piperidinecarboxylic acid,
1-(2-((((4-Fluorophenyl)phenylmethylene)amino)oxy)
ethyl)-3-piperidinecarboxylic acid,
1-(2-((((2-Chlorophenyl)phenylmethylene)amino)oxy)
ethyl)-3-piperidinecarboxylic acid,
1-(2-((((4-Chloro-2-methylphenyl)-(2-methylphenyl)
methylene)amino)oxy)ethyl)-3-piperidinecarboxylic
acid,
1-(2-((((3-Azidophenyl)phenylmethylene)amino)oxy)
ethyl)-3-piperidinecarboxylic acid,
1-(2-((((3-Nitrophenyl)phenylmethylene)amino)oxy)
ethyl)-3-piperidinecarboxylic acid,
1-(2-(((Bis(2-hydroxyphenyl)methylene)amino)oxy)
ethyl)-3-piperidinecarbocylic acid,
1-(2-(((Bis(3-methoxyphenyl)methylene)amino)oxy)
ethyl)-3-piperidinecarboxylic acid,
1-(2-((((2-Methylphenyl)(3-methylphenyl)methylene)
amino)oxy)ethyl)-3-piperidinecarboxylic acid,
1-(2-((((4-Methyl-2-thienyl)-(2-tolyl)methylene)amino)
oxy)ethyl)-3-piperidinecarboxylic acid,
1-(2-((((3-Hydroxyphenyl)phenylmethylene)amino)oxy)
ethyl)-3-piperidinecarboxylic acid,
1-(2-(((Bis(2-tolyl)methylene)amino)oxy)-1-propyl)-3-
piperidinecarboxylic acid,
(R)-1-(2-((((2,4-Dichlorophenyl)-(3-methoxyphenyl)
methylene)amino)oxy)ethyl)-3-piperidinecarboxylic
acid,
(R)-1-(2-((((2-Methylphenyl)-(3-(trifluoromethyl)
phenyl)methylene)amino)oxy)ethyl)-3-
piperidinecarboxylic acid, 1-(3-(((Diphenylmethylene)amino)oxy)-1-propyl)-3-
piperidinecarboxylic acid,
(R)-1-(2-(((2,2-Diphenylethylidene)amino)oxy)ethyl)-3-
piperidinecarboxylic acid,
(R)-1-(2-(((2-(2-Methylphenyl)-2-phenylethylidene)
amino)oxy)ethyl)-3-piperidinecarboxylic acid,
E/Z-(R)-1-(2-(((2-(2-Methylphenyl)-2-(4-fluoro-2-
methylphenyl)ethylidene)amino)-oxy)ethyl)-3-
piperidinecarboxylic acid,
(R)-1-(2-((2-((3-Methylphenyl)(phenyl)amino)ethoxy)
ethyl)-3-piperidinecarboxylic acid,
(R)-1-(2-(2-((3-Chlorophenyl)(phenyl)amino)ethoxy)
ethyl)-3-piperidinecarboxylic acid,
(R)-N-(2-(2-(Diphenylamino)ethoxy)ethyl)-3-
piperidinecarboxylic acid,
(R)-N-(4-(2-(Diphenylamino)ethoxy)-1-butyl)-3-
piperidinecarboxylic acid,
(R)-N-(3-(3-Diphenylamino-1-propyloxy)-1-propyl)-3-
piperidinecarboxylic acid,
((R)-N-(2-(2-(Diphenylamino)ethoxy)ethyl)-3-
piperidinecarboxylic acid ethyl ester,
(R)-1-(2-(((Bis(4-fluoro-2-methylphenyl)methylene)
amino)oxy)ethyl)-3-piperidinecarboxylic acid ethyl
ester,
1-(2-(((Diphenylmethylene)amino)oxy)ethyl)-1,2,5,6-
tetrahydro-3-pyridinecarboxylic acid,
1-(2-((((2-methylphenyl)phenylmethylene)amino)oxy)
ethyl)-1,2,5,6-tetrahydro-3-pyridinecarboxylic acid,
1-(2-((((3-Fluorophenyl)-(2-methylphenyl)methylene)
amino)oxy)ethyl)-1,2,5,6-tetrahydro-3-
pyridinecarboxylic acid,
1-(2-((((2-Chlorophenyl)-(2-methylphenyl)methylene)
amino)oxy)ethyl)-1,2,5,6-tetrahydro-3-
pyridinecarboxylic acid,
1-(2-((((2-Methylphenyl)-(3-(trifluoromethyl)phenyl)
methylene)amino)oxy)ethyl)-1,2,5,6-tetrahydro-3-
pyridinecarboxylic acid,
1-(2-((((4-Chloro-2-methylphenyl)(2-methylphenyl)
methylene)amino)oxy)ethyl)-1,2,5,6-tetrahydro-3-
pyridinecarboxylic acid,
1-(2-((((2-Chlorophenyl)phenylmethylene)amino)oxy)
ethyl)-1,2,5,6-tetrahydro-3-pyridinecarboxylic acid,
1-(2-((((3-Chlorophenyl)(2-methylphenyl)methylene)
amino)oxy)ethyl)-1,2,5,6-tetrahydro-3-
pyridinecarboxylic acid,
1-(2-((((3-Methoxyphenyl)phenylmethylene)amino)oxy)
ethyl)-1,2,5,6-tetrahydro-3-pyridinecarboxylic acid,
1-(2-((((3-Methoxyphenyl)(2-methylphenyl)methylene)
amino)oxy)ethyl)-1,2,5,6-tetrahydro-3-
pyridinecarboxylic acid,
1-(2-((((4-Fluoro-2-methylphenyl)(2-methylphenyl)
methylene)amino)oxy)ethyl)-1,2,5,6-tetrahydro-3-
pyridinecarboxylic acid,
1-(2-((((2-Fluorophenyl)(2-methylphenyl)methylene)
amino)oxy)ethyl)-1,2,5,6-tetrahydro-3-
pyridinecarboxylic acid,
1-(2-((((3,4-Dichlorophenyl)-(2-methylphenyl)
methylene)amino)oxy)ethyl)-1,2,5,6-tetrahydro-3-
pyridinecarboxylic acid,
1-(2-(((Bis(2-ethylphenyl)methylene)amino)oxy)ethyl)-
1,2,5,6-tetrahydro-3-pyridinecarboxylic acid,
1-(2-(((2-(4-Fluoro-2-methylphenyl)-(2-methylphenyl)
ethylidene)amino)oxy)ethyl)-1,2,5,6-tetrahydro-3-
pyridinecarboxylic acid, 1-(2-((((2-Chlorophenyl)phenylmethylene)amino)oxy)
ethyl)-1,2,5,6-tetrahydro-3-pyridinecarboxylic acid
ethyl ester, 1-(2-(((Diphenylmethylene)amino)oxy)ethyl)-1,2,5,6-
tetrahydro-3-pyridinecarboxylic acid ethyl ester, 1-(2-(((Bis(4-fluoro-2-methylphenyl)methylene)amino)
oxy)ethyl)-1,2,5,6-tetrahydro-3-pyridinecarboxylic
acid, 1-(2-(((Bis(2-methylphenyl)methylene)amino)oxy)
ethyl)-1,2,5,6-tetrahydro-3-pyridinecarboxylic acid
ethyl ester, or 1-(2-(((Bis(4-Fluoro-2-methylphenyl)methylene)amino)
oxy)ethyl)-1,2,5,6-tetrahydro-3-pyridinecarboxylic
acid ethyl ester;

or a pharmaceutically acceptable salt thereof.

18. The method according to claim 2 wherein the compound is:

E-(R)-1-(2-((((3-Methoxyphenyl)-(4-methyl-2-thienyl)
methylene)amino) oxy)ethyl)-3-piperidinecarboxylic
acid, Z-(R)-1-(2-((((3-Methoxyphenyl)-(4-methyl-2-thienyl)
methylene)amino) oxy)ethyl)-3-piperidinecarboxylic
acid, E-(R)-1-(2-((((2-Methylphenyl)-(3-methyl-2-thienyl)
methylene)amino)oxy)ethyl)-3-piperidinecarboxylic
acid, Z-(R)-1-(2-((((2-Methylphenyl)-(3-methyl-2-thienyl)
methylene)amino)oxy)ethyl)-3-piperidinecarboxylic
acid, E-(R)-1-((2-((((2-Methyl-2H-1,2,4-triazol-3-yl)-2-
thienyl-methylene)-amino) oxy)ethyl-3-
piperidinecarboxylic acid, Z-(R)-1-(2-((((2-Methyl-2H-1,2,4-triazol-3-yl)-2-thienyl-
methylene)-amino)oxy)ethyl-3-piperidinecarboxylic
acid, E-(R)-1-(2-((((2-Methyl-2H-1,2,4-triazol-3-yl)-2-thienyl-
methylene)amino) oxy)ethyl)-3-piperidinecarboxylic
acid, Z-(R)-1-(2-((((2-Methyl-2H-1,2,4-triazol-3-yl)-2-thienyl-
methylene)amino) oxy)ethyl)-3-piperidinecarboxylic
acid, (R)-1-(2-((((3-Azidophenyl)(3-methyl-2-thienyl)
methylene)amino)oxy)ethyl)-3-piperidinecarboxylic
acid, (R)-1-(2-(((Bis(3-ethyl-2-thienyl)methylene)amino)oxy)
ethyl)-3-piperidine carboxylic acid, (R)-1-(2-((((2,4-Dichlorophenyl)(3-methyl-2-thienyl)
methylene)amino)oxy)ethyl)-3-piperidinecarboxylic
acid, (R)-1-(2-((((4-Chloro-2-methylphenyl)-(3-methyl-2-
thienyl)methylene) amino)oxy)ethyl)-3-
piperidinecarboxylic acid, E-1-(2-((((2-Methylphenyl)-(3-methyl-2-thienyl)
methylene)-amino)oxy)ethyl)-3-piperidinecarboxylic
acid, Z-1-(2-((((2-Methylphenyl)-(3-methyl-2-thienyl)
methylene)-amino)oxy)ethyl)-3-piperidinecarboxylic
acid, 1-(2-((((1-Methyl-i H-imidazol-2-yl)phenylmethylene)
amino)oxy)ethyl)3-piperidinecarboxylic acid, 1-(2-((((2,4-Dichlorophenyl)-(3-methyl-2-thienyl)
methylene)amino)oxy)ethyl)-3-piperidinecarboxylic
acid, (S)-1-(2-(((Bis(3-methyl-2-thienyl)methylene)amino)
oxy)ethyl)-3-piperidinecarboxylic acid, (S)-1-(2-((((2-Methylphenyl)-(3-methyl-2-thienyl)
methylene)amino)oxy)ethyl)-3-piperidinecarboxylic
acid, (R)-1-(2-((((3-Methoxyphenyl)-(3-methyl-2-thienyl)
methylene)amino)oxy)ethyl)-3-piperidinecarboxylic
acid, (R)-1-(2-((((2-Ethylphenyl)-(3-methyl-2-thienyl)
methylene)amino)oxy)ethyl)-3-piperidinecarboxylic
acid, (R)-1-(2-((((3-Methyl-2-thienyl)-2-thienylmethylene)
amino)oxy)ethyl)-3-piperidinecarboxylic acid, E-(R)-1-(2-((((2-Methylphenyl)-(3-methyl-2-thienyl-
methylene)amino)oxy)ethyl)-3-piperidinecarboxylic
acid, (R)-1-(2-(((Bis(3-methyl-2-thienyl)methylene)amino)
oxy)ethyl)-3-piperidinecarboxylic acid, Z-(R)-1-(2-((((2-Methylphenyl)-(3-methyl-2-thienyl-
methylene)amino)oxy)ethyl)-3-piperidinecarboxylic
acid, (S)-1-(2-((((2-Methylphenyl)-(3-methyl-2-thienyl)
methylene)amino)oxy)ethyl)-3-piperidinecarboxylic
acid ethyl ester, E-(R)-1-(2-((((2-Methylphenyl)-(3-methyl-2-thienyl)
methylene)amino)oxy)ethyl)-3-piperidinecarboxylic
acid ethyl ester, Z-(R)-1-(2-((((2-Methylphenyl)-(3-methyl-2-thienyl)
methylene)amino)oxy)ethyl)-3-piperidinecarboxylic
acid ethyl ester, E-(R)-1-(2-((((2-Methylphenyl)-(3-methyl-2-thienyl)
methylene)amino)oxy)ethyl)-3-piperidinecarboxylic
acid ethyl ester, or Z-(R)-1-(2-((((2-Methylphenyl)-(3-methyl-2-thienyl)
methylene)amino)oxy)ethyl)-3-piperidinecarboxylic
acid ethyl ester, 1-(2-(((Bis(3-methyl-2-thienyl)methylene)amino)oxy)
ethyl)-1,2,5,6-tetrahydro-3-pyridinecarboxylic acid, 1-(2-((((3-Methyl-2-thienyl)-2-thienylmethylene)amino)
oxy)ethyl)-1,2,5,6-tetrahydro-3-pyridinecarboxylic
acid, 1-(2-((((2-Methylphenyl)-(3-methyl-2-thienyl)
methylene)amino)oxy)ethyl)-1,2,5, 6-tetrahydro-3-
pyridinecarboxylic acid, 1-(2-((((2,4,-Dichlorophenyl)-(3-Methyl-2-thienyl)
methylene)amino)oxy)ethyl)-1,2,5,6-tetrahydro-3-
pyridinecarboxylic acid, 1-(2-(((Phenyl-2-thienylmethylene)amino)oxy)ethyl)-1,
2,5,6-tetrahydro-3-pyridinecarboxylic acid, 1-(2-((((4-Chloro-2-methylphenyl)-(3-methyl-2-thienyl)
methylene)amino)oxy)ethyl)-1,2,5,6-tetrahydro-3-
pyridinecarboxylic acid, 1-(2-((((4-Fluoro-2-methylphenyl)-(3-methyl-2-thienyl)
methylene)amino)oxy)ethyl)-1,2,5,6-tetrahydro-3-
pyridinecarboxylic acid, or 1-(2-((((2-Methylphenyl)(3-methyl-2-thienyl)methylene)
amino)oxy)ethyl)-1,2,5,6-tetrahydro-3-
pyridinecarboxylic acid ethyl ester; or a pharmaceutically acceptable salt thereof.

19. The method according to claim 2 wherein the compound is 1-(2-(((Diphenylmethylene)amino)oxy)ethyl)-3-
piperidinecarboxamide, or a pharmaceutically acceptable salt thereof.

* * * * *